(12) United States Patent
Paul et al.

(10) Patent No.: US 12,071,471 B2
(45) Date of Patent: Aug. 27, 2024

(54) IMMUNOGLOBULINS DIRECTED TO BACTERIAL, VIRAL AND ENDOGENOUS POLYPETIDES

(71) Applicant: COVALENT BIOSCIENCE INCORPORATED, Tuxedo Park, NY (US)

(72) Inventors: Sudhir Paul, Missouri City, TX (US); Stephanie Planque, Houston, TX (US); Yasuhiro Nishiyama, Houston, TX (US); Eric L. Brown, Houston, TX (US); Keri C. Smith, Houston, TX (US); Hiroaki Taguchi, Houston, TX (US)

(73) Assignee: COVALENT BIOSCIENCE INCORPORATED, Tuxedo Park, NY (US)

( * ) Notice: Subject to any disclaimer, the term of this patent is extended or adjusted under 35 U.S.C. 154(b) by 1282 days.

(21) Appl. No.: 15/978,801

(22) Filed: May 14, 2018

(65) Prior Publication Data
US 2019/0144528 A1 May 16, 2019

Related U.S. Application Data

(63) Continuation of application No. 12/589,440, filed on Oct. 23, 2009, now Pat. No. 9,969,797, which is a continuation of application No. PCT/US2008/005221, filed on Apr. 23, 2008.

(60) Provisional application No. 60/913,335, filed on Apr. 23, 2007.

(51) Int. Cl.
| C07K 16/18 | (2006.01) |
| C07K 16/10 | (2006.01) |
| C07K 16/12 | (2006.01) |
| G01N 33/68 | (2006.01) |
| A61K 39/00 | (2006.01) |

(52) U.S. Cl.
CPC .......... *C07K 16/18* (2013.01); *C07K 16/1063* (2013.01); *C07K 16/109* (2013.01); *C07K 16/1271* (2013.01); *G01N 33/6854* (2013.01); *A61K 2039/505* (2013.01); *C07K 2317/52* (2013.01); *C07K 2317/56* (2013.01); *C07K 2317/565* (2013.01); *C07K 2317/567* (2013.01); *C07K 2317/622* (2013.01)

(58) Field of Classification Search
None
See application file for complete search history.

(56) References Cited

U.S. PATENT DOCUMENTS

| 6,156,541 A | 12/2000 | Paul et al. |
| 7,175,996 B1 | 2/2007 | Watkins et al. |
| 9,969,797 B2 | 5/2018 | Paul et al. |
| 2009/0117115 A1 | 5/2009 | Paul et al. |

FOREIGN PATENT DOCUMENTS

| EP | 0368684 B2 | 5/1990 |
| WO | 1997/003696 A1 | 2/1997 |
| WO | 2004/003019 A2 | 1/2004 |
| WO | 2004/087738 A2 | 10/2004 |
| WO | WO2004/087735 | * 10/2004 |

OTHER PUBLICATIONS

Niesner, U., et al., "Quantitation of the tumor-targeting properties of antibody fragments conjugated to cell-permeating HIV-1 TAT peptides" Bioconjug. Chem. (2002) 13(4):729-36.
Mitra, G., et al., "Enhanced stability and therapeutic utility of proteins upon conjugation with hydrophilic polymers" Hindustan Antibiot Bull. (1993) 35(1-2):133-56.
Karle, S., et al., "Cross-clade HIV-1 neutralization by an antibody fragment from a lupus phage display library" AIDS (2004) 18(2):329-31.
Zhou, Y-X, et al., "Prospects for immunotherapeutic proteolytic antibodies" J. Immunol. Methods (2002) 269(1-2):257-68.
Nishiyama, Y., et al., "Antibodies to the superantigenic site of HIV-1 gp120: hydrolytic and binding activities of the light chain subunit" Mol. Immunol. (2007) 44(10):2707-18.
Taguchi, H., et al., "A mechanism-based probe for gp120-Hydrolyzing antibodies" Bioorg. Med. Chem. Lett. (2002) 12(21):3167-70.
Neshat, M.N., et al., "Mapping the B cell superantigen binding site for HIV-1 gp120 on a V(H)3 Ig" Int. Immunol. (2000) 12(3):305-12.
Paul, S., et al., "Specific HIV gp120-cleaving antibodies induced by covalently reactive analog of gp120" J. Biol. Chem. (2003) 278(22):20429-35.
Taguchi, H,, "Catalytic Hydrolysis of Amyloid B-Peptide (AB) by Human Antibodies" Poster Session P4: Therapeutics and Therapeutic Strategies—Therapeutic Strategies, Amyloid Based, p. 4-331, 2004.
Paul, et al., "Natural catalytic antibodies: peptide-hydrolyzing activities of Bence Jones proteins and VL fragment" J. Biol. Chem. (1995) 270(25):15257-61.
Novotny, et al., "Structural invariants of antigen binding: comparison of immunoglobulin VL—VH and VL-VL domain dimers" Proc. Natl. Acad. Sci. (1985) 82(14):4592-6.

(Continued)

*Primary Examiner* — Meera Natarajan
(74) *Attorney, Agent, or Firm* — Robert C. Netter, Jr.; Dann, Dorfman, Herrell & Skillman

(57) ABSTRACT

Disclosed are antibodies (immunoglobulins) and fragments thereof that hydrolyze or bind polypeptide antigens belonging to *Staphylococcus aureus*, hepatitis C virus, human immunodeficiency virus and Alzheimer's disease. Also disclosed are novel methods to improve the antigen reactivity of the immunoglobulins and to treat a pathophysiological condition using the immunoglobulins as therapeutics.

17 Claims, 43 Drawing Sheets

Specification includes a Sequence Listing.

(56) References Cited

OTHER PUBLICATIONS

Rangan, et al., "Degradation of beta-amyloid by proteolytic antibody light chains" Biochemistry (2003) 42(48):14328-34.

Lacroix-Desmazes, et al., "High levels of catalytic antibodies correlate with favorable outcome in sepsis" Proc. Natl. Acad. Sci. (2005) 102(11):4109-13.

Joos, et al., "Long-term multiple-dose pharmacokinetics of human monoclonal antibodies (MAbs) against human immunodeficiency virus type 1 envelope gp120 (MAb 2G12) and gp41 (MAbs 4E10 and 2F5)" Antimicrob. Agents Chemother. (2006) 50(5):1773-9.

Planque, et al., "Characterization of gp120 Hydrolysis by IgA Antibodies from Humans without HIV Infection" AIDS Res. Hum. Retroviruses (2007) 23(12):1541-54.

Paul, et al., "Naturally occurring proteolytic antibodies: selective immunoglobulin M-catalyzed hydrolysis of HIV gp120" J. Biol. Chem. (2004) 279(38):39611-9.

Muyldermans, S. "Single domain camel antibodies: current status" J. Biotechnol. (2001) 74(4):277-302.

* cited by examiner

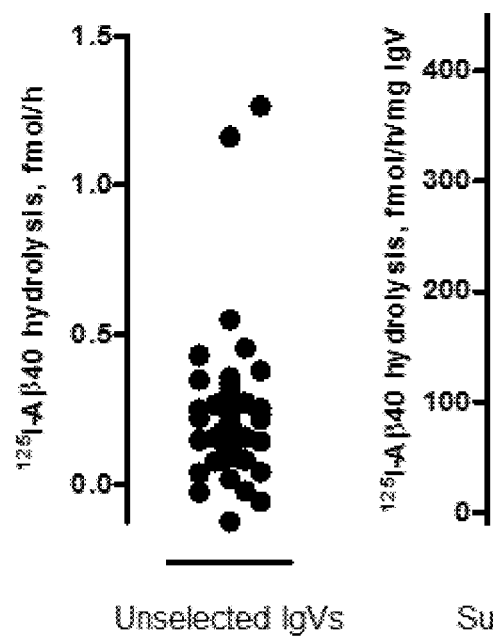
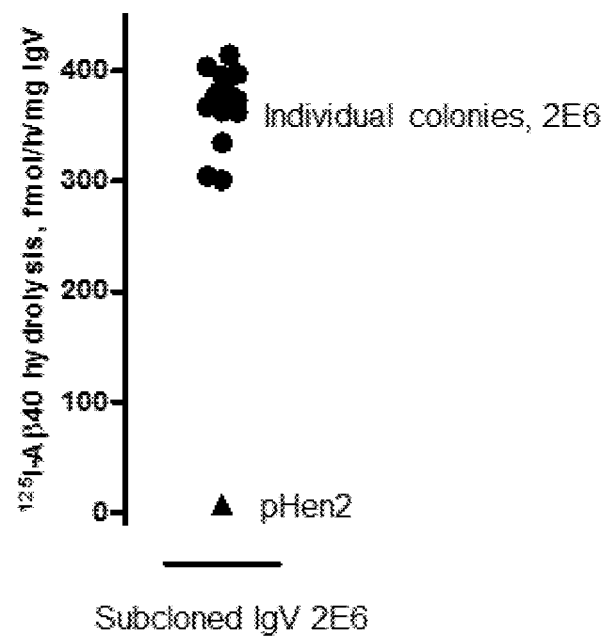
FIG. 2A FIG. 2B

IgV$_{L2}$-t 2E6; SEQ ID NO: 8
QSALTQPASVSGSPGQSITISCTGTSSDVGGYNYVSWYQQHPGKAPKLMISEVSNRPSGVSNRFSGSKSGNTASLTISGPQTEDEADYYCSSYTSSSTPV 100
VFGGGTQLTVLGSSGGGGSGGGGSALDIQLTQSPSSLPASVGDRVTITCRASQSISSYLNWYQQKPGKAPKLLIYAASSLQSGVPSRFSGSGSGTDF 200
TLTISSLQPEDFATYYCQQSYSTHTFGQGTKLEIKRAAAHHHHHHGAAEQKLISEEDLNGAA 262

IgV$_L$-t' 5D3; SEQ ID NO: 9
EIVLTQSPGTLSLSPGERATLSCRASQSVGGSYLAWYQQKPGQAPRLLIYGASSRATGIPDRFSGSGSGTDFTLTISRLEPEDFAVYYCQLYGGSPMYTF 100
GQGTKLEIKRSSGGGGSGGGGSALQVLLQSACAPTLFPAAAHHHHHHGAAEQKLISEEDLNGAA 168

IgV$_L$-t' 1E4; SEQ ID NO: 10
QSVLTQPPSVSAAPGQKVTISCSGSSSNIGNNYVSWYQQLPGTAPKLLIYDNERRPSGIPDRFSGSKSGTSATLAITGLQPGDEADYYCAAWDNTLRGGV 100
FGGGTQLTVLGSSGGGGSGGGGSALQVLQESGAGEERGRVWCTHTKGPSVFPAAAHHHHHHGAAEQKLISEEDLNGAA 182

IgV$_L$-t' 5H3; SEQ ID NO: 11
QSVLTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSGV 100
VFGGGTQLTVLGSSGGGGSGGGGSALQVSCGVGSHASAPTLFPAAAHHHHHHGAAEQKLISEEDLNGAA 172

FIG. 5

VH domain sequences, scFv-t 5D3 constructs

V$_H$ 5D3-D4; SEQ ID NO 12
QVQLLQSGAEVKKPGASVKVSCKASGYTFTGYYMHWVRQAPGQGLEWMGWINPNSGGTNYAQKFQGRVTMTRD
TSISTAYMELSRLRSDDTAVYYCARWSHSSGLDYWGQGTLVTVSSGSACAPTLFP*AAAHHHHHHGAAEQKLIS
EEDLNGAA*

V$_H$ 5D3-D10; SEQ ID NO 13
QVQLLQSGAEVKKPGASVKVSCKASGYTFTSYDINWVRQATGQGLEWMGWMNPNSGNTGYAQKFQGRVTMTRN
TSISTAYMELSSLRSEGTAVYYCATGSRYDYWGQGTLVTVSSGSACAPTLFP*AAAHHHHHHGAAEQKLISEED
LNGAA*

V$_H$ 5D3-E4 ; SEQ ID NO 14
QVQLLQSGPGLVKPSETLSLTCTVSGGSISSGSYYWSWIRQPAGKGLEWIGRIYTSGSTNYNPSLKSRVTISV
DTSKNQFSLKLSSVTAADTAVYYCARVGRLNWFDPWGQGTLVTVSSGSACAPTLFP*AAAHHHHHHGAAEQKLI
SEEDLNGAA*

V$_H$ 5D3-E6 ; SEQ ID NO 15
QVQLLQSGPGLVKPSETLSLTCTVSGGSISSGGYYWSWIRQHPGKGLEWIGYIYYSGSTYYNPSLKSRVTISV
DTSKNQFSLKLSSVTAADTAVYYCARAGDSSGPGDYWGQGTLVTVSSGSACAPTLFP*AAAHHHHHHGAAEQKL
ISEEDLNGAA*

L-t 5D3 sequence; SEQ ID NO 16
EIVLTQSPGTLSLSPGERATLSCRASQSVGGSYLAWYQQKPGQAPRLLIYGASSRATGIPDRFSGSGSGTDFT
LTISRLEPEDFAVYYCQLYGGSPMYTFGQGTKLEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC*AAA
HHHHHHGAAEQKLISEEDLNGAA*

IgV$_{L2}$-t 5D3 sequence; SEQ ID NO 17
EIVLTQSPGTLSLSPGERATLSCRASQSVGGSYLAWYQQKPGQAPRLLIYGASSRATGIPDRFSGSGSGTDFT
LTISRLEPEDFAVYYCQLYGGSPMYTFGQGTKLEIKRSGGGGSGGGGSGGSALEIVLTQSPGTLSLSPGERA
TLSCRASQSVGGSYLAWYQQKPGQAPRLLIYGASSRATGIPDRFSGSGSGTDFTLTISRLEPEDFAVYYCQLY
GGSPMYTFGQGTKLEIKR*AAAHHHHHHGAAEQKLISEEDLNGAA*

FIG. 7

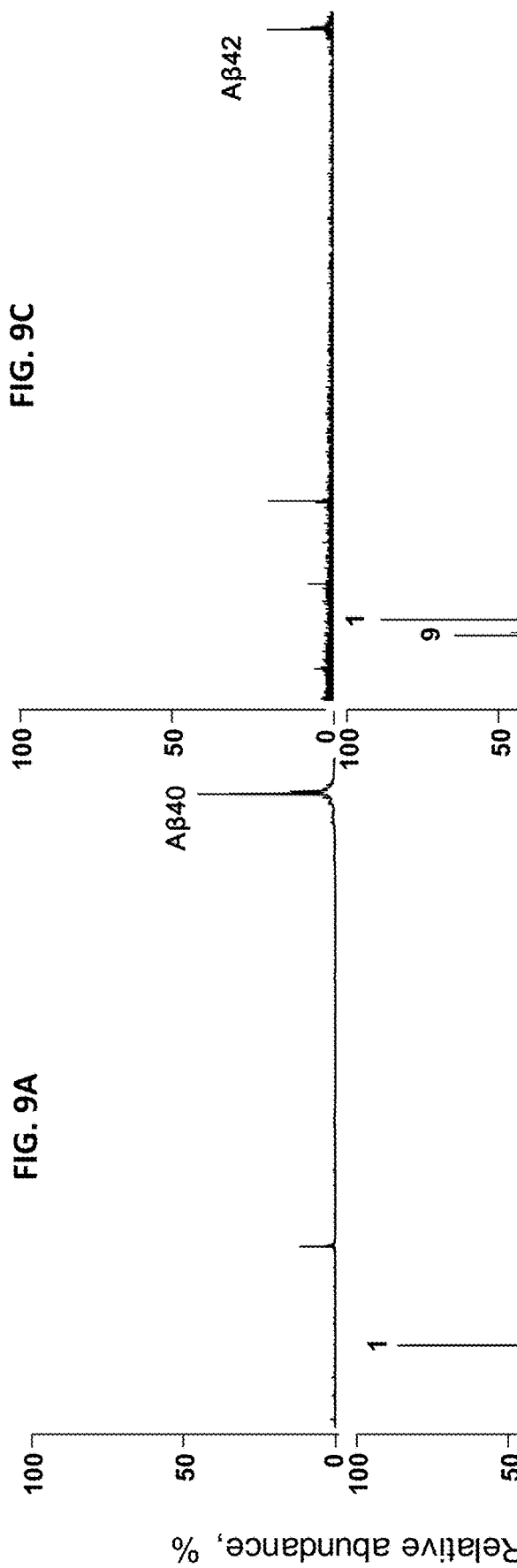
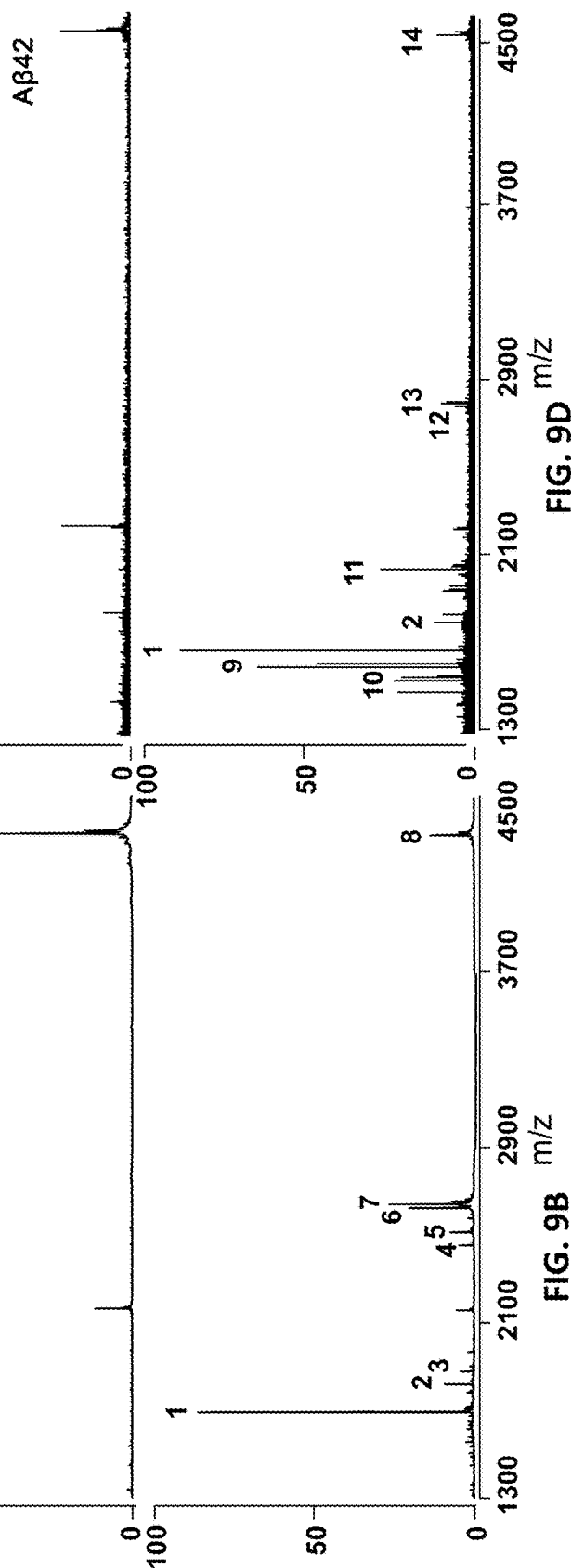
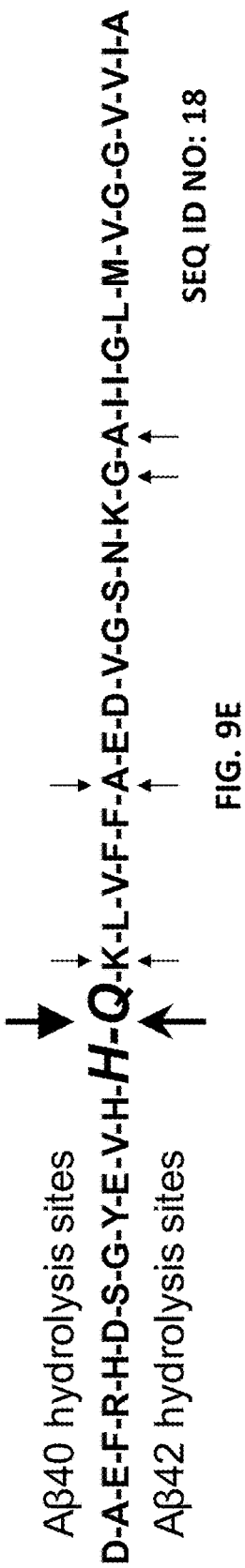
FIG. 9A FIG. 9B FIG. 9C FIG. 9D
FIG. 9E
Aβ40 hydrolysis sites
D-A-E-F-R-H-D-S-G-Y-E-V-H-*H-Q*-K-L-V-F-F-A-E-D-V-G-S-N-K-G-A-I-I-G-L-M-V-G-G-V-I-A
Aβ42 hydrolysis sites
SEQ ID NO: 18

- $R_1$ = Benzyloxycarbonyl, $R_2$ = Phenyl
- $R_1$ = Biotinamidohexanoyl, $R_2$ = Phenyl
- $R_1$ = Biotinamidohexanoyl, $R_2$ = H

MRGSHHHHHHGADASEGYGPREKKPVSINHNIVEYNDGTFKYQSRPKFNS

TPKYIKFKHDYNILEFNDGTFEYGARPQFNKPAAKTDATIKKEQKLIQAQ

NLVREFEKTHTVSAHRKAQKAVNLVSFEYKVKKMVLQERIDNVLKQGLVK

SEQ ID NO: 19 scFv1C7 VH domain (1C7: SEQ ID NOS 24-25; VH3-33: SEQ ID NOS 26-27)

B. VH domain

```
                1
1C7       GAG GTG CAG CTG GTG GAG TCT GGG GGA GGC GTG GTC CAG CCT GGG AGG TCC CTG AGA CTC TCC TGT GCA GCG TCT GGA TTC
           ..  ...  ...  ...  ...  ...  ...  ...  ...  ...  ...  ...  ...  ...  ...  ...  ...  ...  ...  ...  ...  ...  ...  ...  ...  ...  ...
VH3-33    GLU VAL GLN LEU VAL GLU SER GLY GLY GLY VAL VAL GLN PRO GLY ARG SER LEU ARG LEU SER CYS ALA ALA SER GLY PHE
1C7       ---  ---  ---  ---  ---  ---  ---  ---  ---  ---  ---  ---  ---  ---  ---  ---  ---  ---  ---  ---  ---  ---  ---  ---  ---  ---  ---
VH3-33    ---  ---  ---  ---  ---  ---  ---  ---  ---  ---  ---  ---  ---  ---  ---  ---  ---  ---  ---  ---  ---  ---  ---  ---  ---  ---  ---

82                                                                                                      162
1C7       ACC TTC AGT AGC TAT GGC ATG CAC TGG GTC CGC CAG GCT CCA GGC AAG GGG CTG GAG TGG GTG GCA GTT ATA TGG TAT GAT
           ..  ...  ...  ...  ...  ...  ...  ...  ...  ...  ...  ...  ...  ...  ...  ...  ...  ...  ...  ...  ...  ...  ...  ...  ...  ...  ...
VH3-33    THR PHE SER SER TYR GLY MET HIS TRP VAL ARG GLN ALA PRO GLY LYS GLY LEU GLU TRP VAL ALA VAL ILE TRP TYR ASP
1C7       ---  ---  ---  ---  ---  ---  ---  ---  ---  ---  ---  ---  ---  ---  ---  ---  ---  ---  ---  ---  ---  ---  ---  ---  ---  ---  ---
VH3-33    ---  ---  ---  ---  ---  ---  ---  ---  ---  ---  ---  ---  ---  ---  ---  ---  ---  ---  ---  ---  ---  ---  ---  ---  ---  ---  ---

163                                                                                                     243
1C7       GGA AGT AAT AAA TAC TAT GCA GAC TCC GTG AAG GGC CGA TTC ACC ATC TCC AGA GAC AAT TCC AAG AAC ACG CTG TAT CTG
           ..  ...  ...  ...  ...  ...  ...  ...  ...  ...  ...  ...  ...  ...  ...  ...  ...  ...  ...  ...  ...  ...  ...  ...  ...  ...  ...
VH3-33    GLY SER ASN LYS TYR TYR ALA ASP SER VAL LYS GLY ARG PHE THR ILE SER ARG ASP ASN SER LYS ASN THR LEU TYR LEU
1C7       ---  ---  ---  ---  ---  ---  ---  ---  ---  ---  ---  ---  ---  ---  ---  ---  ---  ---  ---  ---  ---  ---  ---  ---  ---  ---  ---
VH3-33    ---  ---  ---  ---  ---  ---  ---  ---  ---  ---  ---  ---  ---  ---  ---  ---  ---  ---  ---  ---  ---  ---  ---  ---  ---  ---  ---

244                                                                                                     322
1C7       CTG CAA ATG AAC AGC CTG AGA GCC GAG GAC ACG GCT GTG TAT TAC TGT GCG AGA                    GAT CC  A GGG GAT TGT AGT GGT GGT
           ..  ...  ...  ...  ...  ...  ...  ...  ...  ...  ...  ...  ...  ...  ...  ...  ...  ...                    ..   ii  .  T..  ...  ...  ...  ...  ...
VH3-33    LEU GLN MET ASN SER LEU ARG ALA GLU ASP THR ALA VAL TYR TYR CYS ALA ARG                   ASP PRO  GLY ASP CYS SER GLY GLY
1C7       ---  ---  ---  ---  ---  ---  ---  ---  ---  ---  ---  ---  ---  ---  ---  ---  ---  ---                   ASP/GLU II
VH3-33    ---  ---  ---  ---  ---  ---  ---  ---  ---  ---  ---  ---  ---  ---  ---  ---  ---  ---                   ← V gene    D gene →
                                                                                                                          373

323
1C7       AGC TGC TAC TTT .CC AC TAC TTT .. .A GAC TAC TGG GGC CAG GGA ACC CTG GTC ACC GTC TCC TCA
D2-15/JH4  ..  ...  ...  ...  AC  ...  TTT  dd  ddd  GAC TAC TGG GGC CAG  .A  ACC CTG GTC ACC GTC TCC TCA
1C7       SER CYS TYR PHE  dd ddd ASP TYR TRP GLY GLN GLY THR LEU VAL THR VAL SER SER
D2-15/JH4  DD TYR PHE         ---  ---  ASP TYR TRP GLY --- GLY THR LEU VAL THR VAL SER SER
          ← D gene    J gene →                         LYS
```

FIG. 20B

IgV_L2-t 1B4 C-terminal VL domain (1B4: SEQ ID NOS 32, 34; O2/O12: SEQ ID NOS 33, 35)

```
        1                                                                                      81
1B4     GAC ATC CAG TTG ACC CAG TCT CCA TCC TCC CTG CCT GCA TCT GTA GGA GAC AGA GTC ACC ATC ACT TGC CGG GCA AGT CAG
O2/O12  ... A.. ... ... ... ... ... ... ... ... ... T.. ... ... ... ... ... ... ... ... ... ... ... ... ... ... ...
1B4     ASP ILE GLN LEU THR GLN SER PRO SER SER LEU PRO ALA SER VAL GLY ASP ARG VAL THR ILE THR CYS ARG ALA SER GLN
O2/O12  --- --- --- MET --- --- --- --- --- --- --- SER --- --- --- --- --- --- --- --- --- --- --- --- --- --- ---

82                                                                                     162
1B4     AGC ATT AGC AGC TAT TTA AAC TGG TAT CAG CAG AAA CCA GGG AAA GCC CCT AAG CTC CTG ATC TAT GCT GCA TCC AGT TTG
O2/O12  ... ... ... ... ... ... T.. ... ... ... ... ... ... ... ... ... ... ... ... ... ... ... ... ... ... ... ...
1B4     SER ILE SER SER TYR LEU ASN TRP TYR GLN GLN LYS PRO GLY LYS ALA PRO LYS LEU LEU ILE TYR ALA ALA SER SER LEU
O2/O12  --- --- --- --- --- --- --- --- --- --- --- --- --- --- --- --- --- --- --- --- --- --- --- --- --- --- ---

163                                                                                    243
1B4     CAA AGT GGG GTC CCA TCA AGG TTC AGT GGC AGT GGA TCT GGG ACA GAT TTC ACT CTC ACC ATC AGC AGT CTG CAA CCT GAA
O2/O12  ... ... ... ... ... ... ... ... ... ... ... SET ... ... ... ... ... ... ... ... ... ... ... ... ... ... ...
1B4     GLN SER GLY VAL PRO SER ARG PHE SER GLY SER GLY SER GLY THR ASP PHE THR LEU THR ILE SER SER LEU GLN PRO GLU
O2/O12  --- --- --- --- --- --- --- --- --- --- --- --- --- --- --- --- --- --- --- --- --- --- --- --- --- --- ---

244                                                                                    318
1B4            GAT TTT GCA ACT TAC TAC TGT CAA CAA AGT TAC AGT ACC CAC dd d ddd ACG TTC GGC CAA GGG ACC AAG CTG GAA ATC AAA C
O2/O12         ... ... ... ... ... ... ... ... ... ..G ... ..G ..G ..CT CC G TGG D DDD THR ... ... G.. ... ... ... G.. ... ... .
1B4            ASP PHE ALA THR TYR TYR CYS GLN GLN SER TYR SER THR HIS DD D DDD THR PHE GLY GLN GLY THR LYS LEU GLU ILE LYS
O2/O12/JK1     --- --- --- --- --- --- --- --- --- --- GLN --- --- PRO  --- --- --- --- --- --- --- VAL --- --- --- --- ---
                                                             ← V gene │ J gene →
```

Fig. 21B

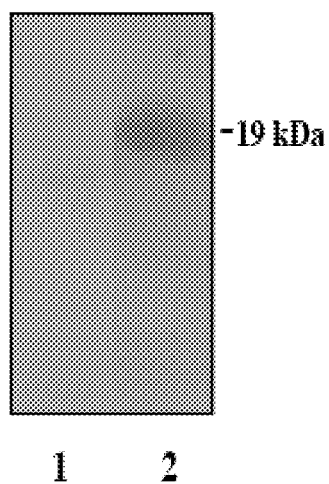
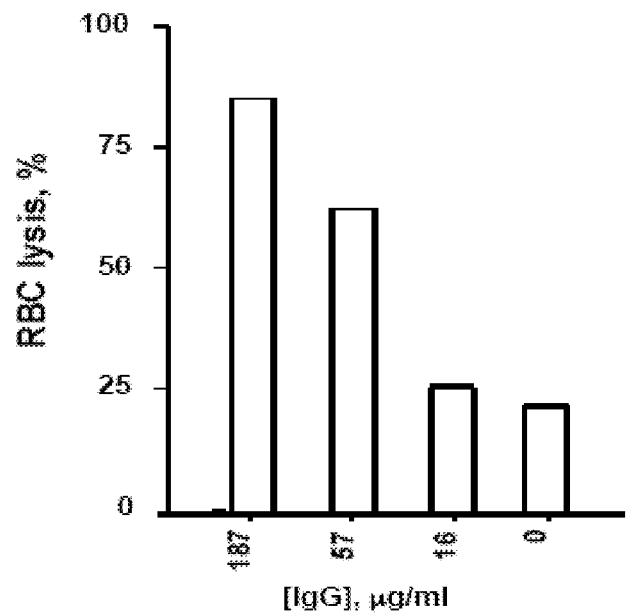
Fig. 22A
Fig. 22B
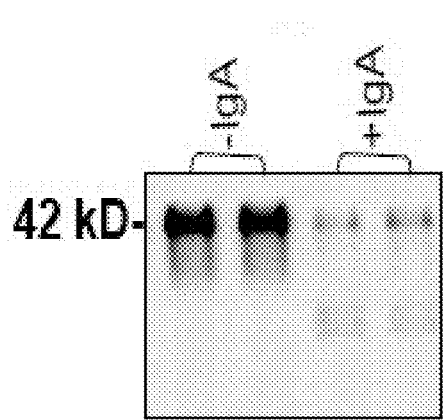
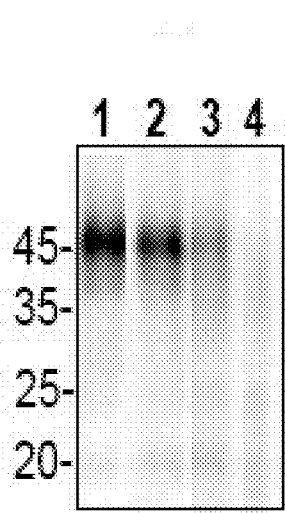
Fig. 23A
Fig. 23B
Fig. 23C

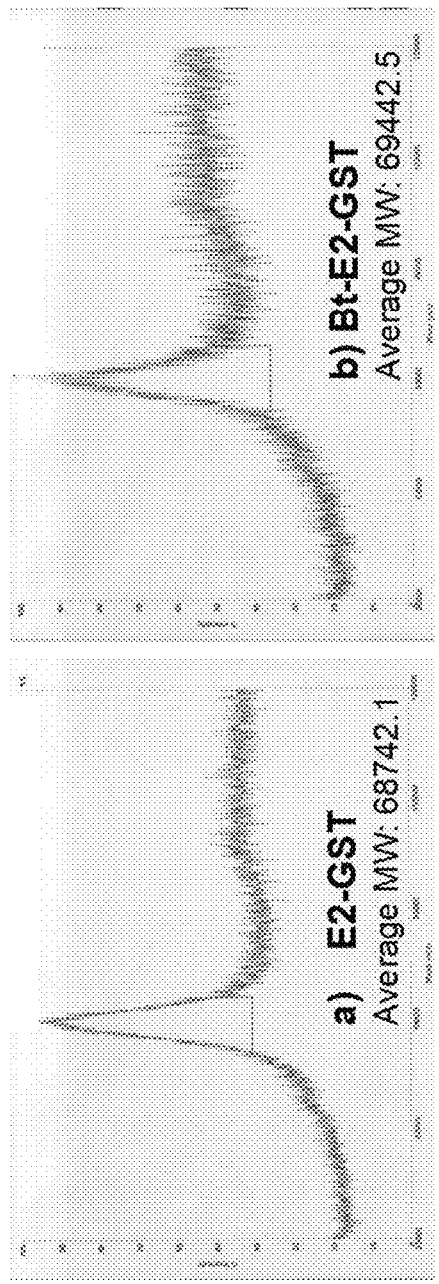
FIG. 29B
FIG. 29A
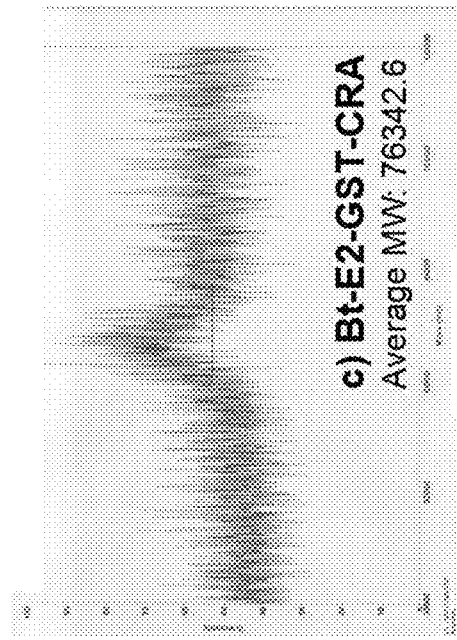
FIG. 29C
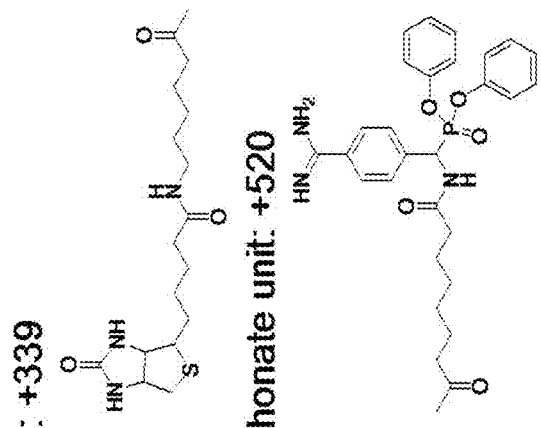
- Bt unit: +339
- Phosphonate unit: +520
FIG. 29D V3, 306-325 (adaptive response):
```
Clade B:  YNKRKRIHIGPGRAFYTTKN    SEQ ID NO 36
97ZA009:  TR.SM..--...QV..A.NG    SEQ ID NO 37
```

C4, 421-433 (superantigenic site):
```
Clade B:  KQIINMWQEVGKA    SEQ ID NO 38
97ZA009:  ...........R.    SEQ ID NO 39
```

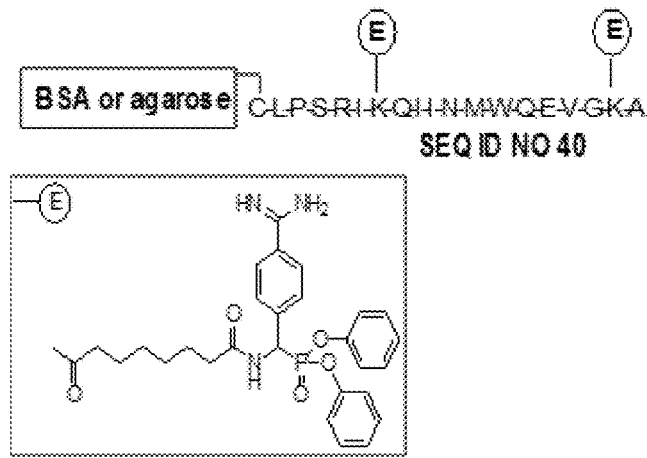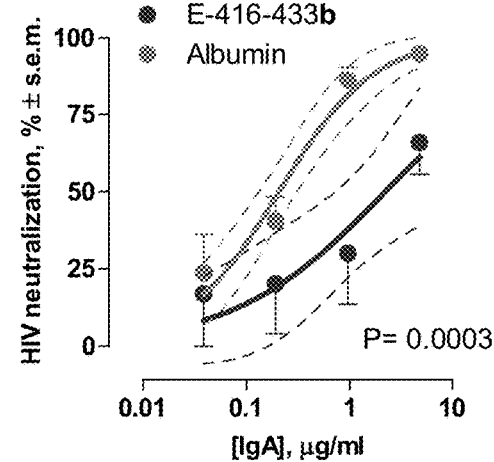
FIG. 33A  FIG. 33B
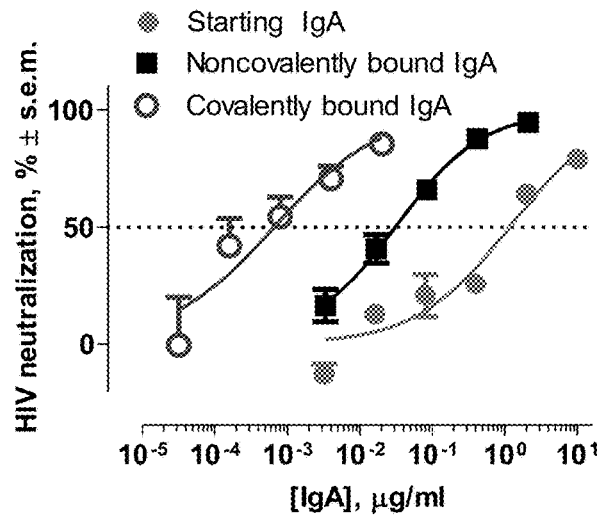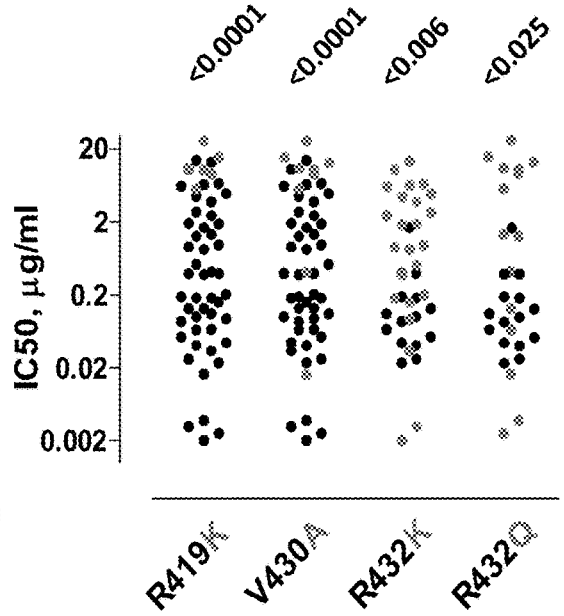
FIG. 33C  FIG. 33D

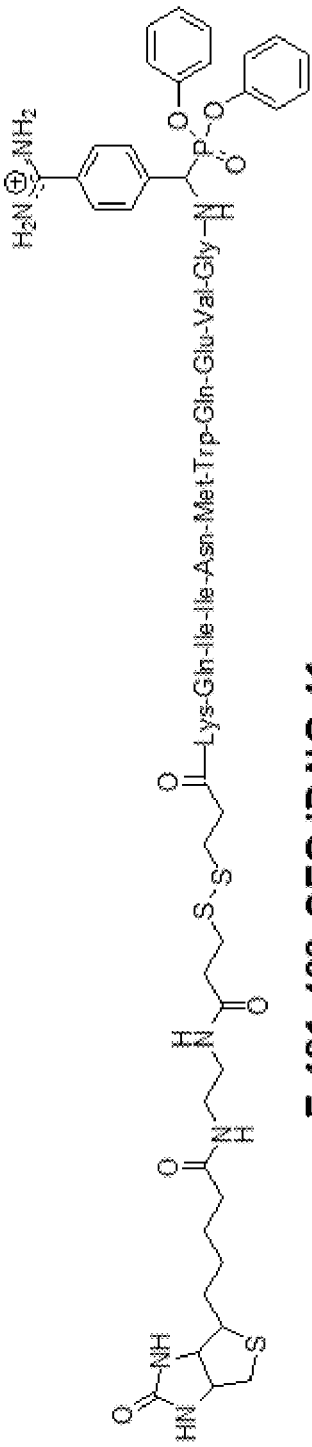
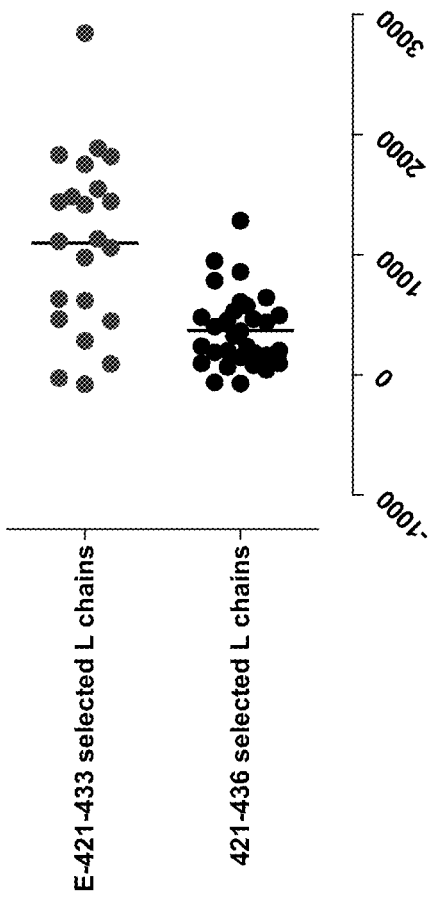
E-421-433 SEQ ID NO 41
Lys-Gln-Ile-Ile-Asn-Met-Trp-Gln-Glu-Val-Gly-Lys-Ala-Met-Tyr-Ala
421-436 SEQ ID NO 42
FIG. 34A
FIG. 34B Light chain SK18 VL domain SEQ ID No 43

1
ASP ILE GLN MET THR GLN SER PRO SER SER LEU SER ALA SER VAL GLY ASP ARG VAL THR
21
VAL THR CYS ARG ALA SER GLN SER ILE SER SER TYR LEU ASN TRP TYR GLN GLN GLN PRO
41
GLY LYS ALA PRO LYS LEU LEU ILE TYR ALA ALA SER SER LEU GLN SER GLY VAL PRO SER
61
ARG PHE SER GLY SER GLY SER GLY THR ASP PHE THR LEU THR ILE SER SER LEU GLN PRO
81
GLU ASP PHE ALA THR TYR PHE CYS GLN GLN SER TYR SER ILE PRO ARG THR PHE GLY GLN
101
GLY THR LYS VAL GLU ILE LYS

FIG. 35A

Light chain SK45 VL domain SEQ ID No 44

1
ASP ILE GLN MET THR GLN SER PRO SER SER LEU SER ALA SER VAL GLY ASP ARG VAL THR
21
ILE THR CYS ARG ALA SER GLN GLY ILE ARG ASN ASP LEU GLY TRP TYR GLN GLN LYS PRO
41
GLY LYS ALA PRO LYS ALA LEU ILE TYR ALA ALA SER SER LEU GLN SER GLY VAL PRO SER
61
ARG PHE SER GLY SER GLY SER GLY THR GLU PHE THR LEU THR ILE SER SER LEU GLN PRO
81
GLU ASP PHE ALA THR TYR TYR CYS LEU GLN HIS ASN SER TYR PRO LEU THR PHE GLY GLY
101
GLY THR LYS VAL GLU ILE LYS

FIG. 35B

Light chain SKL6 VL domain SEQ ID No 45

1
ASP ILE GLN MET THR GLN SER PRO SER SER LEU SER ALA SER VAL GLY ASP GLY VAL THR
21
ILE THR CYS ARG ALA SER GLN SER ILE SER SER TYR LEU HIS TRP TYR GLN GLN LYS PRO
41
GLY LYS ALA PRO LYS LEU LEU ILE TYR VAL ALA SER SER LEU GLN SER GLY VAL PRO SER
61
ARG PHE SER GLY SER GLY SER GLY THR ASP PHE THR LEU THR ILE SER SER LEU GLN PRO
81
GLU ASP PHE ALA THR TYR TYR CYS GLN GLN SER TYR SER THR PRO ILE THR PHE GLY GLN
101
GLY THR ARG LEU GLU ILE LYS

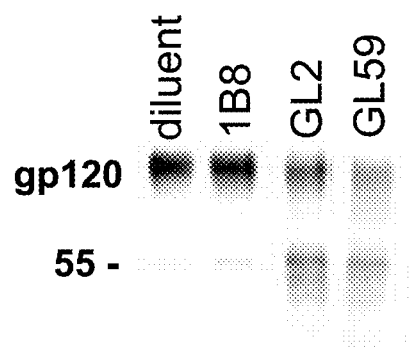
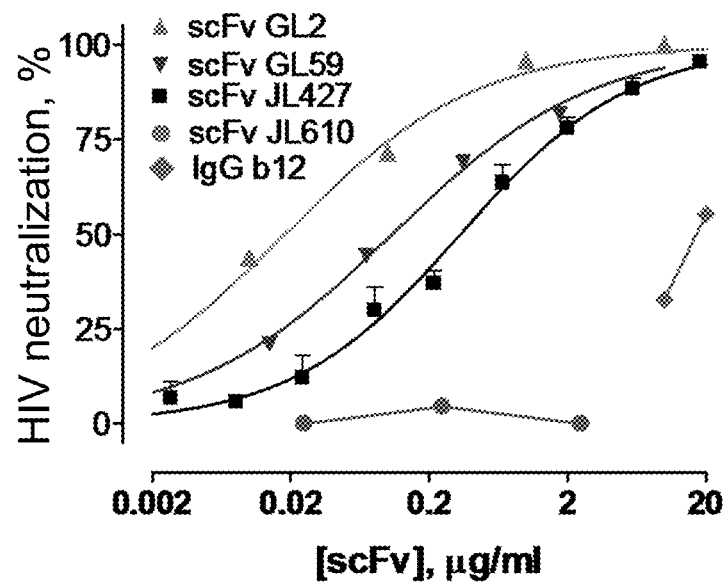
FIG. 37A
FIG. 37B
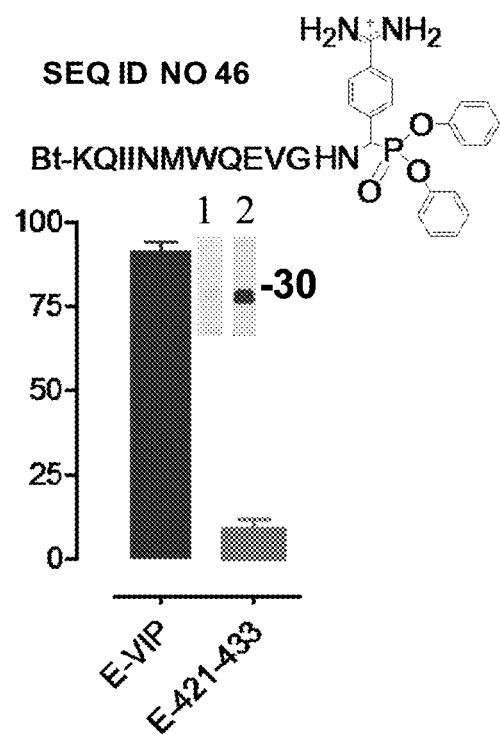
FIG. 37C scFv-t

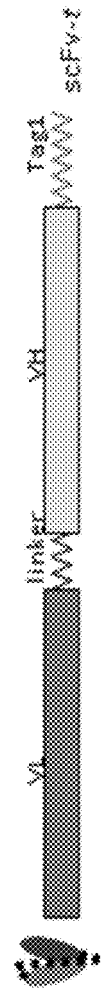

CLONE GL2
VL: ETTLTQSPATLSLSPGERATLSCRASQSVSSYLAWYQQKPGQAPRLLIYDASNRATGIPARFSGSGSGTDFTLTISSLEPEDFAVYYCQQRSNWPLTFGGG
TKLEIKR (SEQ ID NO 47)
Linker: SSGGGGSGGGGSGGGSA (SEQ ID NO 57)
VH: LQVQLQQSGPRLVKPSGTLSLTCTVSGGSISSSSYYWGWIRQHPGKGLEWIGYIYYSGSTYYNPSLKSRVTISVDTSKNQFSLKLSSVTAADTAVYYCARL
QGARGYSYGYGIDYWGQGTLVTVSSGSASAPTLFP (SEQ ID NO 48)
Tag (t): AAAHHHHHHGAAEQKLISEEDLNGAA (SEQ ID NO 58)

CLONE JL427
VL: QSVLTQPPSVSGAPGQRVTISCSGSSSNFGLNYVWYQHFPGTAPKLLIYRNDQRPLGVPARFSGSKSGTSASLAISGLRSEDEADYYCQSYDNSLSGWVF
GGGTQLTVLG (SEQ ID NO 49)
Linker: SSGGGGSGGGGSGGGSA (SEQ ID NO 57)
VH: LQVQLQQSGGGLVQPGRSLRLSCAASGFTFSSYGMHWVRQAPGKGLEWVSYIGRSGSHTNYADSVKGRFTISRDNSKNTLYLQINSLRAEDTAVYYCARGL
PNYGMDIWGQGTTVTVSSGSASAPTLFP (SEQ ID NO 50)
Tag (t): AAAHHHHHHGAAEQKLISEEDLNGAA (SEQ ID NO 58)

CLONE JL606
VL: ETTLTQSPGILSLSPGERATLSCRASQRVSSYYLAWYQQKPGQAPRLLIYGASTRATGIPDRFSGSGSGTDFTLTITTRLEPEDFAVYYCQQYSSSRSTFGQGT
KVEIKR (SEQ ID NO 51)
Linker: SSGGGGSGGGGSGGGSA (SEQ ID NO 57)
VH: LQVQLQESGPGLVKPSETLSLTCTVSGGSISSYYWSWIRQPAGKGLEWIGRIYTSGSTNYNPSLKSRVTMSVDTSKNQFSLKLSSVTAADTAVYYCARHQRDI
VVVPALDVWGKGTTVTVSSGSASAPTLFP (SEQ ID NO 52)
Tag (t): AAAHHHHHHGAAEQKLISEEDLNGAA (SEQ ID NO 58)

Fig. 38A scFv-t

CLONE GL59

VL: SYVLTQPPSVSVAPGQTARITCGGYNIGSSSVHWYQQKSGQAPVLVVYDDSDRPSGIPERFSGSNSGTTATLTISRVEAGDEAD
YYCQVWDRGSDSYVFGTGTEVTVL (SEQ ID NO 53)

Linker: SSGGGGSGGGGSGGSA (SEQ ID NO 57)

VH: LQVQLVQSGAEVKKPGSSVKVSCKASGGAFSNYLITWVRQAPGQGLEYLGRITIPILQKSSYAQKFEGRVTFTADKSTSTAYMEL
TRLTSDDTAVFYCAAVRIVPVPSLPPGSFFYWGLGTVVTVSSASTKGPSVFP (SEQ ID NO 54)

Tag (t): AAAHHHHHHGAAEQKLISEEDLNGAA (SEQ ID NO 58)

CLONE JL678

VL: QAVLTQPSSASGTPGRRVTISCSGSSSNIGSNTVNWYQQLPGTAPKLLIYSNNQWPSGVPDRFSGSKSGTSASLAISGLQSEDE
ADYYCAAWDDSLNGPVFGGGTQLTVLG (SEQ ID NO 55)

Linker: SSGGGGSGGGGSGGSA (SEQ ID NO 57)

VH: LQVQLQQSGSGLVKPSQTLSLTCTVSGGSVSIESGASYWSWIRQPRPGNGLEWIGYISYSGSTNYNPSLKSRVFISGDTSKNQFSLR
LSSVTAADTAIYYCARRPRTGRFDSWGQGALVIVSSASTKGPSVFP (SEQ ID NO 56)

Tag (t): AAAHHHHHHGAAEQKLISEEDLNGAA (SEQ ID NO 58)

Fig. 38B

IgV$_{L2}$-t

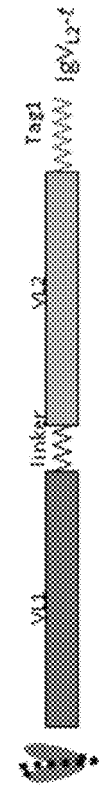

CLONE GL1

VL1: QSVLTQPPSVSAAPGQMVTISCSGSSSNIKDNIVSWYQKFPGTAPKLLIYDNERRPSGIPDRFSGSKSG
TSATLGITGLQTGDEADYYCGTWDNSLSFWVFGGGTKVTVL (SEQ ID NO 59)

Linker: SSGGGSGGGGSGGSA (SEQ ID NO 57)

VL2: LDIQLTQSPSSLPASVGDRVTITCRASQSISSYLNWYQQKPGKAPKLLIYAASSLQSGVPSRFSGSGSG
TDFTLTISSLQPEDFATYYCQQSYSTHTFGQGTKLEIKR (SEQ ID NO 69)

Tag (t): AAAHHHHHHGAAEQKLISEEDLNGAA (SEQ ID NO 58)

Fig. 38C

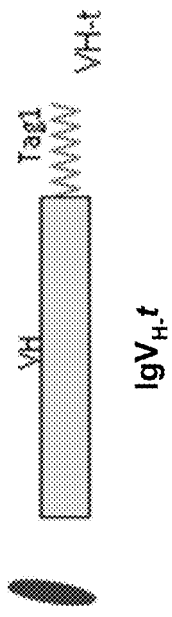

CLONE JL683
VH:QVQLQESGPGLVKPSETLSLTCAVSGYSISSGYYWGWIRQPPGKGLEWIGEIYHSGSTNYNPSLKSRVTISVDKSKNQFSLKLSSVTAADTAVYYC
ASRLGYWGQGTLVTVSSGSASAPTLFP (SEQ ID NO 60)
Tag (t): AAAHHHHHHGAAEQKLISEEDLNGAA (SEQ ID NO 58)

Fig. 38D

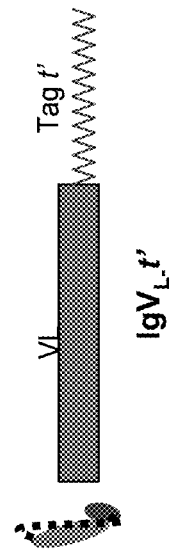

CLONE JL651
VL:SYVLTQPPSVSVSPGQPASITCSGDKLGDKYACWYQQKPGRSPVLVIYEDNKRPSGIPERLSGSNSGNTATLTISGTQALDEADYCQAWDSSTVV
FGGGTKVTVLG (SEQ ID NO 61)
Tag(t'):SSGGGGSGGGGSGGGGSA*LQVQLQQSGQTKGPSVFP*AAAHHHHHHGAAEQKLISEEDLNGAA (SEQ ID NO 62)

| FR1 | CDR1 | FR2 | CDR2 | FR3 | CDR3 |

GL2 VH

LQVQLQQSGPRLVKPSGTLSLTCTVSGGSISSSSYYWGWIRQ
HPGKGLEWIGYIYYSGSTYYNPSLKSRVTISVDTSKNQFSLK
LSSVTAADTAVYYCARLQGARGYSYGYGIDYWGQGTLVTVSS
GSASAPTLFP (SEQ ID NO 63)

JL427 VH (VH3)

| FR1 | CDR1 | FR2 | CDR2 | FR3 | CDR3 |

JL427 VH

LQVQLVESGGGLVQPGRSLRLSCAASGFTFSSYGMHWVRQAP
GKGLEWVSYIGRSGSHTNYADSVKGRFTISRDNSKNTLYLQI
NSLRAEDTAVYYCARGLPNYGMDIWGQGTTVTVSSGSASAPT
LFP (SEQ ID NO 66)

GL2-FR1m VH

| FR1 | CDR1 | FR2 | CDR2 | FR3 | CDR3 |

GL2-FR1m VH

LQVQLQQSGGGLVQPGRSLRLSCAASGFTFSSSSYYWGWIRQ
HPGKGLEWIGYIYYSGSTYYNPSLKSRVTISVDTSKNQFSLK
LSSVTAADTAVYYCARLQGARGYSYGYGIDYWGQGTLVTVSS
GSASAPTLFPAAAHHHHHGAAEQKLISEEDLNGAA
(SEQ ID NO 64)

GL2-CDR1m VH

| FR1 | CDR1 | FR2 | CDR2 | FR3 | CDR3 |

GL2-CDR1m VH

LQVQLQQSGPRLVKPSGTLSLTCTVSGGSISSSSYGMHWIRQHP
GKGLEWIGYIYYSGSTYYNPSLKSRVTISVDTSKNQFSLKLS
SVTAADTAVYYCARLQGARGYSYGYGIDYWGQGTLVTVSSGS
ASAPTLFPAAAHHHHHGAAEQKLISEEDLNGAA
(SEQ ID NO 67)

GL2-FR3m VH

| FR1 | CDR1 | FR2 | CDR2 | FR3 | CDR3 |

GL2-FR3m VH

LQVQLQQSGPRLVKPSGTLSLTCTVSGGSISSSSYYWGWIRQ
HPGKGLEWIGYIYYSGSTYYNPSLKS**RFTISRDNSKNTLYLQ
INSLRAEDTAVYYCAR**LQGARGYSYGYGIDYWGQGTLVTVSS
GSASAPTLFPAAAHHHHHGAAEQKLISEEDLNGAA
(SEQ ID NO 65)

GL2-CDR2m VH

| FR1 | CDR1 | FR2 | CDR2 | FR3 | CDR3 |

GL2-CDR2m VH

LQVQLQQSGPRLVKPSGTLSLTCTVSGGSISSSSYYWGWIRQ
HPGKGLEWIGYIGRSGSHTNYADSVKGRVTISVDTSKNQFSL
KLSSVTAADTAVYYCARLQGARGYSYGYGIDYWGQGTLVTVS
SGSASAPTLFPAAAHHHHHGAAEQKLISEEDLNGAA
(SEQ ID NO 68)

Fig. 39

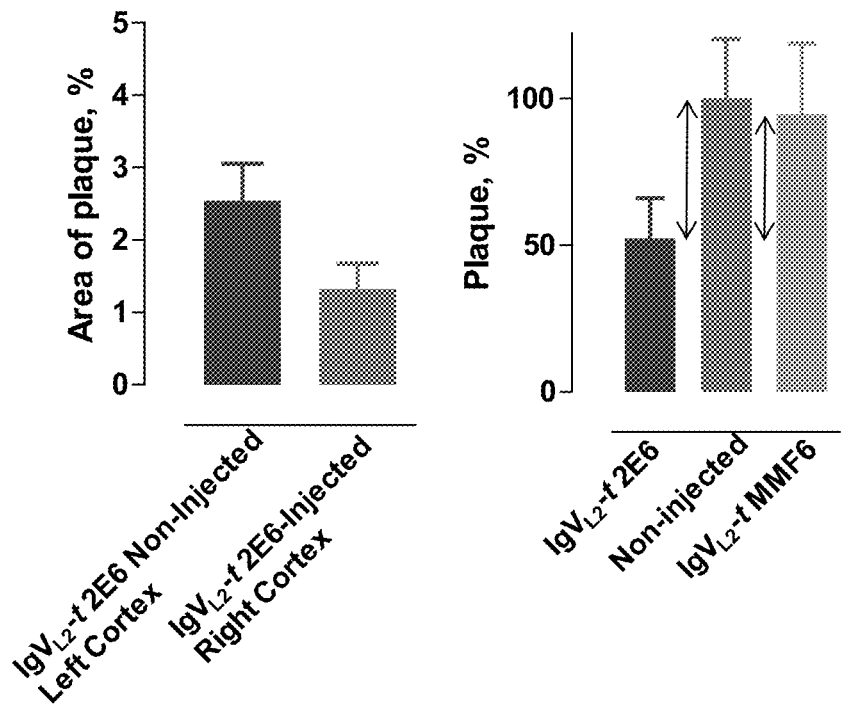
FIG. 42A  FIG. 42B
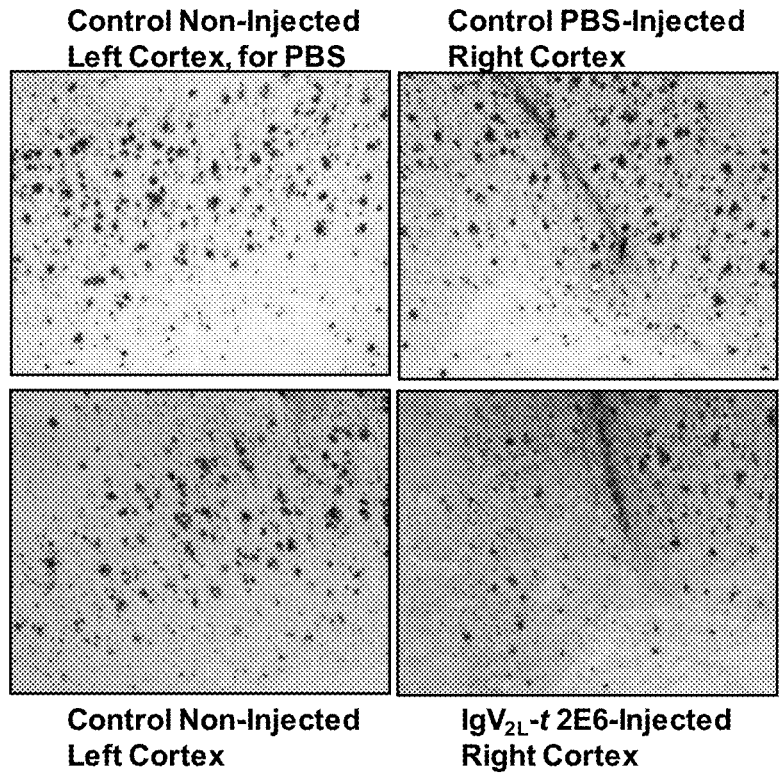
FIG. 42C

SEQUENCE LISTING

```
<160> NUMBER OF SEQ ID NOS: 69

<210> SEQ ID NO 1
<211> LENGTH: 33
<212> TYPE: DNA
<213> ORGANISM: artificial sequence
<220> FEATURE:
<223> OTHER INFORMATION: reverse primer used in VH amplification

<400> SEQUENCE: 1
ggtagtgcac ttcaggtgca gctgttgcag tct                                 33

<210> SEQ ID NO 2
<211> LENGTH: 35
<212> TYPE: DNA
<213> ORGANISM: artificial sequence
<220> FEATURE:
<223> OTHER INFORMATION: forward primer used in VH amplification

<400> SEQUENCE: 2
atgtgcggcc gcggggaaaa gggttggggg catgc                               35

<210> SEQ ID NO 3
<211> LENGTH: 29
<212> TYPE: DNA
<213> ORGANISM: artificial sequence
<220> FEATURE:
<223> OTHER INFORMATION: NcoI primer used in VL amplification

<400> SEQUENCE: 3
taagatctca gtctgccctg actcagcct                                      29

<210> SEQ ID NO 4
<211> LENGTH: 31
<212> TYPE: DNA
```

```
<213> ORGANISM: artificial sequence
<220> FEATURE:
<223> OTHER INFORMATION: XhoI primer used in VL amplification

<400> SEQUENCE: 4
tagcggccgc gggctgacct aaaacggtga g                              31

<210> SEQ ID NO 5
<211> LENGTH: 25
<212> TYPE: DNA
<213> ORGANISM: artificial sequence
<220> FEATURE:
<223> OTHER INFORMATION: ApaL1 primer used in VL amplification

<400> SEQUENCE: 5
tagaattcca gttgacccag tctcc                                     25

<210> SEQ ID NO 6
<211> LENGTH: 28
<212> TYPE: DNA
<213> ORGANISM: artificial sequence
<220> FEATURE:
<223> OTHER INFORMATION: NotI primer used in VL amplification

<400> SEQUENCE: 6
taaagcttgc acgtttgatt tccagctt                                  28

<210> SEQ ID NO 7
<211> LENGTH: 40
<212> TYPE: PRT
<213> ORGANISM: artificial sequence
<220> FEATURE:
<223> OTHER INFORMATION: amyloid beta 40 analog peptide
<220> FEATURE:
<221> NAME/KEY: MISC_FEATURE
<222> LOCATION: 16, 28
<223> OTHER INFORMATION: Xaa is any amino acid

<400> SEQUENCE: 7

Asp Ala Glu Phe Arg His Asp Ser Gly Tyr Glu Val His His Gln
1               5                   10                  15

Xaa Leu Val Phe Phe Ala Glu Asp Val Gly Ser Asn Xaa Gly Ala
                20                  25                  30

Ile Ile Gly Leu Met Val Gly Gly Val Val
                35                  40

<210> SEQ ID NO 8
<211> LENGTH: 262
<212> TYPE: PRT
<213> ORGANISM: artificial sequence
<220> FEATURE:
<223> OTHER INFORMATION: IgVL2-t 2E6 amino acid sequence

<400> SEQUENCE: 8

Gln Ser Ala Leu Thr Gln Pro Ala Ser Val Ser Gly Ser Pro Gly
1               5                   10                  15

Gln Ser Ile Thr Ile Ser Cys Thr Gly Thr Ser Ser Asp Val Gly
                20                  25                  30

Gly Tyr Asn Tyr Val Ser Trp Tyr Gln Gln His Pro Gly Lys Ala
                35                  40                  45

Pro Lys Leu Met Ile Ser Glu Val Ser Asn Arg Pro Ser Gly Val
                50                  55                  60

Ser Asn Arg Phe Ser Gly Ser Lys Ser Gly Asn Thr Ala Ser Leu
                65                  70                  75
```

```
Thr Ile Ser Gly Pro Gln Thr Glu Asp Glu Ala Asp Tyr Tyr Cys
            80                  85                  90

Ser Ser Tyr Thr Ser Ser Thr Pro Val Val Phe Gly Gly Gly
            95                  100                 105

Thr Gln Leu Thr Val Leu Gly Ser Ser Gly Gly Gly Ser Gly
            110                 115                 120

Gly Gly Gly Ser Gly Gly Ser Ala Leu Asp Ile Gln Leu Thr Gln
            125                 130                 135

Ser Pro Ser Ser Leu Pro Ala Ser Val Gly Asp Arg Val Thr Ile
            140                 145                 150

Thr Cys Arg Ala Ser Gln Ser Ile Ser Ser Tyr Leu Asn Trp Tyr
            155                 160                 165

Gln Gln Lys Pro Gly Lys Ala Pro Lys Leu Leu Ile Tyr Ala Ala
            170                 175                 180

Ser Ser Leu Gln Ser Gly Val Pro Ser Arg Phe Ser Gly Ser Gly
            185                 190                 195

Ser Gly Thr Asp Phe Thr Leu Thr Ile Ser Ser Leu Gln Pro Glu
            200                 205                 210

Asp Phe Ala Thr Tyr Tyr Cys Gln Gln Ser Tyr Ser Thr His Thr
            215                 220                 225

Phe Gly Gln Gly Thr Lys Leu Glu Ile Lys Arg Ala Ala Ala His
            230                 235                 240

His His His His His Gly Ala Ala Glu Gln Lys Leu Ile Ser Glu
            245                 250                 255

Glu Asp Leu Asn Gly Ala Ala
            260

<210> SEQ ID NO 9
<211> LENGTH: 168
<212> TYPE: PRT
<213> ORGANISM: artificial sequence
<220> FEATURE:
<223> OTHER INFORMATION: IgVL2-t 5D3 amino acid sequence

<400> SEQUENCE: 9

Glu Ile Val Leu Thr Gln Ser Pro Gly Thr Leu Ser Leu Ser Pro
1               5                   10                  15

Gly Glu Arg Ala Thr Leu Ser Cys Arg Ala Ser Gln Ser Val Gly
            20                  25                  30

Gly Ser Tyr Leu Ala Trp Tyr Gln Gln Lys Pro Gly Gln Ala Pro
            35                  40                  45

Arg Leu Leu Ile Tyr Gly Ala Ser Ser Arg Ala Thr Gly Ile Pro
            50                  55                  60

Asp Arg Phe Ser Gly Ser Gly Ser Gly Thr Asp Phe Thr Leu Thr
            65                  70                  75

Ile Ser Arg Leu Glu Pro Glu Asp Phe Ala Val Tyr Tyr Cys Gln
            80                  85                  90

Leu Tyr Gly Gly Ser Pro Met Tyr Thr Phe Gly Gln Gly Thr Lys
            95                  100                 105

Leu Glu Ile Lys Arg Ser Ser Gly Gly Gly Ser Gly Gly Gly
            110                 115                 120

Gly Ser Gly Gly Ser Ala Leu Gln Val Gln Leu Leu Gln Ser Ala
            125                 130                 135

Cys Ala Pro Thr Leu Phe Pro Ala Ala Ala His His His His
            140                 145                 150
```

His Gly Ala Ala Glu Gln Lys Leu Ile Ser Glu Glu Asp Leu Asn
            155                 160                 165

Gly Ala Ala

<210> SEQ ID NO 10
<211> LENGTH: 182
<212> TYPE: PRT
<213> ORGANISM: artificial sequence
<220> FEATURE:
<223> OTHER INFORMATION: IgVL2-t 1E4 amino acid sequence

<400> SEQUENCE: 10

Gln Ser Val Leu Thr Gln Pro Pro Ser Val Ser Ala Ala Pro Gly
1               5                   10                  15

Gln Lys Val Thr Ile Ser Cys Ser Gly Ser Ser Ser Asn Ile Gly
                20                  25                  30

Asn Asn Tyr Val Ser Trp Tyr Gln Gln Leu Pro Gly Thr Ala Pro
                35                  40                  45

Lys Leu Leu Ile Tyr Asp Asn Glu Arg Arg Pro Ser Gly Ile Pro
                50                  55                  60

Asp Arg Phe Ser Gly Ser Lys Ser Gly Thr Ser Ala Thr Leu Ala
                65                  70                  75

Ile Thr Gly Leu Gln Pro Gly Asp Glu Ala Asp Tyr Tyr Cys Ala
                80                  85                  90

Ala Trp Asp Asn Thr Leu Arg Gly Gly Val Phe Gly Gly Gly Thr
                95                  100                 105

Gln Leu Thr Val Leu Gly Ser Ser Gly Gly Gly Ser Gly Gly
                110                 115                 120

Gly Gly Ser Gly Gly Ser Ala Leu Gln Val Gln Leu Gln Glu Ser
                125                 130                 135

Gly Ala Gly Glu Glu Arg Gly Arg Val Trp Cys Thr His Thr Lys
                140                 145                 150

Gly Pro Ser Val Phe Pro Ala Ala Ala His His His His His
                155                 160                 165

Gly Ala Ala Glu Gln Lys Leu Ile Ser Glu Glu Asp Leu Asn Gly
                170                 175                 180

Ala Ala

<210> SEQ ID NO 11
<211> LENGTH: 172
<212> TYPE: PRT
<213> ORGANISM: artificial sequence
<220> FEATURE:
<223> OTHER INFORMATION: IgVL2-t 5H3 amino acid sequence

<400> SEQUENCE: 11

Gln Ser Val Leu Thr Gln Pro Pro Ser Val Ser Gly Ala Pro Gly
1               5                   10                  15

Gln Arg Val Thr Ile Ser Cys Thr Gly Ser Ser Ser Asn Ile Gly
                20                  25                  30

Ala Gly Tyr Asp Val His Trp Tyr Gln Gln Leu Pro Gly Thr Ala
                35                  40                  45

Pro Lys Leu Leu Ile Tyr Gly Asn Ser Asn Arg Pro Ser Gly Val
                50                  55                  60

Pro Asp Arg Phe Ser Gly Ser Lys Ser Gly Thr Ser Ala Ser Leu
                65                  70                  75

```
Ala Ile Thr Gly Leu Gln Ala Glu Asp Ala Asp Tyr Tyr Cys
                80                  85                  90

Gln Ser Tyr Asp Ser Ser Leu Ser Gly Val Val Phe Gly Gly
            95                 100                 105

Thr Gln Leu Thr Val Leu Gly Ser Ser Gly Gly Gly Ser Gly
        110                 115                 120

Gly Gly Gly Ser Gly Gly Ser Ala Leu Gln Val Ser Cys Val
            125                 130                 135

Gly Ser His Ala Ser Ala Pro Thr Leu Phe Pro Ala Ala His
        140                 145                 150

His His His His His Gly Ala Ala Glu Gln Lys Leu Ile Ser Glu
            155                 160                 165

Glu Asp Leu Asn Gly Ala Ala
                170

<210> SEQ ID NO 12
<211> LENGTH: 154
<212> TYPE: PRT
<213> ORGANISM: Artificial sequence
<220> FEATURE:
<223> OTHER INFORMATION: VH 5D3-D4 derivative VH domain sequence, from
      mutant IgVL-t 5D3

<400> SEQUENCE: 12

Gln Val Gln Leu Leu Gln Ser Gly Ala Glu Val Lys Lys Pro Gly
1               5                   10                  15

Ala Ser Val Lys Val Ser Cys Lys Ala Ser Gly Tyr Thr Phe Thr
            20                  25                  30

Gly Tyr Tyr Met His Trp Val Arg Gln Ala Pro Gly Gln Gly Leu
        35                  40                  45

Glu Trp Met Gly Trp Ile Asn Pro Asn Ser Gly Gly Thr Asn Tyr
    50                  55                  60

Ala Gln Lys Phe Gln Gly Arg Val Thr Met Thr Arg Asp Thr Ser
            65                  70                  75

Ile Ser Thr Ala Tyr Met Glu Leu Ser Arg Leu Arg Ser Asp Asp
        80                  85                  90

Thr Ala Val Tyr Tyr Cys Ala Arg Trp Ser His Ser Ser Gly Leu
        95                 100                 105

Asp Tyr Trp Gly Gln Gly Thr Leu Val Thr Val Ser Ser Gly Ser
        110                 115                 120

Ala Cys Ala Pro Thr Leu Phe Pro Ala Ala His His His
        125                 130                 135

His His Gly Ala Ala Glu Gln Lys Leu Ile Ser Glu Glu Asp Leu
        140                 145                 150

Asn Gly Ala Ala

<210> SEQ ID NO 13
<211> LENGTH: 151
<212> TYPE: PRT
<213> ORGANISM: Artificial sequence
<220> FEATURE:
<223> OTHER INFORMATION: VH 5D3-D10 derivative VH domain sequence, from
      mutant IgVL-t 5D3

<400> SEQUENCE: 13

Gln Val Gln Leu Leu Gln Ser Gly Ala Glu Val Lys Lys Pro Gly
1               5                   10                  15

Ala Ser Val Lys Val Ser Cys Lys Ala Ser Gly Tyr Thr Phe Thr
```

```
                        20                  25                  30

Ser Tyr Asp Ile Asn Trp Val Arg Gln Ala Thr Gly Gln Gly Leu
                    35                  40                  45

Glu Trp Met Gly Trp Met Asn Pro Asn Ser Gly Asn Thr Gly Tyr
                50                  55                  60

Ala Gln Lys Phe Gln Gly Arg Val Thr Met Thr Arg Asn Thr Ser
            65                  70                  75

Ile Ser Thr Ala Tyr Met Glu Leu Ser Ser Leu Arg Ser Glu Gly
        80                  85                  90

Thr Ala Val Tyr Tyr Cys Ala Thr Gly Ser Arg Tyr Asp Tyr Trp
        95                  100                 105

Gly Gln Gly Thr Leu Val Thr Val Ser Ser Gly Ser Ala Cys Ala
            110                 115                 120

Pro Thr Leu Phe Pro Ala Ala Ala His His His His His His Gly
            125                 130                 135

Ala Ala Glu Gln Lys Leu Ile Ser Glu Glu Asp Leu Asn Gly Ala
            140                 145                 150

Ala

<210> SEQ ID NO 14
<211> LENGTH: 155
<212> TYPE: PRT
<213> ORGANISM: Artificial sequence
<220> FEATURE:
<223> OTHER INFORMATION: VH 5D3-E4 derivative VH domain sequence, from
      mutant IgVL-t 5D3

<400> SEQUENCE: 14

Gln Val Gln Leu Leu Gln Ser Gly Pro Gly Leu Val Lys Pro Ser
1               5                   10                  15

Glu Thr Leu Ser Leu Thr Cys Thr Val Ser Gly Gly Ser Ile Ser
                20                  25                  30

Ser Gly Ser Tyr Tyr Trp Ser Trp Ile Arg Gln Pro Ala Gly Lys
                35                  40                  45

Gly Leu Glu Trp Ile Gly Arg Ile Tyr Thr Ser Gly Ser Thr Asn
            50                  55                  60

Tyr Asn Pro Ser Leu Lys Ser Arg Val Thr Ile Ser Val Asp Thr
            65                  70                  75

Ser Lys Asn Gln Phe Ser Leu Lys Leu Ser Ser Val Thr Ala Ala
        80                  85                  90

Asp Thr Ala Val Tyr Tyr Cys Ala Arg Val Gly Arg Leu Asn Trp
        95                  100                 105

Phe Asp Pro Trp Gly Gln Gly Thr Leu Val Thr Val Ser Ser Gly
            110                 115                 120

Ser Ala Cys Ala Pro Thr Leu Phe Pro Ala Ala Ala His His His
            125                 130                 135

His His His Gly Ala Ala Glu Gln Lys Leu Ile Ser Glu Glu Asp
            140                 145                 150

Leu Asn Gly Ala Ala
            155

<210> SEQ ID NO 15
<211> LENGTH: 156
<212> TYPE: PRT
<213> ORGANISM: Artificial sequence
<220> FEATURE:
<223> OTHER INFORMATION: VH 5D3-E6 derivative VH domain sequence, from
``` mutant IgVL-t 5D3

<400> SEQUENCE: 15

Gln Val Gln Leu Leu Gln Ser Gly Pro Gly Leu Val Lys Pro Ser
1               5                   10                  15

Glu Thr Leu Ser Leu Thr Cys Thr Val Ser Gly Gly Ser Ile Ser
            20                  25                  30

Ser Gly Gly Tyr Tyr Trp Ser Trp Ile Arg Gln His Pro Gly Lys
        35                  40                  45

Gly Leu Glu Trp Ile Gly Tyr Ile Tyr Tyr Ser Gly Ser Thr Tyr
    50                  55                  60

Tyr Asn Pro Ser Leu Lys Ser Arg Val Thr Ile Ser Val Asp Thr
65                  70                  75

Ser Lys Asn Gln Phe Ser Leu Lys Leu Ser Ser Val Thr Ala Ala
            80                  85                  90

Asp Thr Ala Val Tyr Tyr Cys Ala Arg Ala Gly Asp Ser Ser Gly
        95                  100                 105

Pro Gly Asp Tyr Trp Gly Gln Gly Thr Leu Val Thr Val Ser Ser
    110                 115                 120

Gly Ser Ala Cys Ala Pro Thr Leu Phe Pro Ala Ala Ala His His
125                 130                 135

His His His His Gly Ala Ala Glu Gln Lys Leu Ile Ser Glu Glu
            140                 145                 150

Asp Leu Asn Gly Ala Ala
            155

<210> SEQ ID NO 16
<211> LENGTH: 242
<212> TYPE: PRT
<213> ORGANISM: Artificial sequence
<220> FEATURE:
<223> OTHER INFORMATION: full length L-t 5D3 sequence from mutant IgVL-t
      5D3

<400> SEQUENCE: 16

Glu Ile Val Leu Thr Gln Ser Pro Gly Thr Leu Ser Leu Ser Pro
1               5                   10                  15

Gly Glu Arg Ala Thr Leu Ser Cys Arg Ala Ser Gln Ser Val Gly
            20                  25                  30

Gly Ser Tyr Leu Ala Trp Tyr Gln Gln Lys Pro Gly Gln Ala Pro
        35                  40                  45

Arg Leu Leu Ile Tyr Gly Ala Ser Ser Arg Ala Thr Gly Ile Pro
    50                  55                  60

Asp Arg Phe Ser Gly Ser Gly Ser Gly Thr Asp Phe Thr Leu Thr
65                  70                  75

Ile Ser Arg Leu Glu Pro Glu Asp Phe Ala Val Tyr Tyr Cys Gln
            80                  85                  90

Leu Tyr Gly Gly Ser Pro Met Tyr Thr Phe Gly Gln Gly Thr Lys
        95                  100                 105

Leu Glu Ile Lys Arg Thr Val Ala Ala Pro Ser Val Phe Ile Phe
    110                 115                 120

Pro Pro Ser Asp Glu Gln Leu Lys Ser Gly Thr Ala Ser Val Val
125                 130                 135

Cys Leu Leu Asn Asn Phe Tyr Pro Arg Glu Ala Lys Val Gln Trp
            140                 145                 150

Lys Val Asp Asn Ala Leu Gln Ser Gly Asn Ser Gln Glu Ser Val

```
                    155                 160                 165

Thr Glu Gln Asp Ser Lys Asp Ser Thr Tyr Ser Leu Ser Ser Thr
                    170                 175                 180

Leu Thr Leu Ser Lys Ala Asp Tyr Glu Lys His Lys Val Tyr Ala
                    185                 190                 195

Cys Glu Val Thr His Gln Gly Leu Ser Ser Pro Val Thr Lys Ser
                    200                 205                 210

Phe Asn Arg Gly Glu Cys Ala Ala Ala His His His His His
                    215                 220                 225

Gly Ala Ala Glu Gln Lys Leu Ile Ser Glu Glu Asp Leu Asn Gly
                    230                 235                 240

Ala Ala

<210> SEQ ID NO 17
<211> LENGTH: 263
<212> TYPE: PRT
<213> ORGANISM: Artificial sequence
<220> FEATURE:
<223> OTHER INFORMATION: homodimeric IgVL2-t sequence from mutant IgVL-t
      5D3

<400> SEQUENCE: 17

Glu Ile Val Leu Thr Gln Ser Pro Gly Thr Leu Ser Leu Ser Pro
1               5                   10                  15

Gly Glu Arg Ala Thr Leu Ser Cys Arg Ala Ser Gln Ser Val Gly
                    20                  25                  30

Gly Ser Tyr Leu Ala Trp Tyr Gln Gln Lys Pro Gly Gln Ala Pro
                    35                  40                  45

Arg Leu Leu Ile Tyr Gly Ala Ser Ser Arg Ala Thr Gly Ile Pro
                    50                  55                  60

Asp Arg Phe Ser Gly Ser Gly Ser Gly Thr Asp Phe Thr Leu Thr
                    65                  70                  75

Ile Ser Arg Leu Glu Pro Glu Asp Phe Ala Val Tyr Tyr Cys Gln
                    80                  85                  90

Leu Tyr Gly Gly Ser Pro Met Tyr Thr Phe Gly Gln Gly Thr Lys
                    95                  100                 105

Leu Glu Ile Lys Arg Ser Ser Gly Gly Gly Ser Gly Gly
                    110                 115                 120

Gly Ser Gly Gly Ser Ala Leu Glu Ile Val Leu Thr Gln Ser Pro
                    125                 130                 135

Gly Thr Leu Ser Leu Ser Pro Gly Glu Arg Ala Thr Leu Ser Cys
                    140                 145                 150

Arg Ala Ser Gln Ser Val Gly Gly Ser Tyr Leu Ala Trp Tyr Gln
                    155                 160                 165

Gln Lys Pro Gly Gln Ala Pro Arg Leu Leu Ile Tyr Gly Ala Ser
                    170                 175                 180

Ser Arg Ala Thr Gly Ile Pro Asp Arg Phe Ser Gly Ser Gly Ser
                    185                 190                 195

Gly Thr Asp Phe Thr Leu Thr Ile Ser Arg Leu Glu Pro Glu Asp
                    200                 205                 210

Phe Ala Val Tyr Tyr Cys Gln Leu Tyr Gly Gly Ser Pro Met Tyr
                    215                 220                 225

Thr Phe Gly Gln Gly Thr Lys Leu Glu Ile Lys Arg Ala Ala Ala
                    230                 235                 240

His His His His His His Gly Ala Ala Glu Gln Lys Leu Ile Ser
```

```
                        245                 250                 255

Glu Glu Asp Leu Asn Gly Ala Ala
                260

<210> SEQ ID NO 18
<211> LENGTH: 42
<212> TYPE: PRT
<213> ORGANISM: Homo sapiens
<220> FEATURE:
<223> OTHER INFORMATION: amyloid beta 42 peptide

<400> SEQUENCE: 18

Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala
            20                  25                  30

Ile Ile Gly Leu Met Val Gly Gly Val Val Ile Ala
            35                  40

<210> SEQ ID NO 19
<211> LENGTH: 150
<212> TYPE: PRT
<213> ORGANISM: Staphylococcus aureus
<220> FEATURE:
<223> OTHER INFORMATION: Efb amino acid sequence

<400> SEQUENCE: 19

Met Arg Gly Ser His His His His His His Gly Ala Asp Ala Ser
1               5                   10                  15

Glu Gly Tyr Gly Pro Arg Glu Lys Lys Pro Val Ser Ile Asn His
            20                  25                  30

Asn Ile Val Glu Tyr Asn Asp Gly Thr Phe Lys Tyr Gln Ser Arg
            35                  40                  45

Pro Lys Phe Asn Ser Thr Pro Lys Tyr Ile Lys Phe Lys His Asp
            50                  55                  60

Tyr Asn Ile Leu Glu Phe Asn Asp Gly Thr Phe Glu Tyr Gly Ala
            65                  70                  75

Arg Pro Gln Phe Asn Lys Pro Ala Ala Lys Thr Asp Ala Thr Ile
            80                  85                  90

Lys Lys Glu Gln Lys Leu Ile Gln Ala Gln Asn Leu Val Arg Glu
            95                  100                 105

Phe Glu Lys Thr His Thr Val Ser Ala His Arg Lys Ala Gln Lys
            110                 115                 120

Ala Val Asn Leu Val Ser Phe Glu Tyr Lys Val Lys Lys Met Val
            125                 130                 135

Leu Gln Glu Arg Ile Asp Asn Val Leu Lys Gln Gly Leu Val Lys
            140                 145                 150

<210> SEQ ID NO 20
<211> LENGTH: 333
<212> TYPE: DNA
<213> ORGANISM: Artificial sequence
<220> FEATURE:
<223> OTHER INFORMATION: VL domain nucleotide sequence of scFv 1C7

<400> SEQUENCE: 20
cagtctgtgt tgacgcagcc gccctcagtg tctgcggccc caggacagat          50
ggtcaccatc tcctgctccg gaagcagttc caacattaag gataatattg         100
tttcgtggta ccagaagttc ccaggaacag cccccaaact cctcatttat         150
```

```
gacaatgaga ggcgaccctc agggattcct gaccgattct ctggctccaa        200
gtctggcacg tcagccaccc tggccatcac cggactccag cccggggacg        250
aggccgatta ttactgcgca gcttgggata cacccttcg tggtggdddg         300 gtgttcggcg agggaccaa ggtcaccgtc cta                           333

<210> SEQ ID NO 21
<211> LENGTH: 333
<212> TYPE: DNA
<213> ORGANISM: Artificial sequence
<220> FEATURE:
<223> OTHER INFORMATION: VL domain nucleotide sequence of Vl-19

<400> SEQUENCE: 21
cagtctgtgt tgacgcagcc gccctcagtg tctgcggccc caggacagaa        50
ggtcaccatc tcctgctctg gaagcagctc caacattggg aataattatg       100
tatcctggta ccagcagctc ccaggaacag cccccaaact cctcatttat       150
gacaataata gcgaccctc agggattcct gaccgattct ctggctccaa        200
gtctggcacg tcagccaccc tgggcatcac cggactccag actggggacg       250
aggccgatta ttactgcgga acatgggata gcagcctgag tgctggttgg       300
gtgttcggcg agggaccaa gctgaccgtc cta                          333

<210> SEQ ID NO 22
<211> LENGTH: 111
<212> TYPE: PRT
<213> ORGANISM: Artificial sequence
<220> FEATURE:
<223> OTHER INFORMATION: VL domain amino acid sequence of scFv 1C7
<220> FEATURE:
<221> NAME/KEY: MISC_FEATURE
<222> LOCATION: 100
<223> OTHER INFORMATION: Xaa is any amino acid

<400> SEQUENCE: 22

Gln Ser Val Leu Thr Gln Pro Pro Ser Val Ser Ala Ala Pro Gly
1               5                   10                  15

Gln Met Val Thr Ile Ser Cys Ser Gly Ser Ser Ser Asn Ile Lys
                20                  25                  30

Asp Asn Ile Val Ser Trp Tyr Gln Lys Phe Pro Gly Thr Ala Pro
                35                  40                  45

Lys Leu Leu Ile Tyr Asp Asn Glu Arg Arg Pro Ser Gly Ile Pro
                50                  55                  60

Asp Arg Phe Ser Gly Ser Lys Ser Gly Thr Ser Ala Thr Leu Ala
                65                  70                  75

Ile Thr Gly Leu Gln Pro Gly Asp Glu Ala Asp Tyr Tyr Cys Ala
                80                  85                  90

Ala Trp Asp Asn Thr Leu Arg Gly Gly Xaa Val Phe Gly Gly Gly
                95                  100                 105

Thr Lys Val Thr Val Leu
                110

<210> SEQ ID NO 23
<211> LENGTH: 111
<212> TYPE: PRT
<213> ORGANISM: Artificial sequence
<220> FEATURE:
<223> OTHER INFORMATION: VL domain amino acid sequence of Vl-19
<220> FEATURE:
```

<221> NAME/KEY: MISC_FEATURE
<222> LOCATION: 100
<223> OTHER INFORMATION: Xaa is any amino acid

<400> SEQUENCE: 23

```
Gln Ser Val Leu Thr Gln Pro Pro Ser Val Ser Ala Ala Pro Gly
1               5                   10                  15

Gln Lys Val Thr Ile Ser Cys Ser Gly Ser Ser Ser Asn Ile Gly
                20                  25                  30

Asn Asn Tyr Val Ser Trp Tyr Gln Gln Leu Pro Gly Thr Ala Pro
            35                  40                  45

Lys Leu Leu Ile Tyr Asp Asn Asn Lys Arg Pro Ser Gly Ile Pro
        50                  55                  60

Asp Arg Phe Ser Gly Ser Lys Ser Gly Thr Ser Ala Thr Leu Gly
            65                  70                  75

Ile Thr Gly Leu Gln Thr Gly Asp Glu Ala Asp Tyr Tyr Cys Gly
                80                  85                  90

Thr Trp Asp Ser Ser Leu Ser Ala Gly Xaa Val Phe Gly Gly Gly
            95                  100                 105

Thr Lys Leu Thr Val Leu
            110
```

<210> SEQ ID NO 24
<211> LENGTH: 380
<212> TYPE: DNA
<213> ORGANISM: Artificial sequence
<220> FEATURE:
<223> OTHER INFORMATION: VH domain nucleotide sequence of scFv 1C7

<400> SEQUENCE: 24

```
gaggtgcagc tggtggagtc tgggggaggc gtggtccagc ctggggaggtc          50
cctgagactc tcctgtgcag cgtctggatt caccttcagt agctatggca          100
tgcactgggt ccgccaggct ccaggcaagg ggctggagtg ggtggcagtt          150
atatggtatg atggaagtaa taatactat gcagactccg tgaagggccg           200
attcaccatc tccagagaca attccaagaa cacgctgtat ctgctgcaaa          250
tgaacagcct gagagccgag gacacggctg tgtattactg tgcgagagat          300
ccagggatt gtagtggtgg tagctgctac tttdddddddd dgactactgg          350
ggccagggaa ccctggtcac cgtctcctca                                380
```

<210> SEQ ID NO 25
<211> LENGTH: 127
<212> TYPE: PRT
<213> ORGANISM: Artificial sequence
<220> FEATURE:
<223> OTHER INFORMATION: VH domain amino acid sequence of scFv 1C7
<220> FEATURE:
<221> NAME/KEY: MISC_FEATURE
<222> LOCATION: 112, 113, 114
<223> OTHER INFORMATION: Xaa is any amino acid

<400> SEQUENCE: 25

```
Glu Val Gln Leu Val Glu Ser Gly Gly Gly Val Val Gln Pro Gly
1               5                   10                  15

Arg Ser Leu Arg Leu Ser Cys Ala Ala Ser Gly Phe Thr Phe Ser
                20                  25                  30

Ser Tyr Gly Met His Trp Val Arg Gln Ala Pro Gly Lys Gly Leu
            35                  40                  45
```

Glu Trp Val Ala Val Ile Trp Tyr Asp Gly Ser Asn Lys Tyr Tyr
            50                  55                  60

Ala Asp Ser Val Lys Gly Arg Phe Thr Ile Ser Arg Asp Asn Ser
            65                  70                  75

Lys Asn Thr Leu Tyr Leu Leu Gln Met Asn Ser Leu Arg Ala Glu
            80                  85                  90

Asp Thr Ala Val Tyr Tyr Cys Ala Arg Asp Pro Gly Asp Cys Ser
            95                  100                 105

Gly Gly Ser Cys Tyr Phe Xaa Xaa Xaa Asp Tyr Trp Gly Gln Gly
            110                 115                 120

Thr Leu Val Thr Val Ser Ser
            125

<210> SEQ ID NO 26
<211> LENGTH: 380
<212> TYPE: DNA
<213> ORGANISM: Artificial sequence
<220> FEATURE:
<223> OTHER INFORMATION: VH domain nucleotide sequence of VH3-33
<220> FEATURE:
<221> NAME/KEY: modified_base
<222> LOCATION: 300, 301, 302
<223> OTHER INFORMATION: n is inosine

<400> SEQUENCE: 26
gaggtgcagc tggtggagtc tgggggaggc gtggtccagc ctggggaggtc         50 cctgagactc tcctgtgcag cgtctggatt caccttcagt agctatggca        100
tgcactgggt ccgccaggct ccaggcaagg gctggagtg gtggcagtt           150 atatggtatg atggaagtaa taaatactat gcagactccg tgaagggccg        200
attcaccatc tccagagaca attccaagaa cacgctgtat ctgctgcaaa        250
tgaacagcct gagagccgag gacacggctg tgtattactg tgcgagagan        300
nnaggatatt gtagtggtgg tagctgctac tccactactt tgactactgg        350
ggccaaggaa ccctggtcac cgtctcctca                              380

<210> SEQ ID NO 27
<211> LENGTH: 127
<212> TYPE: PRT
<213> ORGANISM: Artificial sequence
<220> FEATURE:
<223> OTHER INFORMATION: VH domain amino acid sequence of VH3-33
<220> FEATURE:
<221> NAME/KEY: MISC_FEATURE
<222> LOCATION: 112
<223> OTHER INFORMATION: Xaa is any amino acid

<400> SEQUENCE: 27

Glu Val Gln Leu Val Glu Ser Gly Gly Gly Val Val Gln Pro Gly
1                   5                   10                  15

Arg Ser Leu Arg Leu Ser Cys Ala Ala Ser Gly Phe Thr Phe Ser
            20                  25                  30

Ser Tyr Gly Met His Trp Val Arg Gln Ala Pro Gly Lys Gly Leu
            35                  40                  45

Glu Trp Val Ala Val Ile Trp Tyr Asp Gly Ser Asn Lys Tyr Tyr
            50                  55                  60

Ala Asp Ser Val Lys Gly Arg Phe Thr Ile Ser Arg Asp Asn Ser
            65                  70                  75

Lys Asn Thr Leu Tyr Leu Leu Gln Met Asn Ser Leu Arg Ala Glu
            80                  85                  90

Asp Thr Ala Val Tyr Tyr Cys Ala Arg Glu Pro Gly Asp Cys Ser
            95                 100                 105

Gly Gly Ser Cys Tyr Phe Xaa Tyr Phe Asp Tyr Trp Gly Gln Gly
        110                 115                 120

Thr Leu Val Thr Val Ser Ser
            125

<210> SEQ ID NO 28
<211> LENGTH: 327
<212> TYPE: DNA
<213> ORGANISM: Artificial sequence
<220> FEATURE:
<223> OTHER INFORMATION: N-terminal VL domain nucleotide sequence of
      IgVL2-t 1B4

<400> SEQUENCE: 28
tcttctgagc tgactcagga ccctgctgtg tctgtggcct tgggacagac        50
agtcaggatc acatgccaag gagacagcct cagaagctat tatgcaagct       100
ggtaccagca gaagccagga caggcccctg tacttgtcat ctatggtaaa       150
aacaaccggc cctcagggat cccagaccga ttctctggct ccagctcagg       200
aaacacagct tccttgacca tcactggggc tcaggcggaa gatgaggctg       250
actattactg taactcccgg gacagcagtg gtaaccatdd dtgggtgttc       300
ggcggaggga ccaaggtcac cgtccta                                327

<210> SEQ ID NO 29
<211> LENGTH: 327
<212> TYPE: DNA
<213> ORGANISM: Artificial sequence
<220> FEATURE:
<223> OTHER INFORMATION: N-terminal VL domain nucleotide sequence of
      V2-13

<400> SEQUENCE: 29
tcttctgagc tgactcagga ccctgctgtg tctgtggcct tgggacagac        50
agtcaggatc acatgccaag gagacagcct cagaagctat tatgcaagct       100
ggtaccagca gaagccagga caggcccctg tacttgtcat ctatggtaaa       150
aacaaccggc cctcagggat cccagaccga ttctctggct ccagctcagg       200
aaacacagct tccttgacca tcactggggc tcaggcggaa gatgaggctg       250
actattactg taactcccgg gacagcagtg gtaaccatct ttgggtgttc       300
ggcggaggga ccaagctgac cgtccta                                327

<210> SEQ ID NO 30
<211> LENGTH: 109
<212> TYPE: PRT
<213> ORGANISM: Artificial sequence
<220> FEATURE:
<223> OTHER INFORMATION: N-terminal VL domain amino acid sequence of
      IgVL2-t 1B4
<220> FEATURE:
<221> NAME/KEY: MISC_FEATURE
<222> LOCATION: 97
<223> OTHER INFORMATION: Xaa is any amino acid

<400> SEQUENCE: 30

Ser Ser Glu Leu Thr Gln Asp Pro Ala Val Ser Val Ala Leu Gly
1               5                   10                  15

Gln Thr Val Arg Ile Thr Cys Gln Gly Asp Ser Leu Arg Ser Tyr

```
                    20                  25                  30

Tyr Ala Ser Trp Tyr Gln Gln Lys Pro Gly Gln Ala Pro Val Leu
                    35                  40                  45

Val Ile Tyr Gly Lys Asn Asn Arg Pro Ser Gly Ile Pro Asp Arg
                    50                  55                  60

Phe Ser Gly Ser Ser Ser Gly Asn Thr Ala Ser Leu Thr Ile Tyr
                    65                  70                  75

Gly Ala Gln Ala Glu Asp Glu Ala Asp Tyr Tyr Cys Asn Ser Arg
                    80                  85                  90

Asp Ser Ser Gly Asn His Xaa Trp Val Phe Gly Gly Gly Thr Lys
                    95                 100                 105

Val Thr Val Leu

<210> SEQ ID NO 31
<211> LENGTH: 109
<212> TYPE: PRT
<213> ORGANISM: Artificial sequence
<220> FEATURE:
<223> OTHER INFORMATION: N-terminal VL domain amino acid sequence of
      V2-13;
<220> FEATURE:
<221> NAME/KEY: MISC_FEATURE
<222> LOCATION: 97
<223> OTHER INFORMATION: Xaa is any amino acid

<400> SEQUENCE: 31

Ser Ser Glu Leu Thr Gln Asp Pro Ala Val Ser Val Ala Leu Gly
1               5                  10                  15

Gln Thr Val Arg Ile Thr Cys Gln Gly Asp Ser Leu Arg Ser Tyr
                    20                  25                  30

Tyr Ala Ser Trp Tyr Gln Gln Lys Pro Gly Gln Ala Pro Val Leu
                    35                  40                  45

Val Ile Tyr Gly Lys Asn Asn Arg Pro Ser Gly Ile Pro Asp Arg
                    50                  55                  60

Phe Ser Gly Ser Ser Ser Gly Asn Thr Ala Ser Leu Thr Ile Tyr
                    65                  70                  75

Gly Ala Gln Ala Glu Asp Glu Ala Asp Tyr Tyr Cys Asn Ser Arg
                    80                  85                  90

Asp Ser Ser Gly Asn His Xaa Trp Val Phe Gly Gly Gly Thr Lys
                    95                 100                 105

Leu Thr Val Leu

<210> SEQ ID NO 32
<211> LENGTH: 325
<212> TYPE: DNA
<213> ORGANISM: Artificial sequence
<220> FEATURE:
<223> OTHER INFORMATION: C-terminal VL domain nucleotide sequence of
      IgVL2-t 1B4

<400> SEQUENCE: 32
gacatccagt tgacccagtc tccatcctcc ctgcctgcat ctgtaggaga        50
cagagtcacc atcacttgcc gggcaagtca gagcattagc agctatttaa       100
actggtatca gcagaaacca gggaaagccc ctaagctcct gatctatgct       150
gcatccagtt tgcaaagtgg ggtcccatca aggttcagtg gcagtggatc       200
tgggacagat ttcactctca ccatcagcag tctgcaacct gaagattttg       250
caacttacta ctgtcaacaa agttacagta cccacddddd dacgttcggc       300
```

```
caagggacca agctggaaat caaac                                          325

<210> SEQ ID NO 33
<211> LENGTH: 325
<212> TYPE: DNA
<213> ORGANISM: Artificial sequence
<220> FEATURE:
<223> OTHER INFORMATION: C-terminal VL domain nucleotide sequence of
      O2/O12

<400> SEQUENCE: 33
gacatccaga tgacccagtc tccatcctcc ctgtctgcat ctgtaggaga               50
cagagtcacc atcacttgcc gggcaagtca gagcattagc agctatttaa              100
attggtatca gcagaaacca gggaaagccc ctaagctcct gatctatgct              150
gcatccagtt tgcaaagtgg ggtcccatca aggttcagtg gcagtggatc              200
tgggacagat tcactctcac ccatcagcag tctgcaacct gaagattttg              250
caacttacta ctgtcaacaa agttacagta ccccctccgtg acgttcggc              300 caagggacca agctggaaat caaac                                          325

<210> SEQ ID NO 34
<211> LENGTH: 108
<212> TYPE: PRT
<213> ORGANISM: Artificial sequence
<220> FEATURE:
<223> OTHER INFORMATION: C-terminal VL domain nucleotide sequence of
      IgVL2-t 1B4
<220> FEATURE:
<221> NAME/KEY: MISC_FEATURE
<222> LOCATION: 96, 97
<223> OTHER INFORMATION: Xaa is Lys, Asn, Arg, Ser Ile, Met, Glu Asp,
      Gly, Val, Tyr, Trp, Cys, Leu, or Phe

<400> SEQUENCE: 34

Asp Ile Gln Leu Thr Gln Ser Pro Ser Ser Leu Pro Ala Ser Val
1               5                   10                  15

Gly Asp Arg Val Thr Ile Thr Cys Arg Ala Ser Gln Ser Ile Ser
                20                  25                  30

Ser Tyr Leu Asn Thr Tyr Gln Gln Lys Pro Gly Lys Ala Pro Lys
                35                  40                  45

Leu Leu Ile Tyr Ala Ala Ser Ser Leu Gln Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr Ser Thr His Xaa Xaa Thr Phe Gly Gln Gly Thr Lys Leu
                95                  100                 105

Glu Ile Lys

<210> SEQ ID NO 35
<211> LENGTH: 108
<212> TYPE: PRT
<213> ORGANISM: Artificial sequence
<220> FEATURE:
<223> OTHER INFORMATION: C-terminal VL domain nucleotide sequence of
      O2/O12
<220> FEATURE:
<221> NAME/KEY: MISC_FEATURE
<222> LOCATION: 96, 97
<223> OTHER INFORMATION: Xaa is Lys, Asn, Arg, Ser Ile, Met, Glu Asp,
```

Gly, Val, Tyr, Trp, Cys, Leu, or Phe

<400> SEQUENCE: 35

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser
                20                  25                  30

Ser Tyr Leu Asn Thr Tyr Gln Gln Lys Pro Gly Lys Ala Pro Lys
                35                  40                  45

Leu Leu Ile Tyr Ala Ala Ser Ser Leu Gln Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr Ser Thr Pro Xaa Xaa Thr Phe Gly Gln Gly Thr Lys Val
                95                  100                 105

Glu Ile Lys

<210> SEQ ID NO 36
<211> LENGTH: 20
<212> TYPE: PRT
<213> ORGANISM: Artificial sequence
<220> FEATURE:
<223> OTHER INFORMATION: HIV gp120 306-325 Clade B peptide

<400> SEQUENCE: 36

Tyr Asn Lys Arg Lys Arg Ile His Ile Gly Pro Gly Arg Ala Phe
1               5                   10                  15

Tyr Thr Thr Lys Arg
                20

<210> SEQ ID NO 37
<211> LENGTH: 18
<212> TYPE: PRT
<213> ORGANISM: Artificial sequence
<220> FEATURE:
<223> OTHER INFORMATION: HIV gp120 306-325 97ZA009 peptide

<400> SEQUENCE: 37

Thr Arg Lys Ser Met Arg Ile Gly Pro Gly Gln Val Phe Tyr Ala
1               5                   10                  15

Thr Asn Gly

<210> SEQ ID NO 38
<211> LENGTH: 13
<212> TYPE: PRT
<213> ORGANISM: Artificial sequence
<220> FEATURE:
<223> OTHER INFORMATION: HIV gp120 421-433 Clade B peptide

<400> SEQUENCE: 38

Lys Gln Ile Ile Asn Met Trp Gln Glu Val Gly Lys Ala
1               5                   10

<210> SEQ ID NO 39
<211> LENGTH: 13
<212> TYPE: PRT
<213> ORGANISM: Artificial sequence
<220> FEATURE:
<223> OTHER INFORMATION: HIV gp120 421-433 97ZA009 peptide

```
<400> SEQUENCE: 39

Lys Gln Ile Ile Asn Met Trp Gln Glu Val Gly Arg Ala
1               5                   10

<210> SEQ ID NO 40
<211> LENGTH: 19
<212> TYPE: PRT
<213> ORGANISM: Artificial sequence
<220> FEATURE:
<223> OTHER INFORMATION: HIV gp120 421-433 peptide epitope

<400> SEQUENCE: 40

Cys Leu Pro Ser Arg Ile Lys Gln Ile Ile Asn Met Trp Gln Glu
1               5                   10                  15

Val Gly Lys Ala

<210> SEQ ID NO 41
<211> LENGTH: 11
<212> TYPE: PRT
<213> ORGANISM: Artificial sequence
<220> FEATURE:
<223> OTHER INFORMATION: HIV gp120 421-433 peptide epitope

<400> SEQUENCE: 41

Lys Gln Ile Ile Asn Met Trp Gln Glu Val Gly
1               5                   10

<210> SEQ ID NO 42
<211> LENGTH: 16
<212> TYPE: PRT
<213> ORGANISM: Artificial sequence
<220> FEATURE:
<223> OTHER INFORMATION: HIV gp120 421-436 peptide epitope

<400> SEQUENCE: 42

Lys Gln Ile Ile Asn Met Trp Gln Glu Val Gly Lys Ala Met Tyr
1               5                   10                  15

Ala

<210> SEQ ID NO 43
<211> LENGTH: 107
<212> TYPE: PRT
<213> ORGANISM: Artificial sequence
<220> FEATURE:
<223> OTHER INFORMATION: Light chain SK18 VL domain

<400> SEQUENCE: 43

Asp Ile Gln Met Thr Gln Ser Pro Ser Ser Leu Ser Ala Ser Val
1               5                   10                  15

Gly Asp Arg Val Thr Val Thr Cys Arg Ala Ser Gln Ser Ile Ser
                20                  25                  30

Ser Tyr Leu Asn Trp Tyr Gln Gln Gln Pro Gly Lys Ala Pro Lys
                35                  40                  45

Leu Leu Ile Tyr Ala Ala Ser Ser Leu Gln Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Phe Cys Gln Gln
                80                  85                  90

Ser Tyr Ser Ile Pro Arg Thr Phe Gly Gln Gly Thr Lys Val Glu
                95                  100                 105
```

Ile Lys

<210> SEQ ID NO 44
<211> LENGTH: 107
<212> TYPE: PRT
<213> ORGANISM: Artificial sequence
<220> FEATURE:
<223> OTHER INFORMATION: Light chain SK45 VL domain

<400> SEQUENCE: 44

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Arg
                20                  25                  30

Asn Asp Leu Gly Trp Tyr Gln Gln Lys Pro Gly Lys Ala Pro Lys
                35                  40                  45

Ala Leu Ile Tyr Ala Ala Ser Ser Leu Gln Ser Gly Val Pro Ser
                50                  55                  60

Arg Phe Ser Gly Ser Gly Ser Gly Thr Glu Phe Thr Leu Thr Ile
                65                  70                  75

Ser Ser Leu Gln Pro Glu Asp Phe Ala Thr Tyr Tyr Cys Leu Gln
                80                  85                  90

His Asn Ser Tyr Pro Leu Thr Phe Gly Gly Gly Thr Lys Val Glu
                95                  100                 105

Ile Lys

<210> SEQ ID NO 45
<211> LENGTH: 107
<212> TYPE: PRT
<213> ORGANISM: Artificial sequence
<220> FEATURE:
<223> OTHER INFORMATION: Light chain SKL6 VL domain

<400> SEQUENCE: 45

Asp Ile Gln Met Thr Gln Ser Pro Ser Ser Leu Ser Ala Ser Val
1               5                   10                  15

Gly Asp Gly Val Thr Ile Thr Cys Arg Ala Ser Gln Ser Ile Ser
                20                  25                  30

Ser Tyr Leu His Trp Tyr Gln Gln Lys Pro Gly Lys Ala Pro Lys
                35                  40                  45

Leu Leu Ile Tyr Val Ala Ser Ser Leu Gln Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr Ser Thr Pro Ile Thr Phe Gly Gln Gly Thr Arg Leu Glu
                95                  100                 105

Ile Lys

<210> SEQ ID NO 46
<211> LENGTH: 11
<212> TYPE: PRT
<213> ORGANISM: Artificial sequence
<220> FEATURE:
<223> OTHER INFORMATION: HIV gp120 421-431 peptide epitope

<400> SEQUENCE: 46

Lys Gln Ile Ile Asn Met Trp Gln Glu Val Gly

<210> SEQ ID NO 47
<211> LENGTH: 108
<212> TYPE: PRT
<213> ORGANISM: Artificial sequence
<220> FEATURE:
<223> OTHER INFORMATION: VL chain of scFv-t clone GL2

<400> SEQUENCE: 47

```
Glu Thr Thr Leu Thr Gln Ser Pro Ala Thr Leu Ser Leu Ser Pro
1               5                   10                  15

Gly Glu Arg Ala Thr Leu Ser Cys Arg Ala Ser Gln Ser Val Ser
            20                  25                  30

Ser Tyr Leu Ala Trp Tyr Gln Gln Lys Pro Gly Gln Ala Pro Arg
        35                  40                  45

Leu Leu Ile Tyr Asp Ala Ser Asn Arg Ala Thr Gly Ile Pro Ala
    50                  55                  60

Arg Phe Ser Gly Ser Gly Ser Gly Thr Asp Phe Thr Leu Thr Ile
        65                  70                  75

Ser Ser Leu Glu Pro Glu Asp Phe Ala Val Tyr Tyr Cys Gln Gln
            80                  85                  90

Arg Ser Asn Trp Pro Leu Thr Phe Gly Gly Gly Thr Lys Leu Glu
                95                  100                 105

Ile Lys Arg
```

<210> SEQ ID NO 48
<211> LENGTH: 136
<212> TYPE: PRT
<213> ORGANISM: Artificial sequence
<220> FEATURE:
<223> OTHER INFORMATION: VH chain of scFv-t clone GL2

<400> SEQUENCE: 48

```
Leu Gln Val Gln Leu Gln Gln Ser Gly Pro Arg Leu Val Lys Pro
1               5                   10                  15

Ser Gly Thr Leu Ser Leu Thr Cys Thr Val Ser Gly Gly Ser Ile
            20                  25                  30

Ser Ser Ser Ser Tyr Tyr Trp Gly Trp Ile Arg Gln His Pro Gly
        35                  40                  45

Lys Gly Leu Glu Trp Ile Gly Tyr Ile Tyr Tyr Ser Gly Ser Thr
        50                  55                  60

Tyr Tyr Asn Pro Ser Leu Lys Ser Arg Val Thr Ile Ser Val Asp
            65                  70                  75

Thr Ser Lys Asn Gln Phe Ser Leu Lys Leu Ser Ser Val Thr Ala
            80                  85                  90

Ala Asp Thr Ala Val Tyr Tyr Cys Ala Arg Leu Gln Gly Ala Arg
            95                  100                 105

Gly Tyr Ser Tyr Gly Tyr Gly Ile Asp Tyr Trp Gly Gln Gly Thr
            110                 115                 120

Leu Val Thr Val Ser Ser Gly Ser Ala Ser Ala Pro Thr Leu Phe
            125                 130                 135

Pro
```

<210> SEQ ID NO 49
<211> LENGTH: 111
<212> TYPE: PRT
<213> ORGANISM: Artificial sequence
<220> FEATURE:
<223> OTHER INFORMATION: VL chain of scFv-t clone JL427

<400> SEQUENCE: 49

Gln Ser Val Leu Thr Gln Pro Pro Ser Val Ser Gly Ala Pro Gly
1               5                   10                  15

Gln Arg Val Thr Ile Ser Cys Ser Gly Ser Ser Ser Asn Phe Gly
                20                  25                  30

Leu Asn Tyr Val Tyr Trp Tyr Gln His Phe Pro Gly Thr Ala Pro
                35                  40                  45

Lys Leu Leu Ile Tyr Arg Asn Asp Gln Arg Pro Leu Gly Val Pro
                50                  55                  60

Ala Arg Phe Ser Gly Ser Lys Ser Gly Thr Ser Ala Ser Leu Ala
                65                  70                  75

Ile Ser Gly Leu Arg Ser Glu Asp Glu Ala Asp Tyr Tyr Cys Gln
                80                  85                  90

Ser Tyr Asp Asn Ser Leu Ser Gly Trp Val Phe Gly Gly Gly Thr
                95                  100                 105

Gln Leu Thr Val Leu Gly
                110

<210> SEQ ID NO 50
<211> LENGTH: 129
<212> TYPE: PRT
<213> ORGANISM: Artificial sequence
<220> FEATURE:
<223> OTHER INFORMATION: VH chain of scFv-t clone JL427

<400> SEQUENCE: 50

Leu Gln Val Gln Leu Gln Gln Ser Gly Gly Gly Leu Val Gln Pro
1               5                   10                  15

Gly Arg Ser Leu Arg Leu Ser Cys Ala Ala Ser Gly Phe Thr Phe
                20                  25                  30

Ser Ser Tyr Gly Met His Trp Val Arg Gln Ala Pro Gly Lys Gly
                35                  40                  45

Leu Glu Trp Val Ser Tyr Ile Gly Arg Ser Gly Ser His Thr Asn
                50                  55                  60

Tyr Ala Asp Ser Val Lys Gly Arg Phe Thr Ile Ser Arg Asp Asn
                65                  70                  75

Ser Lys Asn Thr Leu Tyr Leu Gln Ile Asn Ser Leu Arg Ala Glu
                80                  85                  90

Asp Thr Ala Val Tyr Tyr Cys Ala Arg Gly Leu Pro Asn Tyr Gly
                95                  100                 105

Met Asp Ile Trp Gly Gln Gly Thr Thr Val Thr Val Ser Ser Gly
                110                 115                 120

Ser Ala Ser Ala Pro Thr Leu Phe Pro
                125

<210> SEQ ID NO 51
<211> LENGTH: 109
<212> TYPE: PRT
<213> ORGANISM: Artificial sequence
<220> FEATURE:
<223> OTHER INFORMATION: VL chain of scFv-t clone JL606

<400> SEQUENCE: 51

Glu Thr Thr Leu Thr Gln Ser Pro Gly Ile Leu Ser Leu Ser Pro
1               5                   10                  15

```
Gly Glu Arg Ala Thr Leu Ser Cys Arg Ala Ser Gln Arg Val Ser
            20                  25                  30

Ser Ser Tyr Leu Ala Trp Tyr Gln Gln Lys Pro Gly Gln Ala Pro
            35                  40                  45

Arg Leu Leu Ile Tyr Gly Ala Ser Thr Arg Ala Thr Gly Ile Pro
            50                  55                  60

Asp Arg Phe Ser Gly Ser Gly Ser Gly Thr Asp Phe Thr Leu Thr
            65                  70                  75

Ile Thr Arg Leu Glu Pro Glu Asp Phe Ala Val Tyr Tyr Cys Gln
            80                  85                  90

Gln Tyr Ser Ser Ser Arg Ser Thr Phe Gly Gln Gly Thr Lys Val
            95                 100                 105

Glu Ile Lys Arg

<210> SEQ ID NO 52
<211> LENGTH: 132
<212> TYPE: PRT
<213> ORGANISM: Artificial sequence
<220> FEATURE:
<223> OTHER INFORMATION: VH chain of scFv-t clone JL606

<400> SEQUENCE: 52

Leu Gln Val Gln Leu Gln Glu Ser Gly Pro Gly Leu Val Lys Pro
1               5                  10                  15

Ser Glu Thr Leu Ser Leu Thr Cys Thr Val Ser Gly Gly Ser Ile
            20                  25                  30

Ser Ser Tyr Tyr Trp Ser Trp Ile Arg Gln Pro Ala Gly Lys Gly
            35                  40                  45

Leu Glu Trp Ile Gly Arg Ile Tyr Thr Ser Gly Ser Thr Asn Tyr
            50                  55                  60

Asn Pro Ser Leu Lys Ser Arg Val Thr Met Ser Val Asp Thr Ser
            65                  70                  75

Lys Asn Gln Phe Ser Leu Lys Leu Ser Ser Val Thr Ala Ala Asp
            80                  85                  90

Thr Ala Val Tyr Tyr Cys Ala Arg His Gln Arg Asp Ile Val Val
            95                 100                 105

Val Pro Ala Leu Asp Val Trp Gly Lys Gly Thr Thr Val Thr Val
           110                 115                 120

Ser Ser Gly Ser Ala Ser Ala Pro Thr Leu Phe Pro
           125                 130

<210> SEQ ID NO 53
<211> LENGTH: 108
<212> TYPE: PRT
<213> ORGANISM: Artificial sequence
<220> FEATURE:
<223> OTHER INFORMATION: VL chain of scFv-t clone GL59

<400> SEQUENCE: 53

Ser Tyr Val Leu Thr Gln Pro Pro Ser Val Ser Val Ala Pro Gly
1               5                  10                  15

Gln Thr Ala Arg Ile Thr Cys Gly Gly Tyr Asn Ile Gly Ser Ser
            20                  25                  30

Ser Val His Trp Tyr Gln Gln Lys Ser Gly Gln Ala Pro Val Leu
            35                  40                  45

Val Val Tyr Asp Asp Ser Asp Arg Pro Ser Gly Ile Pro Glu Arg
            50                  55                  60
```

```
Phe Ser Gly Ser Asn Ser Gly Thr Thr Ala Thr Leu Thr Ile Ser
                65                  70                  75

Arg Val Glu Ala Gly Asp Glu Ala Asp Tyr Tyr Cys Gln Val Trp
            80                  85                  90

Asp Arg Gly Ser Asp Ser Tyr Val Phe Gly Thr Gly Thr Glu Val
                95                 100                 105

Thr Val Leu

<210> SEQ ID NO 54
<211> LENGTH: 136
<212> TYPE: PRT
<213> ORGANISM: Artificial sequence
<220> FEATURE:
<223> OTHER INFORMATION: VH chain of scFv-t clone GL59

<400> SEQUENCE: 54

Leu Gln Val Gln Leu Val Gln Ser Gly Ala Glu Val Lys Lys Pro
1               5                  10                  15

Gly Ser Ser Val Lys Val Ser Cys Lys Ala Ser Gly Gly Ala Phe
                20                  25                  30

Ser Asn Tyr Leu Ile Thr Trp Val Arg Gln Ala Pro Gly Gln Gly
                35                  40                  45

Leu Glu Tyr Leu Gly Arg Ile Ile Pro Ile Leu Gln Lys Ser Ser
            50                  55                  60

Tyr Ala Gln Lys Phe Glu Gly Arg Val Thr Phe Thr Ala Asp Lys
                65                  70                  75

Ser Thr Ser Thr Ala Tyr Met Glu Leu Thr Arg Leu Thr Ser Asp
            80                  85                  90

Asp Thr Ala Val Phe Tyr Cys Ala Ala Val Arg Ile Val Pro Val
                95                 100                 105

Pro Ser Leu Pro Pro Gly Ser Phe Phe Tyr Trp Gly Leu Gly Thr
                110                 115                 120

Val Val Thr Val Ser Ser Ala Ser Thr Lys Gly Pro Ser Val Phe
                125                 130                 135

Pro

<210> SEQ ID NO 55
<211> LENGTH: 111
<212> TYPE: PRT
<213> ORGANISM: Artificial sequence
<220> FEATURE:
<223> OTHER INFORMATION: VL chain of scFv-t clone JL678

<400> SEQUENCE: 55

Gln Ala Val Leu Thr Gln Pro Ser Ser Ala Ser Gly Thr Pro Gly
1               5                  10                  15

Arg Arg Val Thr Ile Ser Cys Ser Gly Ser Ser Ser Asn Ile Gly
                20                  25                  30

Ser Asn Thr Val Asn Trp Tyr Gln Gln Leu Pro Gly Thr Ala Pro
                35                  40                  45

Lys Leu Leu Ile Tyr Ser Asn Asn Gln Trp Pro Ser Gly Val Pro
            50                  55                  60

Asp Arg Phe Ser Gly Ser Lys Ser Gly Thr Ser Ala Ser Leu Ala
                65                  70                  75

Ile Ser Gly Leu Gln Ser Glu Asp Glu Ala Asp Tyr Tyr Cys Ala
            80                  85                  90

Ala Trp Asp Asp Ser Leu Asn Gly Pro Val Phe Gly Gly Gly Thr
```

```
                    95                  100                 105

Gln Leu Thr Val Leu Gly
                110

<210> SEQ ID NO 56
<211> LENGTH: 130
<212> TYPE: PRT
<213> ORGANISM: Artificial sequence
<220> FEATURE:
<223> OTHER INFORMATION: VH chain of scFv-t clone JL678

<400> SEQUENCE: 56

Leu Gln Val Gln Leu Gln Gln Ser Gly Ser Gly Leu Val Lys Pro
1               5                   10                  15

Ser Gln Thr Leu Ser Leu Thr Cys Thr Val Ser Gly Val Ser Ile
                20                  25                  30

Glu Ser Gly Ala Ser Tyr Trp Ser Trp Ile Arg Gln Arg Pro Gly
                35                  40                  45

Asn Gly Leu Glu Trp Ile Gly Tyr Ile Ser Tyr Ser Gly Ser Thr
                50                  55                  60

Asn Tyr Asn Pro Ser Leu Lys Ser Arg Val Phe Ile Ser Gly Asp
                65                  70                  75

Thr Ser Lys Asn Gln Phe Ser Leu Arg Leu Ser Ser Val Thr Ala
                80                  85                  90

Ala Asp Thr Ala Ile Tyr Tyr Cys Ala Arg Arg Pro Arg Thr Gly
                95                  100                 105

Arg Phe Asp Ser Trp Gly Gln Gly Ala Leu Val Ile Val Ser Ser
                110                 115                 120

Ala Ser Thr Lys Gly Pro Ser Val Phe Pro
                125                 130

<210> SEQ ID NO 57
<211> LENGTH: 16
<212> TYPE: PRT
<213> ORGANISM: Artificial sequence
<220> FEATURE:
<223> OTHER INFORMATION: SCFV-T VL and VH chain linker

<400> SEQUENCE: 57

Ser Ser Gly Gly Gly Gly Ser Gly Gly Gly Gly Ser Gly Gly Ser
1               5                   10                  15

Ala

<210> SEQ ID NO 58
<211> LENGTH: 26
<212> TYPE: PRT
<213> ORGANISM: Artificial sequence
<220> FEATURE:
<223> OTHER INFORMATION: VH chain of scFv-t clone GL2

<400> SEQUENCE: 58

Ala Ala Ala His His His His His His Gly Ala Ala Glu Gln Lys
1               5                   10                  15

Leu Ile Ser Glu Glu Asp Leu Asn Gly Ala Ala
                20                  25

<210> SEQ ID NO 59
<211> LENGTH: 110
<212> TYPE: PRT
<213> ORGANISM: Artificial sequence
<220> FEATURE:
```

<223> OTHER INFORMATION: VL1 chain of scFv-t clone GL1

<400> SEQUENCE: 59

```
Gln Ser Val Leu Thr Gln Pro Pro Ser Val Ser Ala Ala Pro Gly
1               5                   10                  15

Gln Met Val Thr Ile Ser Cys Ser Gly Ser Ser Asn Ile Lys
                20                  25                  30

Asp Asn Ile Val Ser Trp Tyr Gln Lys Phe Pro Gly Thr Ala Pro
                35                  40                  45

Lys Leu Leu Ile Tyr Asp Asn Glu Arg Arg Pro Ser Gly Ile Pro
                50                  55                  60

Asp Arg Phe Ser Gly Ser Lys Ser Gly Thr Ser Ala Thr Leu Gly
                65                  70                  75

Ile Thr Gly Leu Gln Thr Gly Asp Glu Ala Asp Tyr Tyr Cys Gly
                80                  85                  90

Thr Trp Asp Asn Ser Leu Ser Phe Trp Val Phe Gly Gly Gly Thr
                95                  100                 105

Lys Val Thr Val Leu
                110
```

<210> SEQ ID NO 60
<211> LENGTH: 123
<212> TYPE: PRT
<213> ORGANISM: Artificial sequence
<220> FEATURE:
<223> OTHER INFORMATION: VH chain of scFv-t clone JL683

<400> SEQUENCE: 60

```
Gln Val Gln Leu Gln Glu Ser Gly Pro Gly Leu Val Lys Pro Ser
1               5                   10                  15

Glu Thr Leu Ser Leu Thr Cys Ala Val Ser Gly Tyr Ser Ile Ser
                20                  25                  30

Ser Gly Tyr Tyr Trp Gly Trp Ile Arg Gln Pro Pro Gly Lys Gly
                35                  40                  45

Leu Glu Trp Ile Gly Glu Ile Tyr His Ser Gly Ser Thr Asn Tyr
                50                  55                  60

Asn Pro Ser Leu Lys Ser Arg Val Thr Ile Ser Val Asp Lys Ser
                65                  70                  75

Lys Asn Gln Phe Ser Leu Lys Leu Ser Ser Val Thr Ala Ala Asp
                80                  85                  90

Thr Ala Val Tyr Tyr Cys Ala Ser Arg Leu Gly Tyr Trp Gly Gln
                95                  100                 105

Gly Thr Leu Val Thr Val Ser Ser Gly Ser Ala Ser Ala Pro Thr
                110                 115                 120

Leu Phe Pro
```

<210> SEQ ID NO 61
<211> LENGTH: 107
<212> TYPE: PRT
<213> ORGANISM: Artificial sequence
<220> FEATURE:
<223> OTHER INFORMATION: VL chain of scFv-t clone JL651

<400> SEQUENCE: 61

```
Ser Tyr Val Leu Thr Gln Pro Pro Ser Val Ser Val Ser Pro Gly
1               5                   10                  15

Gln Pro Ala Ser Ile Thr Cys Ser Gly Asp Lys Leu Gly Asp Lys
                20                  25                  30
```

```
Tyr Ala Cys Trp Tyr Gln Gln Lys Pro Gly Arg Ser Pro Val Leu
                35                  40                  45

Val Ile Tyr Glu Asp Asn Lys Arg Pro Ser Gly Ile Pro Glu Arg
 50                  55                  60

Leu Ser Gly Ser Asn Ser Gly Asn Thr Ala Thr Leu Thr Ile Ser
                 65                  70                  75

Gly Thr Gln Ala Leu Asp Glu Ala Asp Tyr Tyr Cys Gln Ala Trp
                 80                  85                  90

Asp Ser Ser Thr Val Val Phe Gly Gly Gly Thr Lys Val Thr Val
                 95                 100                 105

Leu Gly

<210> SEQ ID NO 62
<211> LENGTH: 60
<212> TYPE: PRT
<213> ORGANISM: Artificial sequence
<220> FEATURE:
<223> OTHER INFORMATION: IgVLt tag sequence

<400> SEQUENCE: 62

Ser Ser Gly Gly Gly Gly Ser Gly Gly Gly Ser Gly Gly Ser
 1               5                  10                  15

Ala Leu Gln Val Gln Leu Gln Gln Ser Gly Gln Thr Lys Gly Pro
                 20                  25                  30

Ser Val Phe Pro Ala Ala Ala His His His His His His Gly Ala
                 35                  40                  45

Ala Glu Gln Lys Leu Ile Ser Glu Glu Asp Leu Asn Gly Ala Ala
                 50                  55                  60

<210> SEQ ID NO 63
<211> LENGTH: 136
<212> TYPE: PRT
<213> ORGANISM: Artificial sequence
<220> FEATURE:
<223> OTHER INFORMATION: VH4 chain of GL2 VH

<400> SEQUENCE: 63

Leu Gln Val Gln Leu Gln Gln Ser Gly Pro Arg Leu Val Lys Pro
 1               5                  10                  15

Ser Gly Thr Leu Ser Leu Thr Cys Thr Val Ser Gly Gly Ser Ile
                 20                  25                  30

Ser Ser Ser Ser Tyr Tyr Trp Gly Trp Ile Arg Gln His Pro Gly
                 35                  40                  45

Lys Gly Leu Glu Trp Ile Gly Tyr Ile Tyr Tyr Ser Gly Ser Thr
                 50                  55                  60

Tyr Tyr Asn Pro Ser Leu Lys Ser Arg Val Thr Ile Ser Val Asp
                 65                  70                  75

Thr Ser Lys Asn Gln Phe Ser Leu Lys Leu Ser Ser Val Thr Ala
                 80                  85                  90

Ala Asp Thr Ala Val Tyr Tyr Cys Ala Arg Leu Gln Gly Ala Arg
                 95                 100                 105

Gly Tyr Ser Tyr Gly Tyr Gly Ile Asp Tyr Trp Gly Gln Gly Thr
                110                 115                 120

Leu Val Thr Val Ser Ser Gly Ser Ala Ser Ala Pro Thr Leu Phe
                125                 130                 135

Pro
```

<210> SEQ ID NO 64
<211> LENGTH: 162
<212> TYPE: PRT
<213> ORGANISM: Artificial sequence
<220> FEATURE:
<223> OTHER INFORMATION: GL2-FR1m VH chain

<400> SEQUENCE: 64

```
Leu Gln Val Gln Leu Gln Gln Ser Gly Gly Gly Leu Val Gln Pro
1               5                   10                  15

Gly Arg Ser Leu Arg Leu Ser Cys Ala Ala Ser Gly Phe Thr Phe
                20                  25                  30

Ser Ser Ser Ser Tyr Tyr Trp Gly Trp Ile Arg Gln His Pro Gly
                35                  40                  45

Lys Gly Leu Glu Trp Ile Gly Tyr Ile Tyr Tyr Ser Gly Ser Thr
                50                  55                  60

Tyr Tyr Asn Pro Ser Leu Lys Ser Arg Val Thr Ile Ser Val Asp
                65                  70                  75

Thr Ser Lys Asn Gln Phe Ser Leu Lys Leu Ser Ser Val Thr Ala
                80                  85                  90

Ala Asp Thr Ala Val Tyr Tyr Cys Ala Arg Leu Gln Gly Ala Arg
                95                  100                 105

Gly Tyr Ser Tyr Gly Tyr Gly Ile Asp Tyr Trp Gly Gln Gly Thr
                110                 115                 120

Leu Val Thr Val Ser Ser Gly Ser Ala Ser Ala Pro Thr Leu Phe
                125                 130                 135

Pro Ala Ala Ala His His His His His His Gly Ala Ala Glu Gln
                140                 145                 150

Lys Leu Ile Ser Glu Glu Asp Leu Asn Gly Ala Ala
                155                 160
```

<210> SEQ ID NO 65
<211> LENGTH: 162
<212> TYPE: PRT
<213> ORGANISM: Artificial sequence
<220> FEATURE:
<223> OTHER INFORMATION: GL3-FR1m VH chain

<400> SEQUENCE: 65

```
Leu Gln Val Gln Leu Gln Gln Ser Gly Pro Arg Leu Val Lys Pro
1               5                   10                  15

Ser Gly Thr Leu Ser Leu Thr Cys Thr Val Ser Gly Gly Ser Ile
                20                  25                  30

Ser Ser Ser Ser Tyr Tyr Trp Gly Trp Ile Arg Gln His Pro Gly
                35                  40                  45

Lys Gly Leu Glu Trp Ile Gly Tyr Ile Tyr Tyr Ser Gly Ser Thr
                50                  55                  60

Tyr Tyr Asn Pro Ser Leu Lys Ser Arg Phe Thr Ile Ser Arg Asp
                65                  70                  75

Asn Ser Lys Asn Thr Leu Tyr Leu Gln Ile Asn Ser Leu Arg Ala
                80                  85                  90

Glu Asp Thr Ala Val Tyr Tyr Cys Ala Arg Leu Gln Gly Ala Arg
                95                  100                 105

Gly Tyr Ser Tyr Gly Tyr Gly Ile Asp Tyr Trp Gly Gln Gly Thr
                110                 115                 120

Leu Val Thr Val Ser Ser Gly Ser Ala Ser Ala Pro Thr Leu Phe
                125                 130                 135
```

```
Pro Ala Ala Ala His His His His His Gly Ala Ala Glu Gln
                140                 145                 150

Lys Leu Ile Ser Glu Glu Asp Leu Asn Gly Ala Ala
                155                 160
```

<210> SEQ ID NO 66
<211> LENGTH: 129
<212> TYPE: PRT
<213> ORGANISM: Artificial sequence
<220> FEATURE:
<223> OTHER INFORMATION: VH3 chain of JL427 VH

<400> SEQUENCE: 66

```
Leu Gln Val Gln Leu Gln Gln Ser Gly Gly Gly Leu Val Gln Pro
1               5                   10                  15

Gly Arg Ser Leu Arg Leu Ser Cys Ala Ala Ser Gly Phe Thr Phe
                20                  25                  30

Ser Ser Tyr Gly Met His Trp Val Arg Gln Ala Pro Gly Lys Gly
                35                  40                  45

Leu Glu Trp Val Ser Tyr Ile Gly Arg Ser Gly Ser His Thr Asn
                50                  55                  60

Tyr Ala Asp Ser Val Lys Gly Arg Phe Thr Ile Ser Arg Asp Asn
                65                  70                  75

Ser Lys Asn Thr Leu Tyr Leu Gln Ile Asn Ser Leu Arg Ala Glu
                80                  85                  90

Asp Thr Ala Val Tyr Tyr Cys Ala Arg Gly Leu Pro Asn Tyr Gly
                95                  100                 105

Met Asp Ile Trp Gly Gln Gly Thr Thr Val Thr Val Ser Ser Gly
                110                 115                 120

Ser Ala Ser Ala Pro Thr Leu Phe Pro
                125
```

<210> SEQ ID NO 67
<211> LENGTH: 160
<212> TYPE: PRT
<213> ORGANISM: Artificial sequence
<220> FEATURE:
<223> OTHER INFORMATION: GL2-CDR1m VH chain

<400> SEQUENCE: 67

```
Leu Gln Val Gln Leu Gln Gln Ser Gly Pro Arg Leu Val Lys Pro
1               5                   10                  15

Ser Gly Thr Leu Ser Leu Thr Cys Thr Val Ser Gly Gly Ser Ile
                20                  25                  30

Ser Ser Tyr Gly Met His Trp Ile Arg Gln His Pro Gly Lys Gly
                35                  40                  45

Leu Glu Trp Ile Gly Tyr Ile Tyr Tyr Ser Gly Ser Thr Tyr Tyr
                50                  55                  60

Asn Pro Ser Leu Lys Ser Arg Val Thr Ile Ser Val Asp Thr Ser
                65                  70                  75

Lys Asn Gln Phe Ser Leu Lys Leu Ser Ser Val Thr Ala Ala Asp
                80                  85                  90

Thr Ala Val Tyr Tyr Cys Ala Arg Leu Gln Gly Ala Arg Gly Tyr
                95                  100                 105

Ser Tyr Gly Tyr Gly Ile Asp Tyr Trp Gly Gln Gly Thr Leu Val
                110                 115                 120

Thr Val Ser Ser Gly Ser Ala Ser Ala Pro Thr Leu Phe Pro Ala
```

```
                    125                 130                 135

Ala Ala His His His His His Gly Ala Ala Glu Gln Lys Leu
            140                 145                 150

Ile Ser Glu Glu Asp Leu Asn Gly Ala Ala
            155                 160

<210> SEQ ID NO 68
<211> LENGTH: 163
<212> TYPE: PRT
<213> ORGANISM: Artificial sequence
<220> FEATURE:
<223> OTHER INFORMATION: GL2-CDR2m VH chain

<400> SEQUENCE: 68

Leu Gln Val Gln Leu Gln Gln Ser Gly Pro Arg Leu Val Lys Pro
1               5                   10                  15

Ser Gly Thr Leu Ser Leu Thr Cys Thr Val Ser Gly Gly Ser Ile
                20                  25                  30

Ser Ser Ser Ser Tyr Tyr Trp Gly Trp Ile Arg Gln His Pro Gly
                35                  40                  45

Lys Gly Leu Glu Trp Ile Gly Tyr Ile Gly Arg Ser Gly Ser His
                50                  55                  60

Thr Asn Tyr Ala Asp Ser Val Lys Gly Arg Val Thr Ile Ser Val
                65                  70                  75

Asp Thr Ser Lys Asn Gln Phe Ser Leu Lys Leu Ser Ser Val Thr
                80                  85                  90

Ala Ala Asp Thr Ala Val Tyr Tyr Cys Ala Arg Leu Gln Gly Ala
                95                  100                 105

Arg Gly Tyr Ser Tyr Gly Tyr Gly Ile Asp Tyr Trp Gly Gln Gly
                110                 115                 120

Thr Leu Val Thr Val Ser Ser Gly Ser Ala Ser Ala Pro Thr Leu
                125                 130                 135

Phe Pro Ala Ala Ala His His His His His His Gly Ala Ala Glu
                140                 145                 150

Gln Lys Leu Ile Ser Glu Glu Asp Leu Asn Gly Ala Ala
                155                 160

<210> SEQ ID NO 69
<211> LENGTH: 108
<212> TYPE: PRT
<213> ORGANISM: Artificial sequence
<220> FEATURE:
<223> OTHER INFORMATION: IgVL2-t VL1 chain

<400> SEQUENCE: 69

Leu Asp Ile Gln Leu Thr Gln Ser Pro Ser Ser Leu Pro Ala Ser
1               5                   10                  15

Val Gly Asp Arg Val Thr Ile Thr Cys Arg Ala Ser Gln Ser Ile
                20                  25                  30

Ser Ser Tyr Leu Asn Trp Tyr Gln Gln Lys Pro Gly Lys Ala Pro
                35                  40                  45

Lys Leu Leu Ile Tyr Ala Ala Ser Ser Leu Gln Ser Gly Val Pro
                50                  55                  60

Ser Arg Phe Ser Gly Ser Gly Ser Gly Thr Asp Phe Thr Leu Thr
                65                  70                  75

Ile Ser Ser Leu Gln Pro Glu Asp Phe Ala Thr Tyr Tyr Cys Gln
                80                  85                  90
```

```
Gln Ser Tyr Ser Thr His Thr Phe Gly Gln Gly Thr Lys Leu Glu
             95                  100                 105

Ile Lys Arg
```

IMMUNOGLOBULINS DIRECTED TO BACTERIAL, VIRAL AND ENDOGENOUS POLYPETIDES

CROSS-REFERENCE TO RELATED APPLICATIONS

This application is a continuation application of U.S. patent application Ser. No. 12/589,440, filed Oct. 23, 2009, now U.S. Pat. 9,969,797, which claims benefit of priority under 35 U.S.C. § 120 of international application PCT/US2008/005221, filed Apr. 23, 2008 which claims benefit of priority of provisional application U.S. Ser. No. 60/913,335, filed Apr. 23, 2007, now abandoned. The entire disclosure of each of the foregoing applications is incorporated by reference herein.

FEDERAL FUNDING LEGEND

This invention was made with government support under grants AI058865, AI067020, AI071951, AI062455 and AG025304 awarded by the National Institutes of Health. The government has certain rights in the invention.

FIELD OF THE INVENTION

This invention relates to the fields of biochemistry, immunology, molecular biology and medicine. More specifically, the invention relates to immunoglobulins and fragments thereof with the ability to hydrolyze or bind to bacterial, viral and endogenous polypeptides and to their preparation and to methods of use thereof.

BACKGROUND OF THE INVENTION

Description of the Related Art

Some immunoglobulins (Igs) have the ability to catalyze chemical reactions through the binding of an antigen, its chemical transformation and the conversion and release of one or more products. Transformation of the chemical structure of antigens by such Igs can induce permanent inactivation of antigens. A single catalytic Ig molecule can hydrolyze thousands of antigen molecules over its biological lifetime, which enhances the biological potency of the catalyst compared to a stoichiometrically binding antibody. Catalytic Igs, therefore, can be developed as potent therapeutic agents capable of removing harmful polypeptide and other classes of antigens. Some Igs contain catalytic sites in their variable (V) domains that have properties similar to the catalytic sites of conventional serine protease class of enzymes. Igs with esterolytic and proteolytic activity have been reported [1-5]. Similarly, some Igs hydrolyze nucleic acids [6,7].

An appreciation of the structural organization of Igs is helpful in understanding the scope of the present invention. A brief review of this aspect follows. Generally, Igs contain light (L) chain and heavy (H) chain subunits. The V domains of these subunits contain the antigen binding site (paratope). Contacts with conventional antigenic epitopes occur mainly at the complementarity determining regions (CDRs) and to a lesser extent the framework regions (FR) of the V domains. The human Ig repertoire, defined as the number of Igs with different antigen binding site structures is estimated at $10^{11}$-$10^{12}$. V domain diversity is generated by the following processes: (a) inheritance of about 50 germline genes each encoding the V domains of L and H subunits; (b) combinatorial diversity brought about by assembly of different L and H chains within the quarternary structure of Igs; (c) junctional diversity generated during recombination of the V and joining (J) gene segments of the L chain, and the V, diversity (D) and J gene segments of the H chain; and (d) rapid mutation occurring in the CDRs over the course of B cell clonal selection, a process entailing antigen binding to Igs expressed as components of the B cell receptor (BCR), and resulting in stimulation of division of the B cells expressing BCRs with the highest binding affinity. An additional level of diversity is offered by the use of different constant domains by Igs, that is, the $\mu$, $\delta$, $\gamma$, and $\alpha$ regions of the H chain and the $\kappa$ and $\lambda$ chains of the L chain. Early in the ontogeny of the immune response, Igs contain $\mu$ or $\delta$ constant regions. Later, isotype switching occurs, and the $\mu/\delta$ regions are replaced by $\gamma/\alpha/\epsilon$ n more differentiated Igs.

Various advances of technology in monoclonal and recombinant Ig techniques have accelerated the identification, selection and purification of catalytic Ig species. One approach to generating catalytic Igs involves immunizing an animal with a stable analog of the transition state of the reaction to be catalyzed and screening for Igs that bind more strongly to the transition state analog than to the corresponding substrate. The Igs, like enzymes, have a site that is complementary to the 3-D and ionic structure of the transition state analog. A large number of Igs synthesized in response to immunization with a transition state analog can bind the analog, but only a small minority will catalyze the reaction of interest. For example, only one catalytic Ig may be found for every 100-1,000 Igs screened. Another major challenge is that the catalytic activity of the Igs can be low compared to the naturally occurring enzymes, usually by a factor of $10^3$ or more.

To be medically useful, the catalytic Ig must also be specific for the desired target antigen. While promiscuous catalytic Igs capable of hydrolyzing polypeptides are common [5,8-10], specific catalytic Igs directed to medically important target proteins are rare. Advances in the field of catalytic Igs, therefore, are dependent on identifying Igs that have high level catalytic activity and the correct epitope specificity enabling specific catalysis directed against the target antigen. The foregoing problems have been recognized for many years. Numerous solutions have been proposed, but none adequately address the problems that must be solved in isolating Igs that have the ability to specifically catalyze medically important biochemical reactions. Renewable and homogeneous sources of well-characterized catalytic Igs are needed for medical applications. A brief review of Ig technologies that may be useful in isolating catalytic Igs follows.

Traditional methods to clone Igs from humans consist of immortalizing lymphocytes derived from peripheral blood (or lymphoid tissues obtained by surgery), for example by transformation with Epstein Barr virus followed by fusion with a myeloma cell lines. The resultant hybridoma cell lines are screened for production of the desired Abs, for example by measuring the binding to a specific antigen by ELISA.

Methods are also available to clone the expressed Ig V domain repertoires in the form of libraries displayed on a suitable surface. The Ab fragments can be cloned as Fab fragments, single chain Fv (scFv) fragments or the L chain subunits. Fab and scFv constructs usually reproduce faithfully the binding activity of full-length Abs (e.g., [11]). Previous reports have documented the antigen binding activity of L chain subunit independent of its H chain partner, albeit at reduced strengths compared to native Abs [12,13]. The V domains of the scFv fragments are usually linked by flexible peptide linkers. Cloning of V domain repertoires is usually accomplished by recovering mRNA from lymphocytes and amplification by the reverse transcriptase-polymerase chain reaction. Mixtures of primers are employed to capture as large a proportion of the expressed repertoire as possible. The primers anneal to comparatively conserved FR1 and FR4 nucleotide stretches located at the 5' and 3' ends of the V domains, respectively, allowing amplification of V domains belonging diverse V gene families. To obtain expressible scFv constructs, the VL and VH domains are cloned into a suitable vector containing a short flexible peptide and an inducible promoter. Peptide tags such as the his6 tag are incorporated into the protein to enable rapid purification by metal affinity chromatography. The length and constitution of the peptide linker is an important variable in ensuring the appropriate intramolecular VL-VH interactions.

The next task is to isolate the minority of individual antigen combining sites with the desired antigen recognition characteristics. This can be accomplished using display technologies [14]. Vectors permitting display of recombinant proteins on the surfaces of phages, retroviruses, bacteria and yeast have been developed. For example, fusion proteins composed of Ig fragments linked to a phage coat protein are expressed from phagemid or phage vectors in bacteria. The recombinant phages display Ig fragments on their surface. The packaged phages contain single stranded DNA encoding the Ig fusion protein. Fractionation of phages based on binding to immobilized antigen yields, therefore, the VL/VH genes of Abs with the desired specificity. Phagemid vectors are useful because a codon at the junction of the Ab and phage coat protein genes is read as a sense codon by bacteria employed to package phages and as a stop codon by bacteria employed to obtain soluble Ab fragments free of the phage coat protein sequence.

Immunotherapeutic agents should preferably have a long half-life to avoid repeated infusions. The half-life of full-length IgG in human circulation is 2-3 weeks, compared to half-lives on the order of minutes for scFv constructs and free Ig L chain subunits. Therefore, various strategies have been developed to increase the stability of Ig fragments in vivo. Examples are the inclusion of a polyethylene glycol molecule at the Ig fragment terminus [15,16] or linkage to the constant region of Igs (Fc) [17]. The V domains can also be routinely recloned in vectors containing the constant domains of heavy and light chains. Expression of these vectors in suitable mammalian cells yields full-length Igs with increased half-life in vivo [18].

The properties of the target antigen are important in the success of medical applications of catalytic Igs. The targeted antigen can be chosen for Ig targeting based on the principles. First, the antigen should fulfill a pathogenic role. For example, the targeted antigen may interfere in some essential endogenous cellular or metabolic function. Alternatively, in the case of microbial antigens, the antigen should be important for growth of the microbe or it may be important in diverting host immune responses away from protection against the microbe. Second, removal of the antigen by Igs should not be associated with a deleterious side effect. This is particularly important in targeting of an endogenous antigen by Igs, e.g., amyloid β peptide in Alzheimer disease, as most endogenous antigens fulfill useful biological functions. In the case of microbial antigens, the danger of cross-reaction with endogenous antigens should be minimized. Immune complexes of antigens with Igs containing Fc regions have the potential of reacting with Fc receptors expressed on inflammatory cells and inducing undesirable inflammatory reactions. This danger is minimized if the Ig has catalytic activity, as the longevity of the immune complexes is reduced due to antigen chemical transformation and product release.

Examples of antigens suitable for Ig targeting are presented below.

Amyloid β Peptide (Aβ)

Aβ is the target of conventional non-catalytic Igs in ongoing clinical trials for the treatment of Alzheimer disease. A monoclonal IgG [19] and pooled polyclonal IgG from healthy humans [20] are under trial. The rationale for Aβ targeting is as follows. In 1907 that the first pathological lesion associated with dementia, the cerebral plaque, was reported by Alzheimer [21]. The cerebral lesion was called an "amyloid" plaque because iodine, which stained the cerebral plaque, also stains starch. The true chemical composition of the "amyloid" plaque was elusive until 1984 when Glenner and Wang discovered a means to solubilize the cerebral plaques in Alzheimer's disease (AD) and showed that they are composed principally of peptides Aβ1-40 and Aβ1-42. These peptides are identical but for the two additional amino acids, Ile and Ala, at the C-terminus of Aβ1-42 [22]. Both peptides are derived by proteolytic processing of the larger amyloid precursor protein (APP), which is composed of 770 amino acids and has the characteristics of a transmembrane protein [23]. APP is cleaved by β and γ secretases, releasing the Aβ peptides [24,25]. The role of Aβ peptides in the pathogenesis of AD is supported by findings that: (a) Familial AD is associated with mutations in the APP gene or the secretase genes; (b) Transgenic mice, expressing mutant human, APP genes develop an age-associated increase in cerebral Aβ peptides and amyloid plaques as well as cognitive decline [26,27]; (c) Mutant, human APP-tg mice that do not process APP to Aβ show no cognitive decline, suggesting that increased Aβ peptides and not the mutant APP is responsible for cognitive decline [28,29]; and (d) Synthetic Aβ peptides and their oligomers are neurotoxic in vitro [30,31].

HIV gp120

Igs directed to the HIV coat glycoprotein gp120 have been under consideration for immunotherapy of HIV infection. A key step in HIV infection is the binding of gp120 to host cell CD4 receptors. Additionally, gp120 plays a significant role in viral propagation and demonstrates a toxic effect on cells that are not infected with HIV [32,33]. gp120 is toxic for neurons, it facilitates lyses of lympocytes by an antibody-dependent mechanism, and it increases the binding of complement components to cells [34-39]. It has been shown that monoclonal Igs can bind the CD4 binding site (e.g., [40,41]). However, gp120 expresses many antigenic epitopes, and the immunodominant epitopes are located in the variable regions of gp120. Igs to the immunodominant epitopes do not neutralize diverse strains with varying sequence of the variable gp120 regions. Igs to the conserved gp120 sequences are necessary for therapy of HIV infection. Such Igs can also be used as topical microbicides to prevent vaginal and rectal transmission of HIV via sexual intercourse. gp120 contains a B cell superantigenic epitopes, defined as an antigenic epitope to which Igs are present in the preimmune repertoire without the requirement of adaptive immune specialization [42]. Residues 421-433 of this epitope are also important in CD4 host receptor binding [43,44]. Igs to the superantigenic epitope hold the potential of neutralizing HIV broadly. However, superantigens are thought to be recognized mainly by conserved regions of Ig V domains, including the conserved regions of the FRs and CDRs. Adaptive improvement of the superantigen recognition function appears to be difficult. No monoclonal or polyclonal Igs with the ability to neutralize the entire range of HIV strains belonging to various clades are available.

Staphylococcus aureus

This bacterium is an opportunistic pathogen that colonizes the skin (primarily the anterior nasal vestibule) of approximately 30-50% (with 20-30% persistently colonized) of the population without causing clinical disease symptoms [45, 46]. Persistently colonized individuals are designated 'carriers'. Certain antibiotics are available for the treatment of S. aureus-caused disease, but the number of antibiotic-resistant strains is increasing rapidly. Host immunological factors play a role in determining susceptibility to initial colonization and development of S. aureus disease. However, certain virulence factors produced by S. aureus can downregulate host immune defenses profoundly, helping the bacterium colonize various anatomic sites and cause serious disease. The protective effect of Igs directed against S. aureus antigens has been reported in several experimental studies [47-49]. Persistent antigenic exposure in S. aureus carriers can be hypothesized to induce adaptive synthesis of protective Igs. An insufficient adaptive response may be a predisposing factor in progression of infection. As noted above, certain microbial antigens behave as B cell superantigens. If S. aureus proteins have superantigenic character, protective Igs to the bacterium may be produced spontaneously without prior infection. S. aureus produces a host of virulence factors important in bacterial adhesion, toxicity for host cells and modulation of the host immune system. Selected S. aureus suitable for targeting by Igs are listed in Table 1.

TABLE 1

Example S. aureus proteins suitable for targeting by Igs

| S. aureus proteins | Function |
|---|---|
| Efb | Immune Impairment |
| Protein A | Immune Evasion |
| Map19 (Eap) | Immune Impairment |
| ClfA$_{229-54}$ | Fibrinogen/Fibronectin Adhesin |
| ClfB$_{201-542}$ | Fibrinogen/Cytokeratin Adhesin |
| FnbpA | Fibronectin Adhesin |
| CAN | Collagen Adhesin |
| SdrE$_{51-606}$ | Potential Adhsin |
| Alpha toxin | Toxin |
| LukF | Toxin |
| LukS | Toxin |

Hepatitis C Virus (HCV)

It is estimated that over 170 million people worldwide are infected with HCV [50]. HCV genotypes 1a, 1b, 2a and 2b are common in the United States. The mainstay of current therapy is a combination of interferon and ribavirin, which leads to clinical improvement in a subpopulation of patients with chronic HCV infection. Clearly, more strategies are needed for treatment and prevention of HCV infection [51]. The E2 coat protein expressed by HCV is thought to be essential for viral infection by virtue of its role in host cell binding [52]. E2 contains hypervariable regions and comparatively conserved regions. Igs to the hypervariable regions are frequent in infected individuals [53]. Conventional non-catalytic Igs to E2 may be important in control of virus infection [53]. Certain monoclonal Igs to E2 neutralize the virus and [54] are under consideration for therapy of HCV infection.

Thus, there is a recognized need in the art for improved immunoglobulins that hydrolyze or bind to bacterial, viral and endogenous polypeptides. More specifically, the prior art is deficient in immunoglobulins and monoclonal antibodies derived therefrom comprising one or two immunoglobulin variable chain domains with an enhanced antigen-defined catalytic or binding ability. The present invention fulfills this long-standing need and desire in the art.

SUMMARY OF THE INVENTION

The present invention describes several classes of Ig fragments that display high level catalytic and binding activities and the desired bioactivity profiles. Thereby, the invention addresses the need for improved compositions and methods for the preparation of antibodies that can be used for medical applications.

One class of Ig fragments in the present invention consists of single domain VL constructs (IgV$_L$ constructs) that contain a peptide tag (designated t) at their termini. The structure of the terminal t region can be varied without loss of IgV$_L$ function). The purpose of including the t region is to interfere with noncovalent V domain association and maintenance in monomeric form. The invention discloses the unanticipated finding that the monomeric form of the VL domains expresses superior catalytic activity compared to physiological Ig combining sites composed of paired VL domain-VH domain structures.

Another class of Ig fragments in the present invention consists of two domain V$_L$-V$_L$ constructs (IgV$_{L2}$ constructs) expressing superior catalytic activity compared to physiological Ig combining sites. Evidently, pairing of two VL domains is more permissive for expression of catalytic activity compared to pairing of a VL domain with a VH domain. Optionally, the t region can contain peptide or non-peptide structures that direct the IgV to the desired target anatomic site. For example, inclusion of polyanionic compound such as a putrescine in the t region can facilitate passage of the IgV across the blood-brain-barrier.

In another embodiment, the present invention describes the composition and properties of IgVs directed to amyloid β peptide (A_β), S. aureus virulence factors and HIV gp120 identified by screening and fractionation of libraries composed of a large number of IgV constructs. The IgVs can be identified by random screening of a plurality of the IgV clones for the desired antigen recognition activities. Alternatively, the antigen or analogs of the antigen containing an electrophilic group can be used to fractionate phage displayed IgVs to isolate the IgV species with greatest activity. These methods can be employed to yield IgVs which recognize the antigen by noncovalent means or IgVs that catalyze the hydrolysis of the antigen.

Another embodiment of the invention concerns recognition of B cell superantigens by the V domains, which is thought to occur mainly at conserved V domain residues. Swapping of the framework regions (FRs) or complementarity determining regions (CDRs) of the VH domains by corresponding FRs or CDRs drawn from other V domains is shown to improve B cell superantigen recognition capability. Similarly, mutations introduced at individual amino acids in the FRs or CDRs can be employed to improve the ability of IgVs to recognize B cell superantigens.

The IgVs can be engineered further to improve their stability in vascular circulation and other anatomic sites, for example by linkage to a polyethylene glycol molecule or the Fc region of Igs. Aslo disclosed are novel full-length catalytic IgGL and IgML molecules containing antigen combining sites composed of 2 VL domains instead of one VL domain and one VH domain. These molecules contain a VL domain is grafted in place of the VH domain within the heavy chain subunit, along with the VL domain contained in the light chain subunit.

Another embodiment of the invention consists of identifying polyclonal Igs from blood and mucosal secretions with enriched catalytic activity. The catalytic activity is directed to one or more protein, e.g., an *S. aureus* virulence factor, the HCV coat protein E2, the HIV coat protein gp120 or Aβ. For example, the invention discloses findings of HIV neutralization by long-term survivors of HIV infection that are a suitable source of pooled Igs for treatment and prevention of HIV infection. Likewise, screening of human donors has revealed highly variable levels of catalytic Igs directed to *S aureus* virulence factors and HCV E2. Pooled Igs from donors expressing high level catalytic activities to the appropriate antigens are conceived to be useful in various medical treatments, including treatment of antibiotic-resistant *S. aureus* infection, HCV infection and Alzheimer disease.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 2A-2B illustrate IgV screening for $^{125}$I-Aβ40 hydrolysis. In FIG. 2A sixty three IgVs purified from randomly picked clones in our human IgV library were analyzed. Each point represents one clone. $^{125}$I-Aβ40, 0.1 nM; 18 h. In FIG. 2B bacteria were transformed with phagemid DNA from clone 2E6, the highest activity clone in panel (A). Shown are specific activities for 15 IgV preparations purified from 15 individual colonies along with the identically purified empty vector control (pHEN2; closed triangle).

FIG. 3A shows the structure of E-Aβ40 used for phage selection. The electrophilic phosphonate groups placed within Aβ40 epitopes permit specific covalent binding to Igs displaying the nucleophilic reactivity coordinated with noncovalent Aβ40 recognition. In FIGS. 3B-3C phages in the IgV library (10$^7$ clones) were allowed to bind biotinylated E-Aβ40 (2 or 10 μM), and bound phage particles were captured with immobilized anti-biotin antibodies. Phages associated noncovalently with E-Aβ40 were retrieved by elution with excess nonbiotinylated Aβ40 (100 μM; noncovalent selection). Covalently bound phages were retrived by elution with an acidic buffer (pH 2.7; covalent selection). Hydrolysis of $^{125}$I-Aβ40 (0.1 nM) by IgVs obtained from noncovalently and covalently selected phages is shown in panels B and C, respectively. Each point represents an individual IgV clone.

In FIG. 4B, lanes 1 and 2, respectively, are silver stained and anti-c-myc antibody stained gels of IgV$_{L2}$-t 2E6 after two cycles of metal affinity chromatography. Lanes 3 and 4, respectively, are silver stained and anti-c-myc antibody stained gels of IgV$_{L2}$-t 2E6 after further chromatography on the FPLC Mono Q column (fractions corresponding to retention times 10-11 min). Lanes 5 and 6, respectively, are silver stained and anti-c-myc antibody stained gels of IgV$_L$-t' 5D3 after two cycles of metal affinity chromatography. Lanes 7 and 8, respectively, are silver stained and anti-c-myc antibody stained gels of IgV$_L$-t' 5D3 after further chromatography on the Mono Q column (fractions corresponding to retention times 23-23.5 min).

FIG. 5 shows the deduced IgV amino acid sequences. VH and VL CDRs are underlined. The linker is shadowed. Tag t, the his6-c-myc tag is in italics. The polypeptide at the C terminus of the VL domain in IgV$_L$-t' clone 5D3, 1E4 and 5H3 is designated tag t'. Tag t' in each of these clones is composed of the expected N terminal 17 residue linker, an aberrant 15-28 residue intervening peptide sequence and the expected C terminal 26 residue his6-c-myc tag t. The aberrant peptide sequences in the IgV$_L$-t' clones are composed of: clone 5D3, VH FR1 residues 1-7 linked to CH1 residues 116-123; clone 1E4, VH FR1 residues 1-9, an unidentified 17 residue peptide and CH1 residues 122-123; clone 5H3, VH FR1 residues 1-2, an unidentified 9 residue peptide and CH1 residues 118-123. The unidentified peptide regions were not derived from any known protein as determined by Blast homology searches.

FIG. 6A shows the exceptional catalytic activity of IgV$_{L2}$-t 2E6 and IgV$_L$-t' 5D3 compared to previously known Aβ hydrolyzing IgMs and Ig light chain subunits. Shown are the Aβ40 hydrolysis activity (fmol/h/mg Ig; means of duplicates) of monoclonal IgM Yvo (405 μg/ml), a pooled polyclonal IgM preparation (90 μg/ml), L-t C23.5 (15 μg/ml), L-t HK14 (3.4 μg/ml), IgV$_{L2}$-t 2E6 (0.55 μg/ml) and IgV$_L$-t' 5D3 (0.075 μg/ml). $^{125}$I-Aβ40, ~30000 cpm (~0.1 nM). The monoclonal and polyclonal IgM preparations are described in Taguchi H, et al, J Biol Chem 2008, 283, 4714; L-t HK14 is described in Liu R, et al, Biochemistry 2004, 43, 9999. FIG. 6B shows the isolation of catalytically improved IgV$_{L2}$-t 2E6 mutants. A random mutant library containing ~4 amino acid mutations/IgV$_{L2}$-t molecule was generated by error-prone mutagenesis. Following covalent selection of mutants expressed on phages using E-Aβ, secreted IgV$_{L2}$-t mutants in culture supernatants of individual bacterial colonies (1:75 diluted) were screened for Aβ hydrolysis. Values are corrected for background activity observed in supernatants from empty vector control colonies. Ig concentrations were estimated by c-myc dot blots. Shown are values of $^{125}$I-Aβ40 (0.1 nM) hydrolysis (means of duplicates) incubated (18 h) with culture supernatants of 143 clones obtained by covalent selection. The red data point corresponds to wildtype IgV$_{L2}$-t 2E6 hydrolytic activity.

FIG. 7 shows the deduced amino acid sequences of various derivatives of IgV$_L$-t' 5D3, i.e., the repaired scFv-t, full-length L-t and homodimeric IgV$_{L2}$-t. For the 4 scFv-t constructs, only VH domain sequences are shown. The scFv-t constructs contain an identical VL domain derived from IgV$_L$-t' 5D3 (see sequence in FIG. 5). CDRs are underlined, linker is shadowed and the His6-c-myc tag is in italics.

In FIG. 8A $^{125}$I-Aβ40 (~30000 cpm, ~0.1 nM) is incubated in duplicate for 18 h with IgV$_L$-t' 5D3 (0.075-1.9 µg/ml) and four scFv-t 5D3 variants (2.5-10 µg/ml). FIG. 8B shows SDS-PAGE gels showing purified IgV$_L$-t' (lane 1) and scFv-t (lane 3) stained with silver. Lanes 2 and 4 show, respectively, the IgV$_L$-t' and scFv-t stained with anti c-myc antibody. The bands at 18 kDa and 30 kDa represent, respectively, the IgV$_L$-t' and scFv-t. FIG. 8C shows $^{125}$I-Aβ40 hydrolysis activities of L-t 5D3 and IgV$_{L2}$-t 5D3 assayed as in FIG. 8A (means of 3 independent assays).

FIGS. 9A-9E are mass spectra of Aβ40 and Aβ42 peptide bonds hydrolyzed by IgV$_{L2}$-t 2E6. MALDI-TOF mass spectra of Aβ40 incubated for 89 h in diluent (89 h) (FIG. 9A) or with IgV$_{L2}$-t 2E6; (FIG. 9B) and Aβ42 incubated similarly in diluents (FIG. 9C) or IgV$_{L2}$-t 2E6 (FIG. 9D). Aβ40 or Aβ42, 100 µM; IgV$_{L2}$-t 2E6, 1 µM. Spectra were collected using _α-cyano-4-hydroxy cinnamic acid as matrix (positive ion mode, 20,000 volts). Peak numbers in the spectra indicate: 1, Aβ 1-14 (calculated (M+H)$^+$=1698.7, observed (M+H)$^+$=1698.8); 2, Aβ 1-15 (calculated (M+H)$^+$=1826.8, observed (M+H)$^+$=1826.9); 3, Aβ 21-40 (calculated (M+H)$^+$=1886.0, observed (M+H)$^+$=1886.1); 4, Aβ 1-20 (calculated (M+H)$^+$=2461.2, observed (M+H)$^+$=2461.2); 5, Aβ 16-40 (calculated (M+H)$^+$=2520.4, observed (M+H)$^+$=2520.4); 6, pGluA_β 15-40 (calculated (M+H)$^+$=2631.4, observed (M+H)$^+$=2631.5); 7, Aβ 15-40 (calculated (M+H)$^+$=2648.5, observed (M+H)$^+$=2648.5); 8, Aβ40 (calculated (M+H)$^+$=4328.2, observed (M+H)$^+$=4328.1); 9, Aβ 15-29 (calculated (M+H)$^+$=1638.9, observed (M+H)$^+$=1638.9); 10, Aβ 15-28 (calculated (M+H)$^+$=1581.8, observed (M+H)$^+$=1581.8); 11, Aβ 21-42 (calculated (M+H)$^+$=2070.1, observed (M+H)$^+$=2070.2); 12, pGluAβ 15-42 (calculated (M+H)$^+$=2814.6, observed (M+H)$^+$=2814.8); 13, Aβ 15-42 (calculated (M+H)$^+$=2832.6, observed (M+H)$^+$=2832.6); 14, Aβ 42 (calculated (M+H)$^+$=4512.3, observed (M+H)$^+$=4512.1). FIG. 9E shows the major (big arrows) and minor (small arrows) hydrolytic sites in Aβ40 and Aβ 42.

In FIG. 11A E-hapten-1 is an active site-directed inhibitor of trypsin-like serine proteases. E-hapten-2 is a biotinylated analog of E-hapten-1 employed to detect covalent IgV adducts by streptavidin-peroxidase staining of SDS-electrophoresis gels. E-hapten-3 is the unesterified phosphonic acid analog of E-hapten-1 devoid of covalent reactivity. FIG. 11B shows inhibition of IgVL2-t 2E6 and IgVL-t' catalyzed $^{125}$I-Aββ40 hydrolysis by E-hapten-1. IgVL2-t 2E6 (0.55 µg/ml) or IgVL-t' 5D3 (0.075 µg/ml) was preincubated with E-hapten-1 (0.01, 0.5 and 1 mM) for 2 h with followed by determination of 125I-Aβ hydrolytic activity. FIG. 11C shows Streptavidin-peroxidase stained blots of SDS electrophoresis gels showing IgV$_{L2}$-t 2E6 (20 µg/ml) incubated for 18 h with E-hapten 2 (0.1 mM, lane 2) or E-hapten-3 (lane 3). Lane 1, silver-stained SDS-gel of IgV$_{L2}$-t 2E6

FIG. 12A shows streptavidin-peroxidase stained blots of reducing SDS-gels containing IgV$_{L2}$-t 2E6 (1 µM) or diluent. Lanes 1, 3, 5, 7, and 9 show 26E reacted with biotinylated (Bt-) gp120, soluble epidermal growth factor receptor (sEGFR), bovine serum albumin (BSA), protein A and ovalbumin (OVA) (0.1 µM; 18 h), respectively. Lanes 2, 4, 6, 8, and 10 show diluent reacted with Bt-gp120, sEGFR, BSA, protein A, and OVA, respectively. FIG. 12B show anti-GST-peroxidase stained blots of SDS-gels containing amphiphysin (AMPH) and zinc finger protein 154 (ZNF154). Lanes 1 and 2 are AMPH with diluent and with IgV$_{L2}$-t 2E6 and lanes 3-4 are ZNF154 with diluent and with IgV$_{L2}$-t 2E6. GST-proteins, 0.1 µM; 2E6, 1 µM; incubation, 18 hours at 37° C. No appreciable hydrolysis of the intact proteins was detected.

In FIG. 19A Bt-Efb (0.1 µM) was incubated in the presence of purified antibody fragments at 37° C. for 20 h. Shown are % Bt-Efb cleavage determined as % decrease of Bt-Efb band intensity compared to the diluent control. FIG. 19B are streptavidin-peroxidase-stained blots of reducing SDS-PAGE gels demonstrating cleavage of Bt-Efb following incubation with 2 of 46 clones tested (scFv-t 1C7 and scV$_{L2}$-t 1B4). The scFv-t 1C9 clone is a representative non-catalytic clone. Reaction volume, 0.02 ml. Diluent lane, Efb incubated in the absence of antibody fragment.

FIGS. 20A-20B depicts the nucleotide and amino acid sequences of scFv-t 1C9. Illustration: Schematic representation of the domain organization of scFV-t 1C9; $V_L$ and $V_H$ domains are linked by the peptide linker, and the tag containing a His6 motif and c-myc peptide is located at the C-terminus of the molecule. In sequences, "." and "-" indicate, respectively, a 1C7 nucleotide and amino acid identical to the corresponding position of the closest germline sequence.

FIGS. 21A-21B depicts the nucleotide and amino acid sequences of IgV$_{L2}$-t 1B4. Illustration: Schematic representation of the domain organization of IgV$_{L2}$-t 1B4; Two different V$_L$ domains are linked by the peptide linker, and the tag containing a His6 motif and c-myc peptide is located at the C-terminus of the molecule. In sequences, "." and "-" indicate, respectively, a 1B4 nucleotide and amino acid identical to the corresponding position of the closest germline sequence.

FIGS. 22A-22B illustrate the effect of catalytic IgG on C3b binding and Efb-mediated complement inhibition. FIG. 22A is a Western-C3b ligand blot analysis of CIg-treated Efb. Pooled IgG from twelve healthy adult subjects was incubated with Efb and subjected to SDS-PAGE (10% tricine gel), transferred onto nitrocellulose paper and probed with digoxigenin-labeled C3b as described, followed by a second incubation with alkaline phosphatase-labeled anti-digoxigenin Fab fragments. In FIG. 22B Efb (0.1 µM) was preincubated in absence or presence of varying concentrations of pooled IgG for 20 h at 37° C. in 50 mM Tris·HCl, 100 mM glycine, 0.1 mM CHAPS, pH 8.0, containing 67 µg/ml gelatin. Reaction volume, 20 µl. The "high reference serum" (5 µl) provided as part of the CH50 complement assay (Diamedix) was added to each Efb-IgG mixture for 1 h. Positive control was 5 µl of high reference serum added to 20 µl PBS and preincubated as above. Each reaction mixture was subsequently added to tubes containing antibody-coated RBCs, vortexed and incubated at room temperature for 1 h as instructed by manufacturer. A tube with no high reference serum served as a negative control. RBC lysis via the classical pathway was quantified by measuring absorbance ($A_{415}$) after the tubes were centrifuged. The data are plotted relative to the observed lysis in the positive control "high reference serum" tubes (no Efb, no IgG; 100% value) using the equation 100×($A_{415}$ of Sample (Efb alone or Efb+IgG)/$A_{415}$ of positive control.

FIGS. 23A-23C illustrate the hydrolysis of Bt-SdrE, Bt-I-Protein A, and ClfA by human Ig. In FIG. 23A Bt-SdrE (0.1 µM) was incubated in the presence of purified pooled IgA (1 µM, 15 h) from healthy adult volunteers. In FIG. 23B Bt-I-Protein A (0.1 µM, 17 hours) was incubated with increasing concentrations of human serum IgA pooled from healthy individuals (Lane 1, 0 µg/ml; Lane 2, 32 µg/ml; Lane 3, 160 µg/ml; Lane 4, 600 µg/ml). Reaction mixtures were then subjected to SDS-PAGE electrophoresis visualized by streptavidin-peroxidase staining. In FIG. 23C ClfA (0.1 µM) was incubated in the presence of 1 µM pooled IgG from healthy individuals for 15 h and then run on a 15% tricine gel and silver stained.

FIG. 25A is a scatter plot depicting Efb hydrolysis by IgG from healthy children and S. aureus infected children Each symbol represents the Efb hydrolyzing activity (mean of duplicates) of an IgG sample. Efb hydrolyzing activity was measured by SDS electrophoresis assay using Bt-Efb as substrate as in FIG. 14. (IgG, 150 µg/mL; Bt-Efb, 100 nM; 18 h incubation). FIG. 25B shows the selective Efb hydrolysis by IgG from aseptic mice (pool of 10). Hydrolysis of Bt-Efb, Bt-sEGFR, Bt-OVA and Bt-BSA was measured as in FIG. 25A. FIG. 25C shows streptavidin-stained blots of SDS electrophoresis gel lanes showing Bt-Efb (100 nM) incubated with diluent or IgG (150 µg/mL) for 24 h at 37° C. FIG. 25D shows the Efb hydrolyzing activity of IgG from mice infected by S. aureus and noninfected controls. Mice (n=5) were inoculated with S. aureus (strain USA300; 1×10$^8$ in 50 µl phosphate buffered saline, pH 7.4) by intradermal injection and the mice were bled from the tail vein. IgG, 100 µg/ml, 18 h.

FIG. 26A shows time-dependent degradation of E2-GST by IgM. E2-GST (10 µg/mL) was incubated with a pooled IgM preparation (25 µg/mL) from sera of HCV infected subjects. Shown are anti-GST-peroxidase stained blots of SDS-gels revealing the reduction of the intact E2-GST band intensity as a function of incubation time. Multiple cleavage products were detected as anti-GST stainable bands with mass values smaller than the 70 kD E2-GST band. FIG. 26B shows E2-Flag hydrolysis by IgM. Shown are anti-E2 stained blots of SDS-gel of E2-Flag incubated as in panel A in the presence (left two lanes) or absence (right two lanes) of IgM. FIG. 26C shows E2-GST cleaving activity of IgM from humans with and without HCV infection. E2-GST incubated with IgM as in FIG. 26A (48 h) was subjected to SDS-electrophoresis and anti-GST staining as in FIG. 26A. E2-GST hydrolysis was quantified by measuring the reduction of the intact E2-GST band by densitometry in reference to the diluent control. Each point represents one study subject. FIG. 26D shows E2-flag cleaving activity of IgM from humans with and without HCV infection. E2-flag was incubated with IgM and E2-flag cleavage determined as in panel C. Each point represents one study subject.

FIGS. 29A-29D illustrate the MALDI-TOF mass spectra of E2-GST (FIG. 29A), biotinylated E2-GST (FIG. 29B) and E2-E-GST (FIG. 29C). FIG. 29D are structures and expected mass increments for biotinamidohexanoyl (Bt unit) and phosphonate groups.

FIG. 30A shows gp120 hydrolysis by IgAs from HIV negative subjects. Plot shows proteolytic activity per unit time and per unit Ig mass. Shown are data from serum Igs and salivary IgA (sIgA) from 4 humans and 4 commercial IVIG preparations. FIG. 30B shows streptavidin-peroxidase stained reducing SDS-gels showing biotinylated gp120 treated with diluent (lane 1) or salivary IgA (lane 2). Lanes 3 and 4 show, respectively, covalent adducts of E-421-433 and E-hapten formed by a monoclonal human IgM, code 1801. FIG. 30C shows the neutralizing potency of IgA and IgG Abs purified from pooled serum or saliva. HIV-1 strain, 97ZA009; host cells, PBMCs. Values are relative to p24 concentrations in test cultures receiving diluent instead of Igs. Serum IgA showed neutralizing activity after 24 h incubation with the virus (not shown).

FIGS. 33A-33D illustrate HIV neutralization by specific IgAs to 416-433 epitope purified by epitope-specific affinity chromatography. FIG. 33A depicts the structure of E-416-433 used for covalent affinity chromatography. FIG. 33B shows reduced neutralizing activity of IgA ($LTS_{19-21}$ donor 2866) immunoadsorbed with BSA-E-416-433. Values are means±s.e.m. of 4 cultures. Dashed lines, 95% confidence limit. P value computed versus IgA immunoadsorbed with control albumin, Student's t-test. FIG. 33C shows improved neutralizing activity of epitope-specific pooled IgA fractions ($LTS_{19-21}$ donors 2857, 2866 and 2886) ●, non-covalently bound fraction ■ and covalently bound IgA ○. FIG. 33D shows an association of 416-433 epitope mutations with reduced IgA neutralizing potency. IC50 values of the three $LTS_{19-21}$ IgA preparations for strains without and with mutations at individual amino acid positions were compared using the 2-tailed Student's t-test. (_) $IC_{50}$ for strains with the indicated consensus clade C residue. (_) $IC_{50}$ for strains with the indicated mutation.

FIGS. 34A-34B illustrate the isolation of nucleophilic antibody L chain subunits that recognize gp120 residues 421-433 from a phage-displayed human L chain library. FIG. 34A E421-433 and 421-436 structures. FIG. 34B gp120 hydrolyzing activity of L chains selected using E-421-433 or 421-436. For selection methods, see text. The activity was measured using biotinylated gp120 (100 nM) as substrate and expressed as the intensity of the 55 kD product band intensity (P55; in arbitrary volume unit, AVU) determined by densitometry of streptavidin-peroxidase stained blots of SDS-electrophoresis gels.

FIGS. 35A-35C depicts the amino acid sequences of VL domains of L chains SK18, SK45 and SKL6.

FIG. 36A: E-gp120 structure. FIG. 36B: gp120 hydrolyzing activity of IgVs. For selection methods, see text. The activity was measured using biotinylated gp120 (100 nM) as substrate and expressed as the 55 kD product band intensity (P55; in arbitrary volume unit, AVU) determined by densitometry of streptavidin-peroxidase stained blots of SDS-electrophoresis gels.

FIGS. 37A-37C illustrates the catalytic and neutralizing activities of lupus scFv-t clones. FIG. 37A shows streptavidin-peroxidase stained blots of SDS-gels showing cleavage of Bt-gp120 (0.1 µM) by purified scFv-t clones GL2 and GL59 (20 µg/ml). scFv-t 1B8 analyzed in parallel is devoid of catalytic activity. FIG. 37B shows HIV neutralization (strain ZA009) by scFv-t clones. Host cells: PBMCs. FIG. 37C shows Inhibition of scFv-t neutralizing activity by E-421-433. scFv-t JL427 (0.24 µg/ml) preincubated for 24 h with E-421-433 (100 µM, see structure in inset) or the control electrophilic peptide E-VIP before assay of neutralizing activity and PBMC. Inset, streptavidin stained blot of SDS-gel showing formation of scFv-t JL427 adducts with E-421-433 (lane 2; 30 kD) and absence of adducts with E-VIP (lane 1).

FIG. 38A-38E are schematic representations of the structures and amino acid sequences of IgVs. FIGS. 38A-38B: scFv-t clones GL2, GL59, JL427, JL606 and JL678. FIG. 38C: $IgV_{L2}$-t clone GL1. FIG. 38D $IgV_H$-t clone JL683. FIG. 38E IgVL-t' clone JL651. In JL651, tag t' corresponds to the linker, an aberrant polypeptide in place of the VH domain at the C terminus of the linker and the His6-c-myc tag.

FIG. 39 depicts schematic representations of the VH domain structures and amino acid sequences of FR-swapped mutants of scFv-t GL2. Black and white boxes, respectively, are regions derived from scFv-t JL427 and scFv-t GL2. All mutants tested contained the VL domain of scFv-t GL2.

FIG. 41A is a depiction of Aβ binding IgG. FIG. 41B is a depiction of Aβ hydrolyzing IgM. FIG. 41C is a depiction of Aβ hydrolyzing IgGL. FcRn: neonatal Fc receptor. FcRμ/α: Fc receptor for IgM. LRP-1: low-density lipoprotein receptor related protein 1; RAGE: receptor for advanced glycation end products.

FIGS. 42A-42C illustrate brain Aβ depletion by $IgV_{L2}$-t 2E6. FIG. 42A shows a comparison of plaques in brain cortex with (left cortex) and without (right cortex) catalytic $IgV_{L2}$-t 2E6 (1_g) seven days post-injection. Aβ plaques were quantified relative to the total area examined. **P<0.01, unpaired t test, $IgV_{L2}$-t 2E6 injected versus non-injected hemispheres. FIG. 42B shows the failure of noncatalytic $IgV_{L2}$-t MMF6 to reduce Aβ plaques (n=4 mice). Data are relative to non-injected hemispheres. Procedures were as in FIG. 42A. FIG. 42C are photomicrographs of right cortex sections following injection with PBS (top) or catalytic $IgV_{L2}$-t 2E6 (bottom) stained with the anti-Aβ antibody. Non-injected left cortex controls are included.

DETAILED DESCRIPTION OF THE INVENTION

Figure 1:
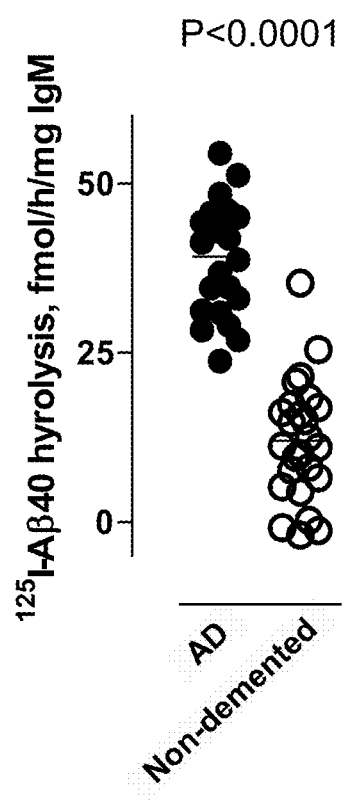
FIG. 1 illustrates increased Aβ hydrolysis by IgMs from patients with Alzheimer's disease. Shown are values of $^{125}$I-Aβ40 (0.1 nM) hydrolysis (means of duplicates) incubated for 68 h with the IgM preparations (0.023 mg/ml) purified from AD patients (n=23) and elderly, non-demented control subjects (n=25). Hydrolytic activity was determined by separation of intact and degraded peptide by precipitation with trichloroacetic acid as in Taguchi H, et al, J Biol Chem 2008, 283, 4714. Values of Each point represents a different human subject. 2-tailed unpaired t-test is utilized.

As used herein, the term "a" or "an", when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, method steps, and/or methods of the invention. It is contemplated that any compound, composition, or method described herein can be implemented with respect to any other device, compound, composition, or method described herein.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "Ig" in the claims refers to any immunoglobulin of the IgM, IgG and classes.

As used herein, the term "IgV" in the claims refers to any variable domain of the light c and heavy chain Ig subunits with and without incorporation of additional sequences at the termini of the V domains.

As used herein, the term "tag" in the claims refers to any polypeptide or non-peptide incorporated at the terminus or within the V domain or combination of V domains.

As used herein, the term "single domain IgV" refers to a V domain that can fulfill the antigen recognition function in the absence of a second full-length V domain.

As used herein, the term "two domain IgV" in the claims refers to a combination of two V domains that can recognize the antigen.

As used herein, the term "antigen recognition" refers to the ability to bind the antigen by noncovalent means or covalent means or the ability to catalyze the chemical transformation of the antigen.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the catalytic antibody to be administered, its use in the pharmaceutical preparation is contemplated.

In one embodiment of the present invention, there are provided classes of IgVs with high level catalytic and binding activities and the desired bioactivity profiles. The structure and properties of the IgVs are exemplified by their reactivities with various antigens of medical interest. Optionally, the IgVs can be isolated from humans with the autoimmune disease systemic lupus erythematosus. Other suitable sources of the IgVs are humans without disease and humans with Alzheimer disease, *S. aureus* infection, HIV infection or HCV infection. For example, humans with Alzheimer disease produce Igs with specificity for Aβ peptide. Consequently, such humans are suitable for isolating IgVs directed to Aβ.

The invention discloses several IgVs that catalyze the hydrolysis of Aβ isolated from a library of IgVs derived from lupus patients. The library consists mostly of two domain IgVs containing paired VL-VH antigen combining sites. However, a minority of clones are structurally aberrant because of imprecision of cloning methods used for generating the library. The aberrant structures include IgVs containing two VL domains (designated IgVL2-t constructs wherein t denotes a short peptide tag included in the IgVs to help identify and purify the recombinant proteins) and IgVs with a single VL domain linked to non-natural polypeptides at the C terminus, e.g., short VH domain sequences containing large internal deletions (designated IgVL-t' wherein t' denotes the tag region encompassing the aberrant structure at the terminus the VL domain). Random screening methods along with the use of an electrophilic Aβ analog to isolate IgVs with greatest nucleophilic reactivity permitted isolation of catalytic IgVs. Unexpectedly, IgVs with rare IgVL2-t and IgVL-t' structures expressed the greatest catalytic activity directed to Aβ. The invention also discloses single chain Fv constructs (scFvs) obtained by repairing the aberrant VH domain contained in the IgVL-t' construct. Such repaired scFvs displayed reduced catalytic activity, indicating that the VH domain generally suppresses VL domain catalytic activity.

The use of electrophilic antigen analogs in the present invention is based on the principle that nucleophilic sites located in the V domains imparts to some Igs the ability to catalyze chemical reactions. The nucleophilicity derives from activation of certain amino acid side chains. In serine proteases, precise spatial positioning of the Ser-His-Asp triad allows formation of a hydrogen bonded network that imparts nucleophilic reactivity to the Ser oxygen. Similar sites are present in catalytic V domains [55]. Previous studies have shown that V domain nucleophilic sites bind covalently to phosphonate esters incorporated within antigenic epitopes [56,57].

The electrophilic antigen analogs are designed based on the split site model of catalytic Igs, in which the Ig paratope and nucleophilic sites are treated as two distinct subsites. The analogs are derivatives of polypeptides in which one or more amino acid side chains are linked to the electrophilic phosphonate group as described in US Patent application 20070105092. Examples of other suitable electrophiles are the carbon atom in carbonyl esters, carbonyl amides, carbonates, aldehydes, ketones and aliphatic and aromatic carbonyl compounds; the boron atom in boronates and the vanadium atom in vanadates. Electron withdrawing and donating groups are linked directly to the electrophilic atom or via spacer groups to enhance and decrease the covalent reactivity with IgV nucleophiles. Optionally, a positive charge or a negative charge is placed in the vicinity of the electrophilic atom to mimic the basic residue and acidic residue specificity of catalytic Igs.

The catalytic sites of the IgVs disclosed in the present invention can be produced as a result of innate as well as adaptive immune processes. Previous studies have indicated that Ig nucleophilic and proteolytic activities are heritable traits, encoded by germline V domains [58]. Because the catalytic activity is germline-encoded, in principle, the immune system is capable of mounting catalytic Ig V domains directed to any polypeptide antigen. Adaptive specialization for recognition and cleavage of the polypeptide antigen can occur by processes such as V-D-J/V-J junctional diversification and somatic hypermutation of the V domains.

In another embodiment, the invention discloses improved catalytic mutants of an IgVL2-t obtained by random mutagenesis of the VL domains, display of the mutant proteins on phage surface and isolated mutant $IgV_{L2}$-t clones by covalent phage selection using the electrophilic Aβ analog.

Additional embodiments of the inventions disclose IgVs directed to proteins belonging to infectious microbes. One such embodiment is isolation of catalytic IgVs to *S. aureus* virulence factors, for example, the virulence factor Efb, obtained by random screening of the lupus IgV library described above. A catalytic scFv and an IgVL2-t that hydrolyzed Efb was identified by the by electrophoresis screening methods. Catalytic IgVs with improved catalytic activity can readily be obtained by conducting phage selection procedures as described, for example, using electrophilic analogs of Efb.

The invention also discloses the composition of catalytic IgVs directed to the HIV coat protein gp120. These IgVs can be obtained from human IgV libraries as described above. Selection of the IgVs displayed on phage surface can be accomplished using gp120, an electrophilic analog of gp120 or peptides corresponding to the antigenic epitope recognized by the IgVs. HIV gp120 is a B cell superantigen recognized by IgVs from humans without infection. The invention discloses IgVs that recognize the superantigenic peptide epitope composed of gp120 amino acid residues 421-433, SEQ ID NO: 40, or 416-433 and neutralize HIV infection of lymphocytes. Certain IgVs that catalyze the hydrolysis of gp120 are described. As the IgVs neutralize diverse HIV strains they can be applied for immunotherapy of HIV infection. In addition, they can be used as topical microbicides for prevention of heterosexual HIV transmission.

Another embodiment of the invention concerns recognition of B cell superantigens by the V domains, which is thought to occur mainly at conserved V domain residues. IgVs obtained by mutagenesis methods with improved recognition of the HIV gp120 superantigenic site are disclosed. The approach for obtaining the mutants consists of replacing entire FRs or CDRs of the VH domains by corresponding FRs or CDRs drawn from other V domains. In addition, the ability of the VL domain to recognize the HIV gp120 superantigenic site is disclosed. Improved superantigen recognition can also be readily attained by pairing of two V domains that can independently recognize the superantigenic site. Similarly, mutations introduced at individual amino acids in the FRs or CDRs can be employed to improve IgV recognition of the superantigens. Also disclosed are the novel B cell superantigenic properties of the *S. aureus* virulence factors, Map19, ClfA, LukF and SdrE. The disclosed IgV engineering methods can readily be applied to obtain improved recognition of the *S. aureus* virulence factors.

The IgVs can be engineered further to improve their stability in vascular circulation and other anatomic sites, for example by linkage to a polyethylene glycol molecule or the Fc region of Igs. Also disclosed are novel full-length catalytic IgGL and IgML molecules containing antigen combining sites composed of 2 VL domains instead of one VL domain and one VH domain. Also disclosed are two novel bivalent Fc-containing derivatives of an $IgV_{L2}$-t: (a) an IgGL construct in which one of the $V_L$ domain was cloned into the light chain subunit (κ) and the second $V_L$ domain into the heavy chain subunit (in place of the $V_H$ domain); and (b) an Fcγ-$(IgV_{L2})_2$ construct containing two $IgV_{L2}$ components attached to the N terminii of the Fc fragment. The novel IgGL and Fcγ-$(IgV_{L2})_2$ expressed catalytic activity, indicating that the integrity of catalytic site is unaffected by inclusion of the Fc fragment. Such engineering strategies can be used to prepare long-lived Ig catalysts as immunotherapeutic agents.

The invention discloses that variations in the structure of the terminal t' region that do not influence of the single domain IgVL-t' function. The t' region interferes with non-covalent V domain association and maintains the IgVL-t' in monomeric form with high level catalytic activity. Optionally, the t' region can contain peptide or non-peptide structures that direct the IgV to the desired target anatomic site. For example, inclusion of the polyanionic compound putrescine or the TAT peptide in the t' region can facilitate passage of the IgV across the blood-brain-barrier. Similarly, the t' region can include an scFv directed to an antigen expressed at the blood-brain-barrier to facilitate transport across the blood-rain-barrier, for example an scFv to the insulin receptor known in the art to transport drugs across the barrier.

Another aspect of the present invention consists of identifying polyclonal Igs from blood and mucosal secretions with enriched catalytic activity. This can be accomplished by screening Ig preparations from individual human donors and identifying those immunoglobulin preparations that express catalytic activity greater than the average catalytic activity of Ig preparations. Optionally, the Igs can be obtained from human blood. Alternatively, the present invention also discloses IgG, IgA and IgM preparations obtained from mucosal fluids such as saliva. The catalytic activity is directed to one or more protein, e.g., an *S. aureus* virulence factor, the HCV coat protein E2, the HIV coat protein gp120 or Aβ. For example, the invention discloses findings of exceptionally potent HIV neutralization by IgA preparations from long-term survivors of HIV infection. Such Ig preparations are a suitable source of pooled Igs for treatment and prevention of HIV infection. Similarly, screening of human donors has revealed variable levels of catalytic Igs directed to *S aureus* virulence factors protein A, Map19, ClfA, LukF and SdrE. Screening of human donors with HCV infection has revealed enhanced levels of catalytic IgMs to the HCV coat protein E2, with activity levels varying widely from one donor to another. Screening of human donors has revealed similar variations in catalytic IgMs directed to Aβ. The present invention conceives pooled Igs from donors expressing enriched levels of catalytic activities to the appropriate antigens to be useful in various medical treatments, including treatment of antibiotic-resistant *S. aureus* infection, HCV infection and Alzheimer disease.

To one skilled in the art, it is evident that protective monoclonal Abs can readily be cloned from the catalytic Ig producing subjects by procedures such as lymphocyte immortalization by Epstein-Barr virus or antibody repertoire cloning and phage display by molecular biology methods. Similarly, the present invention conceives preparation of IgVs from the catalytic Ig producing subjects.

The monoclonal and recombinant Igs disclosed in the present invention can be readily improved by various protein engineering methods familiar to persons skilled in the art. Examples of the engineering techniques are as follows.

The IgVs can be recloned as full-length IgG, IgM and IgA to provide for increased half-life in vivo and increased avidity of protein recognition. When administered to animals, Fv constructs display half-lives in blood on the order of hours. In comparison, the half-life of full-length Abs in blood can be as large as 2-3 weeks. Therefore, to achieve persistent neutralization of the antigen, the preferred reagents are the full-length Igs. On the other hand, the smaller IgV constructs may offer tissue penetration capabilities superior to full-length Igs.

Recloning monovalent IgVs as IgG, IgM and IgA provides for increased antigen binding valencies, respectively. This is useful in some instances. Multivalent binding improves the apparent antigen binding strength, known in the art by the term avidity. In addition, the constant domains imparts important effector functions to Igs, for example, the ability to fix complement, mediate Ig-dependent cellular cytotoxicity and bind Fc receptors. Full-length Igs are readily obtained from IgVs by cloning the V domains into appropriate mammalian cell expression vectors. The vectors contain cDNA encoding the constant domains of the desired Ig class and subclass. The vectors are available commercially, for example, from Lonza. The vectors contain human Ig constant domains flanked by restriction sites for insertion of foreign V domains.

Increased avidity of antigen recognition can also be obtained by forming IgV multimers. For example, tetravalent antibody fragments are generated by placing a 33-amino acid self-aggregating peptide derived from the GNC4 protein at the C terminus of an scFv construct. The peptide associates noncovalently into a 4-helix bundle, permitting expression of multiple valencies.

The sequences of VL, VH and linker domains can be varied by mutagenesis to improve their biological activity. The mutants expressed on the surface of a display vector as described above are allowed to bind the target antigen. This allows separation of the mutants with the highest antigen recognition capability, which in turn can be anticipated to result in improved neutralization capacity. Mutagenesis of the linker peptide that joins the VL and VH domains is designed to improve the interfacial contacts of the VL and VH domains, which allows these domains to form superior antigen binding cavities. To obtain IgVs with improved catalytic activity, mutations are introduced into the FRs or CDRs using mutagenic primers, the mutant molecules are expressed on the surface of phages, and the phages are allowed to bind covalently to the electrophilic antigen analogs. The process is repeated several times, with additional mutations introduced at each cycle followed by the phage separation by antigen binding.

In addition to the strategy described above, favorable mutations can also be introduced in the V domains on a rational basis to improve the catalytic activity. For instance, candidate amino acids suitable for mutagenesis can be identified by molecular modeling or X-ray crystallography information. The ligand can be positioned in the hypothetical binding site to identify candidate residues suitable for rational mutagenesis. For instance, replacement of a small neutral amino acid with a similarly sized charged residue can be attempted as a means to introduce an additional electrostatic stabilizing interaction.

The catalytic VL domain can be paired with the VH domain of other Igs with specific target antigen binding activity. This can improve the binding strength to the target antigen and also result in changes in epitope specificity that can improve antigen neutralizing activity.

The catalytic Igs described herein are generally administered to a patient as a pharmaceutical preparation. The pharmaceutical preparations of the invention are conveniently formulated for administration with a acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the Abs in the chosen medium will depend on the hydrophobic or hydrophilic nature of the medium, as well as the other properties of the catalytic antibodies. Solubility limits may be easily determined by one skilled in the art.

In one preferred embodiment, the catalytic Igs can be infused intravenously into the patient. For treatment of certain medical disorders, steps must be taken to ensure that sufficient amounts of the molecules reach their target cells to exert a biological effect. The lipophilicity of the molecules, or the pharmaceutical preparation in which they are delivered may have to be increased so that the molecules can arrive at their target locations. Furthermore, the Igs of the invention may have to be delivered in a cell-targeted carrier so that sufficient numbers of molecules will reach the target cells. Methods for increasing the lipophilicity and targeting of therapeutic molecules, which include capsulation of the Igs of the invention into liposomes, are known in the art.

The IgVs and Igs or pharmaceutical compositions thereof of the present invention can also be used as topical microbicides, for example as a vaginal cream, foam or film. Alternatively, the IgVs and Igs or pharmaceutical compositions thereof may be administered intranasally, topically, interperitoneally, intrarectally, or intracerebrally as is known in the art.

The pharmaceutical IgV or Ig preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. For example, the half-life of syngeneic IgG in the human is about 20 days. Over this period, 60,480 antigen molecules will be cleaved by one molecule of an antibody with a turnover of 2.1/min. It can be seen, therefore, that the peptidase antibodies can express considerably more potent antigen neutralizing activity than stoichiometric, reversibly-binding molecules. As is well-known and standard in the art the pharmaceutical preparation or composition may comprise standard adjuvants and/or diluents as are known in the art.

The pharmaceutical preparation comprising the catalytic Igs may be administered at appropriate intervals, for example, twice a week until the pathological symptoms are reduced or alleviated, after which the dosage may be reduced to a maintenance level. The appropriate interval in a particular case would normally depend on the condition and the pathogenic state sought to be treated in the patient.

Standard criteria for acceptable prophylactic or therapeutic agents are employed as follows: (1) Discussions of how such criteria are established for the acceptability of prophylactic or therapeutic agents are common in the art can can be found in such texts as *Guide to Clinical Trials* by Bert Spilker, Raven Press, New York, 1991. Acceptable criteria for demonstration of efficacy include, for example, measuring clearance of bacterial infection. Conventional monoclonal Igs that act to inhibit the function of particular target molecules are among the most common type of therapeutic agent under development for clinical use by biotechnology and pharmaceutical companies. Accordingly, methods of administration of monoclonal Igs are well known to clinicians of ordinary skill in the art. The Igs contemplated in the present invention will constitute a major improvement over such conventional monoclonal Igs because of their superior potency, resulting in dramatic decrease in the cost of treatment.

While certain of the preferred embodiments of the present invention have been described and specifically exemplified above, it is not intended that the invention be limited to such embodiments. Various modifications may be made thereto without departing from the scope and spirit of the present invention. The following examples are provided to facilitate an understanding of the present invention.

The following examples are given for the purpose of illustrating various embodiments of the invention and are not meant to limit the present invention in any fashion.

Example 1

Catalytic Igs to Amyloid Peptide
Aβ Hydrolyzing Polyclonal IgMs

Accumulation of amyloid β peptide (Aβ) aggregates in the brain is thought to be a central event leading to neurodegenerative changes observed in Alzheimer disease (AD). There is consensus that immunoglobulins (Igs) with specific Aβ binding activity are viable candidates for AD therapy. Monoclonal and polyclonal candidate Igs are under consideration for this purpose. The polyclonal Igs consist of pooled IgG class antibodies from normal humans that contain a small amount of Aβ binding IgGs (commonly referred to as intravenously infused IgG, IVIG [59]. The monoclonal Igs were raised by immunization of mice with Aβ and 'humanized' by protein engineering to reduce undesirable human anti-mouse Ig responses. Studies using murine AD models have indicated that peripherally administered monoclonal Igs and polyclonal IVIG with Aβ binding activity can clear Aβ from the brain [60-62]. Phase III trials of a monoclonal Aβ binding IgG for AD therapyare ongoing (Wyeth-Elan). Baxter has announced its intent to start a Phase III IVIG trial.

It was observed that electrophoretically homogeneous IgMs from the sera of elderly healthy subjects without dementia (>65 years) hydrolyzed Aβ at levels greater than non-elderly adults (<35 years; P=0.035; Student's t-test for unpaired observations [63]. To evaluate disease association, the hydrolysis of $^{125}$I-Aβ40 by IgM preparations from 25 non-demented elderly individuals and 23 AD patients were compared. Excess albumin was present as an alternate substrate in the assays, minimizing the contribution of promiscuous antigen recognition. Intact Aβ was separated from product peptides by 5% trichloroacetic acid (TCA) precipitation. Alternatively, reversed-phase high performance liquid chromatography was employed to separate intact and fragmented Aβ using a Novapak C18 column with 0.05% trifluoroacetic acid in acetonitrile for elution. Observed values of hydrolysis measured by the TCA precipitation method and RP-HPLC were highly correlated ($r^2$ 0.96). Twenty two of the 25 IgM preparations from undemented elderly humans studied displayed detectable $^{125}$I-Aβ40 hydrolytic activity varying over a 118-fold range. This suggests that the catalytic IgM response is polymorphic and varies in different individuals. IgMs from the AD group displayed superior hydrolytic activity (P<0.0001; two-tailed Mann-Whitney U test and Student's t-test; FIG. 1). HPLC and ESI-MS studies indicated using pooled IgM indicated hydrolysis mainly at the Lys28-Gly29 bond, and at lesser levels, at the Lys16-Leu17 bond. The IgMs from AD patients did not hydrolyze irrelevant polypeptides determined by an electrophoresis assay (biotinylated soluble epidermal growth factor receptor, albumin or ovalbumin [63]. It may be concluded that increased Aβ40 hydrolysis by IgM preparations from AD patients is not due to an increase of non-specific catalytic activity.

To exclude the possibility of trace protease contaminants, pooled polyclonal IgM previously purified by affinity chromatography using anti-IgM antibody was subjected to 2 cycles of sequential gel filtration in a solvent that dissociates noncovalently associated protein-protein complexes (6 mol/L guanidine hydrochloride). The highly purified 900 kDa IgM fraction from the second chromatography cycle displayed detectable Aβ40 hydrolytic activity determined by RP-HPLC (68 pmol/h/mg IgM), and the product profile was essentially identical to the starting IgM preparation. To our knowledge, there are no known conventional proteases with mass 900 kDa. The denaturing column conditions preclude the possibility of smaller adventitious proteases.

Aβ40 Hydrolyzing IgVs

A human library composed of ~$10^7$ clones was searched for Aβ40 hydrolyzing recombinant IgVs. The library was constructed as described in (64). A majority of the clones in the library are scFv-t constructs with the domain organization $V_L$-Li-$V_H$-t, where Li denotes the 16-residue peptide SS(GGGGS)$_2$GGSA (SEQ ID NO: 57) joining the $V_L$ domain C terminus to the $V_H$ domain N terminus and t denotes the 26 residues C terminal peptide containing the c-myc peptide and his$_6$ tags [64]. The library also contains a minority of IgV clones with unnatural structures generated by cloning errors (see below). Sixty three IgVs purified from the periplasmic extracts of randomly picked clones by his6 tag binding to Ni-affinity columns were tested for $^{125}$I-Aβ40 hydrolyzing recombinant IgVs 40 hydrolyzing activity. Concentrations of the IgV in these extracts are variable and depend on the expression level from bacteria. Generally, the concentration vary from 1-10 μg/ml in the hydrolysis assay. Two IgVs displayed with activity distinctly greater than the remaining clones were identified (FIG. 2A). The activity of the empty vector control extract (pHEN2 devoid of an IgV insert) was within the range of assay errors (mean of background TCA soluble radioactivity+3 S.D. values, 32.4 fmol/h/mg/IgV). The phagemid DNA of the high activity IgV clone 2E6 was re-expressed in 15 individual bacterial colonies. All recloned colonies secreted IgV with robust $^{125}$I-Aβ40 hydrolyzing recombinant IgVs 40 hydrolyzing activity (FIG. 2B), ruling out trivial sample preparation differences as the cause of proteolytic activity. As before, purified extract of the control empty vector clone did not hydrolyze $^{125}$I-Aβ40 hydrolyzing recombinant IgVs 40.

Figure 3A:
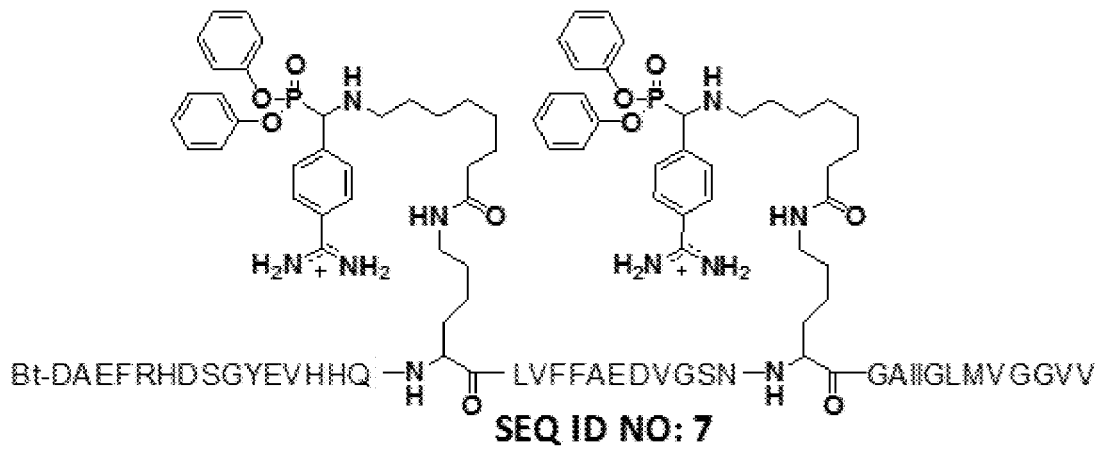
FIGS. 3A-3C are a selection of Aβ hydrolyzing IgVs with E-Aβ40.

Previous studies have suggested catalytic Ig nucleophilic sites recognize polypeptide antigens containing electrophilic phosphonates by noncovalent peptide epitope binding coordinated with covalent bonding to the phosphonate group [57]. To isolate Aβ40 hydrolyzing recombinant IgVs 40 selective nucleophilic IgVs, a biotinylated Aβ40 hydrolyzing recombinant IgVs 40 analog (Bt-E-Aβ40; FIG. 3A) containing phosphonates located at the side chains of Lys16 and Lys25 residues was prepared. Bt-Aβ40 hydrolyzing recombinant IgVs 40 (6 mg) was reacted with diphenyl-N—[O-(3-sulfosuccinimidyl)suberoyl]-amino(4amidinophenyl) methane phosphonate in DMSO. The reaction mixture was purified by reversed-phase HPLC, and lyophilization. Its identity and purity were confirmed by HPLC [retention time 36.36 min, >99.9%; 0.05% TFA in water:0.05% TFA in acetonitrile:10-40:60 in 50 min, 1.0 ml/min; 220 nm absorbance], electrospray ionization mass spectrometry [observed m/z, 1427.6, 1142.6 and 952.4; calculated $(M+4H)^{4+}$, $(M+5H)^{5+}$ and $(M+6H)^{6+}$ for $C_{266}H_{380}N_{62}O_{71}P_2S_2$; 1427.1, 1141.9 and 951.8, respectively].

Phages displaying the IgVs as p3-fusion proteins were packaged from TG1 E. coli cells harboring the recombinant vector using helper phages, and the phages were subjected to a covalent selection procedure. Briefly, the phages were incubated (1 ml; 10 min, 25° C.) with Bt-E-A Aβ40 hydrolyzing recombinant IgVs 40 immobilized on anti-biotin gel (Sigma) in 10 mM sodium phosphate, 0.137 mM NaCl, 2.7 mM KCl, pH 7.4, (PBS) containing 1% skimmed milk. The phage-gel mixture was packed in a column and washed with PBS until A280 was <0.01. Noncovalently bound phages were removed by successive washes with A Aβ40 hydrolyzing recombinant IgVs 1-40 solution (5 column volumes) and covalently bound phages were eluted with 0.1M glycine-HCl, pH 2.7. Soluble IgVs were obtained by infecting HB2151 cells with the phages. Periplasmic extracts were prepared following induction with isopropyl-d-thiogalactoside. For initial screening of catalytic activity, the IgVs were purified by a single round of metal affinity chromatography by means of the His6 tag at the C terminus. For further characterization, the extract was subjected to two sequential rounds of metal affinity chromatography. SDS-gel electrophoresis was on 4-20% gels. Total protein was determined by the microBCA kit (Pierce). To separate monomer from aggregates and eliminate degradation products, an FPLC anion exchange column (MonoQ HR 5/5, GE healthcare) equilibrated with 50 mM Tris buffer, pH 7.4, containing 0.1 mM CHAPS was employed. Ni-purified IgVs (10 ml) were dialyzed against equilibration buffer and subjected to chromatography. Bound protein was eluted with a linear gradient of NaCl from 0 to IM. Fractions (500 µl each) were analyzed by SDS-PAGE as described above.

Figure 3B:
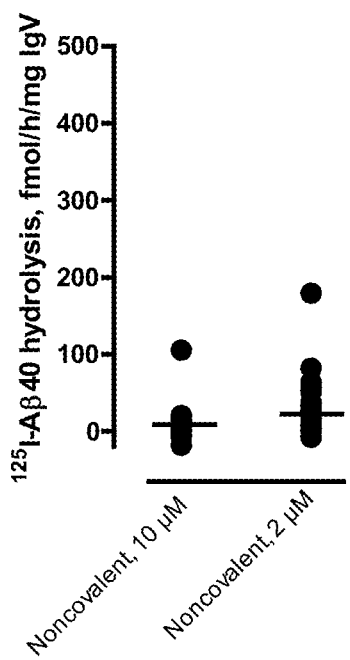
Figure 3C:
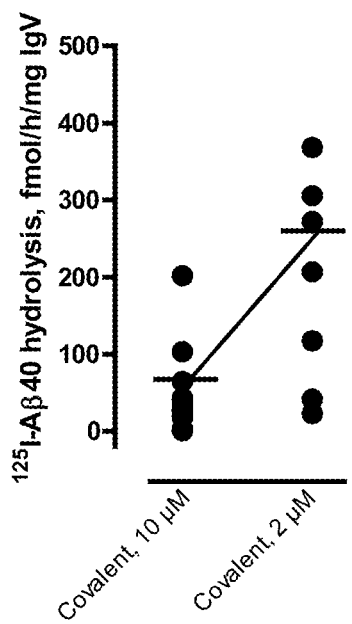

Phage IgVs obtained by treatment with excess A Aβ40 hydrolyzing recombinant IgVs 40 were designated noncovalently selected IgVs. Residual irreversible phage IgV immune complexes eluted by acid disruption of the biotin-anti-biotin antibody complexes were designated covalently selected IgVs. The noncovalently selected IgVs displayed no or minimal $^{125}$I-Aβ40 hydrolyzing recombinant IgVs 40 hydrolyzing activity (FIG. 3B). Several covalently selected IgVs expressed robust hydrolytic activity that increased increased as a function of decreasing E-Aβ40 concentrations employed for phage selection (FIG. 3C). This is consistent with the prediction of more efficient proteolysis by IgVs with the greatest Aβ40-directed nucleophilic and noncovalent binding reactivities.

IgV Primary Structure and Activity Validation

Figure 4A:
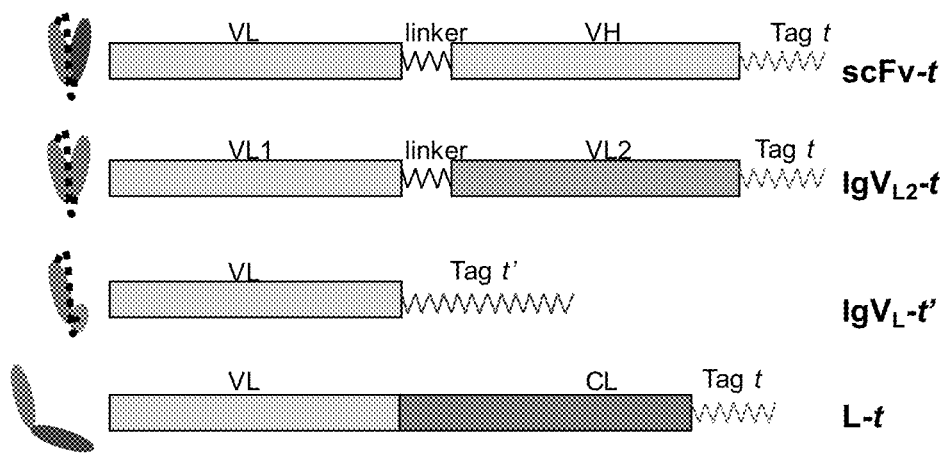
FIGS. 4A-4B show schematic representations (FIG. 4A) and purity of Aβ-hydrolyzing IgVs (FIG. 4B). scFv-t, VL domain and VH domains connected by a peptide linker; t, His6/c-myc tag located at the C-terminus; IgV$_{L2}$-t, heterodimeric construct composed of two different VL domains; IgV$_L$-t', the single domain IgV containing a VL domain. t' corresponds to the linker, an aberrant polypeptide in place of the VH domain at the C terminus of the linker and the His6-c-myc tag; L-t, full-length light chain containing the VL domain, the light chain constant domain (κ) and the terminal tag t.

IgV clone 2E6 obtained without phage selection and 3 covalently selected IgVs with the greatest Aβ40-hydrolyzing activity (clones 5D3, 1E4 and 5H3) were studied further. Identical cDNA sequences were obtained for each clone by sequencing from the 5' to 3' direction and the 3' to 5' direction. IgV 2E6 is a single chain heterodimer of two different $V_L$ domains (designated heterodimeric $IgV_{L2}$-t, FIG. 4A; full sequences shown in FIG. 5). IgVs 5D3, 1E4 and 5H3 are single domain $V_L$ clones with unexpected C terminal polypeptide segments, designated $IgV_L$-t' clones, where t' denotes (a) the expected linker peptide, (b) an unexpected 15-28 residue aberrant peptide sequence in place of the customary $V_H$ domain composed of ~115 residues, and (c) the expected 26 residue peptide sequence containing c-myc and his6 tags (FIG. 4A and FIG. 5).

Figure 4B:
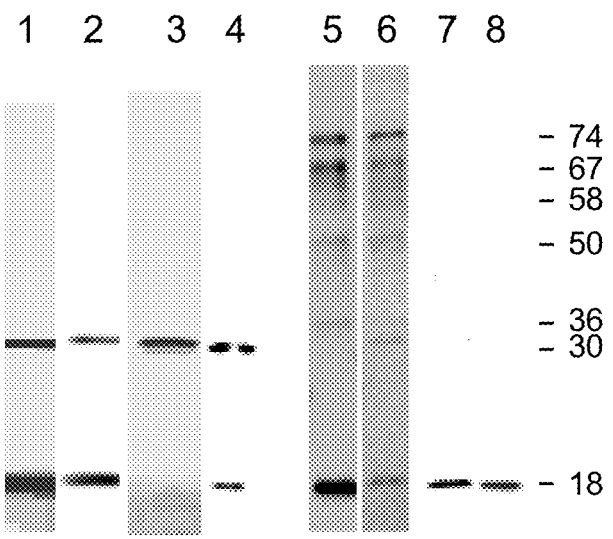

Two clones were studied further, $IgV_{L2}$-t 2E6 and $IgV_L$-t' 5D3. Their deduced protein masses predicted from the cDNA sequences, are respectively, 27 and 17 kD. Denaturing electrophoresis and silver staining of the proteins purified by 2 cycles of $his_6$ binding to Ni columns revealed proteins close to the predicted mass of the monomer IgVs ($IgV_{L2}$-t 2E6, 30 kD; $IgV_L$-t' 5D3, 18 kD; FIG. 4B). However, additional protein bands were visible (low mass $IgV_{L2}$-t 2E6 band at 18 kD; high mass $IgV_L$-t' 5D3 bands at 36, 50, 58, 67 and 74 kD). All of the additional bands were stained with anti-c-myc antibody (FIG. 4B). As irrelevant proteins are not stained nonspecifically by the anti-c-myc antibody (phosphorylase b, BSA, ovalbumin, carbonic anhydrase, trypsin inhibitor, α-lactalbumin), there is no evidence of non-IgV contaminants. It was concluded that the anomalous low mass $IgV_{L2}$-t band is a self-degradation product and the high mass $IgV_L$-t' band are aggregates. The $IgV_{L2}$-t and $IgV_L$-t' were purified by anion exchange FPLC to electrophoretically homogeneous proteins that migrated as monomers in the denaturing electrophoresis gels (FIG. 4B). The identity of the 5D3 monomer band was confirmed by peptide tryptic digestion and mass spectroscopic analysis. The IgV $^{125}$I-Aβ40 hydrolyzing activities were essentially identical after one and two cycles of chromatography on Ni columns, and they were increased noticeably following FPLC purification (Table 2; by 3.1-fold and 31.2-fold, respectively, for the $IgV_{L2}$-t and $IgV_L$-t'). These observations indicate that the Aβ hydrolyzing activity is attributable to the IgVs.

TABLE 2

$^{125}$I-Aβ1-40 hydrolyzing activity of different IgV preparations. The recombinant IgV preparations purified by one round of metal-affinity chromatography on Ni agarose (preparation "MA1") were subjected to either another round of Ni chromatography ("MA2") or anion exchange chromatography on MonoQ ("AEQ"). Hydrolysis assay conditions are as in FIGS. 3A-3C. Shown are specific activities expressed in fmol/h/mg protein unit (mean ± SD).

| | Specific activity, fmol/h/mg protein IgV (mean ± SD) | | |
|---|---|---|---|
| Ig | MA1 | MA2 | AEQ |
| $IgV_{L2}$-t 2E6 | 380 ± 73 | 368 ± 40 | 1158 ± 285 |
| $IgV_L$-t' 5D3 | 543 ± 270 | 552 ± 127 | 17239 ± 1481 |

Sequencing of 26 randomly picked clones from the library indicated that the majority of the IgVs in the library are scFv constructs (83.3%) and a minority are $IgV_{L2}$-t constructs (12.5%) or $IgV_L$-t' (4.2%) structures. The cumulative probability of identifying 4 high activity Aβ40-hydrolyzing clones from the library with the rarely represented $IgV_{L2}$-t or $IgV_L$-t' structures by random chance alone is very small (P=0.92×10$^{-5}$; computed as 0.125×0.042$^3$). As none of the high activity clones contain the archetypal $V_L$-$V_H$ paired structure of physiological Ab combining sites, it may be concluded that expression of Aβ hydrolyzing activity by the rare $V_L$ domain IgV structures is a favored event It was reported recently that the Aβ40 hydrolyzing activity of polyclonal human IgM preparations, a monoclonal IgM from a patient with Waldenstrom's macroglobulinemia

Figure 6A:
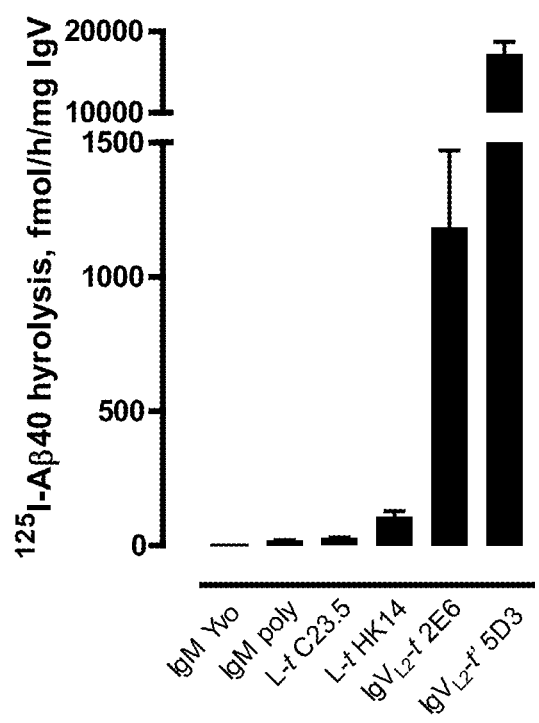
FIGS. 6A-6B illustrate catalytic activity of IgVs and mutant IgVs.

[63], and the cross-reactive light chain subunit of an Ig directed to the antigen VIP [8]. IgV$_{L2}$-t 2E6 and IgV$_{L}$-t' 5 D3 hydrolyzed $^{125}$I-Aβ40 with potency superior to the previously identified IgM and light chain preparations by 1-4 orders of magnitude (FIG. 6A).

Figure 6B:
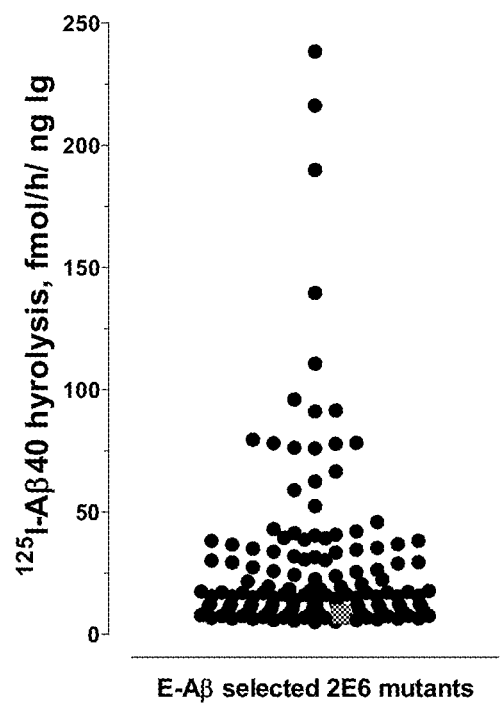

To further improve the catalytic activity, a phage library of randomly mutated IgV$_{L2}$-t 2E6 clones (~4 mutations/molecule; 7×10$^6$ clones) was prepared and isolated mutant IgV$_{L2}$-t clones were isolated by covalent phage selection. The library was produced by a standard error-prone PCR method known to a person skilled in the art using a commercially available kit (Mutazyme II, Stratagene; template clone 2E6 in pHEN2; concentration adjusted to yield the desired number of mutations; verified by sequencing of 15 clones). Mutant IgV$_{L2}$-t phages were selected by covalent binding to E-Bt-Aβ40 (0.1 nM) as described above. Soluble IgV$_{L2}$-t mutants secreted into culture supernatants were screened for Aβ hydrolytic activity along with empty vector controls and wildtype supernatants. Several mutants with substantially improved Aβ hydrolyzing activity have been isolated (FIG. 6B). The mutant with greatest activity, designated clone 2E6m, has been selected for further development in the present proposal.

Repaired IgV 5D3

The aberrant t' region of IgV$_L$-t' 5D3 contains 7 residue V$_H$ FR1 and 8 residue CH1 peptides with deletion of V$_H$ residues 8-115 (Kabat numbering; FIG. 7). Repaired scFv-t molecules were generated by replacing the t' region of IgV$_L$-t' 5D3 by four randomly picked full-length V$_H$ domains (sequences are available in FIG. 7). The deleted V$_H$ segment was filled in by PCR amplification of V$_H$ domains from the IgV library. For VH amplification, back and forward primers were designed to anneal the partial FR1 and CH1 sequences. To facilitate cloning, ApaLI and NotI sites were incorporated into the back (GGTAGTGCACTTCAGGTGCAGCTGTTGCAGTCT; SEQ ID NO: 1)
and forward
(ATGTGCGGCCGCGGGGAAAAGGGTTGGGGGCATGC; SEQ ID NO: 2)
primers, respectively. Plasmid DNA encoding the IgV library was used as the template. PCR was performed using Taq DNA polymerase (Invitrogen) as follows: an initial denaturation step for 5 min at 95° C., followed by 35 cycles each of amplification (1 min at 95° C., 1 min at 40° C. and 1 min at 72° C.) and a final extension step of 10 min at 72° C. The PCR product was digested with ApaLI and NotI and ligated into the IgV vector similarly digested using T4 DNA ligase (Invitrogen) according to manufacturer's protocols. Electrocompetent HB2151 *E. coli* were transformed with the ligation mixture and transformants were selected on 2YT ampicillin plates. To prepare the full-length L chain counterpart of clone 5D3, the V$_L$ domain was amplified by PCR with primers containing NcoI and NotI restriction sites and cloned into similarly digested pHEN2. The construct also contained the constant κ domain with the His6-c-myc tag at the C terminus. The sequences of the constructs were verified and soluble scFv antibodies were expressed in HB2151 *E. coli* as mentioned above. Purification of secreted scFv-t and L-t on Ni columns afforded electrophoretically homogeneous scFv-t proteins at the expected mass (30 kD, example shown in FIG. 8B).

Figure 8A:
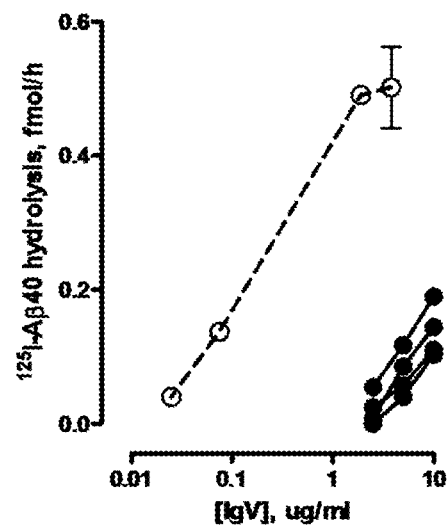
FIGS. 8A-8C illustrates the $^{125}$I-Aβ40 hydrolyzing activity of various derivatives of IgV$_L$-t' 5D3, i.e., the repaired scFv-t, full-length L-t and homodimeric IgV$_{L2}$-t.
Figure 8D:
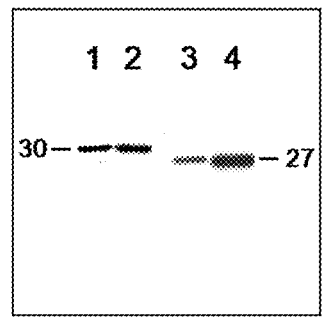
FIG. 8D shows SDS-PAGE gels showing purified L-t (lane 1) and IgV$_{L2}$-t (lane 3) stained with silver. Lane 2 and 4 show, respectively, the L-t and IgV$_{L2}$-t stained with anti c-myc antibody. The bands at 30 kDa and 27 kDa represent, respectively, the L-t and IgV$_{L2}$-t.
Figure 8B:
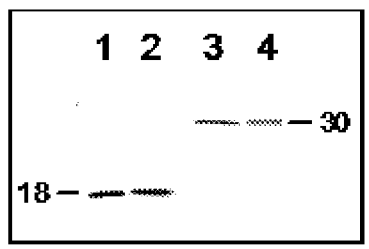
Figure 8C:
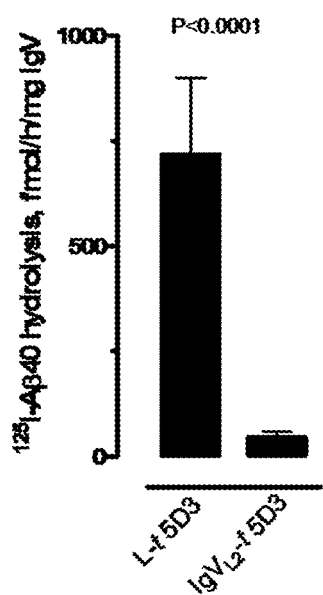

The $^{125}$I-Aβ40-hydrolyzing activity of the scFv-t constructs was consistently lower than the parent IgV$_L$-t' (by ~82-167 fold; FIG. 8A), suggesting an autonomous catalytic site located in the V$_L$ domain that is suppressed by pairing with the V$_H$ domains. The V$_L$ domains of Igs tend to form noncovalent aggregates [66,67], introducing uncertainty as to whether the catalytic species is a monomer or an aggregate. Thus, the homodimeric IgV$_{L2}$-t molecule containing the two 5D3 V$_L$ domains connected by the peptide linker was prepared. Purified IgV$_{L2}$-t 5D3 hydrolyzed $^{125}$I-Aβ40 poorly (FIG. 8B). On the other hand, the V$_L$ domain linked to the κ constant domain displayed readily detected hydrolytic activity (this molecule corresponds to the light chain subunit, designated L-t). In denaturing electrophoresis gels, the homodimeric IgV$_{L2}$-t 5D3 migrated at the predicted 27 kD position with no evidence of degradation into monomers (FIG. 8D). L-t, on the other hand, migrated as a mixture of 30 kD monomers and 60 kD S—S bonded dimers. These observations suggest that the monomeric, unpaired V$_L$ domain state favors maintenance of catalytic site integrity.

IgV$_{L2}$-t 2E6 was recloned as an IgGL using immunoglobulin expression vector cassettes containing human γ1 constant and λ constant domains described in (McLean et al.; Molec. Immunol. 37, 837-845, 2000). The two VL domains were PCR amplified using primers containing appropriate restriction sites

```
                                          SEQ ID NO: 3
     (taagatctCAGTCTGCCCTGACTCAGCCT,;

SEQ ID NO: 4
     tagcggccgcgggctgacc TAAAACGGTGAG,;

SEQ ID NO: 5
     taGAATTCCAGTTGACCCAGTCTCC,
     and

SEQ ID NO: 6
     taaagcttgcACGTT TGATTTCCAGCT T,;
``` contain NcoI/XhoI sites and BglII/NotI sites, respectively;

```
                                          SEQ ID NO: 5
     taGAATTCCAGTTGACCCAGTCTCC,
     and SEQ ID NO: 6
     taaagcttgcACGTT TGATTTCCAGCT T;
``` contain ApaLI/NotI sites and EcoRI/HindIII), followed by cloning into similarly digested pHC-huCγ1 and pLC-huCλ vectors. Essentially similar methods were used to prepare the Fcγ-(IgV$_{L2}$)$_2$ 2E6 construct containing two IgV$_{L2}$ components attached to the N terminus of the γ1 Fc fragment using the pHC-huCγ1 vector in which the CH1 domain of the heavy chain subunit had been removed. After sequence verification, the recombinant proteins were expressed in HEK293 cells by transient transfection using Lipofectamine (Invitrogen) using standard protocols. The proteins were purified by protein G affinity chromatography as described previously.

Figure 8E:
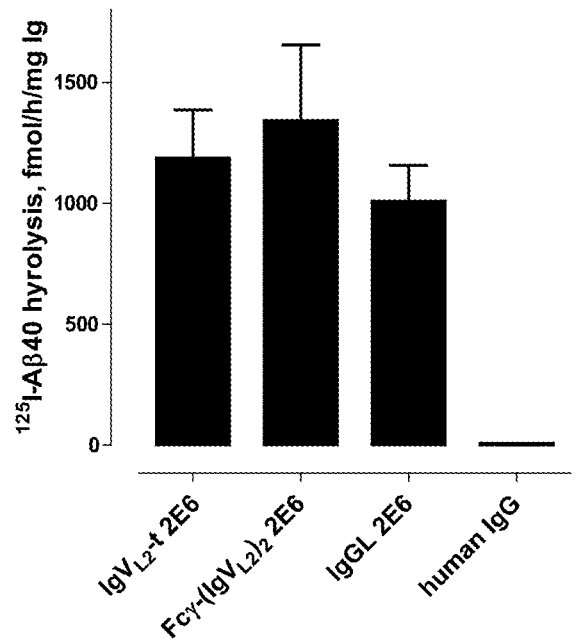
FIG. 8E shows Aβ hydrolysis by IgGL and Fcγ1-(V$_{L2}$)$_2$ versions of clone 2E6. IgGL and Fcγ1-(IgV$_{L2}$)$_2$ purified by Protein G-Sepharose chromatography from culture supernatants of NS0 cells transfected with the appropriate heavy and light chain expressing vectors. Identically purified control IgG from human serum was without activity. No extraneous polypeptide tags are present in the IgGL or Fcγ1-(V$_{L2}$)$_2$.

The three versions of the 2E6 clone [IgGL, Fcγ-(IgV$_{L2}$)$_2$ and IgV$_{L2}$-t] hydrolyzed Aβ with comparable potency (FIG. 8E). Identically purified irrelevant IgGs did not hydrolyze Aβ. These observations indicate that the integrity of catalytic site is not compromised by inclusion of the Fc fragment and that it is possible to prepare long-lived versions of the Ig catalysts as candidate immunotherapeutic agents.

Catalytic Properties

The hydrolytic activity of both IgV clones was saturable with increasing Aβ40 concentration (1 nM-100 μM nonradioactive Aβ40 mixed with 0.1 nM $^{125}$I-Aβ40). Kinetic parameters are reported in Table 3.

TABLE 3

Apparent kinetic parameters for Aβ40 hydrolysis by recombinant antibody fragments. Reaction rates were measured by TCA precipitation following incubation of increasing Aβ40 (0.001-40 μM) containing constant amount of $^{125}$I-Aβ40 (~300000 cpm) with IgV$_{L2}$-t 2E6 (3.75 μg/ml) or IgV$_L$-t' 5D3 (0.15 μg/ml). Kinetic constants were obtained from non-linear regression fits to the Michaelis-Menten equation ($r^2$ for IgV$_{L2}$-t 2E6 and IgV$_L$-t' 5D3, respectively, 0.99 and 0.99.

| Catalyst | Km (M) | $k_{cat}$ (min$^{-1}$) | $k_{cat}$/Km (M$^{-1}$ min$^{-1}$) |
|---|---|---|---|
| IgV$_{L2}$-t 2E6 | $8.0 \times 10^{-5}$ | $3.0 \times 10^{-1}$ | $3.7 \times 10^3$ |
| IgV$_L$-t' 5D3 | $1.7 \times 10^{-5}$ | 1.0 | $5.9 \times 10^4$ |

MALDI-MS of nonradioactive Aβ40 treated with IgV$_{L2}$-t 2E6 or IgV$_L$-t' 5D3 indicated similar product profiles. The deduced peptide that are hydrolyzed are shown in FIG. 9A and the product profiles with the IgV$_{L2}$-t as catalyst are in FIGS. 9B-9C. The prominent products were Aβ1-14 and Aβ15-40 (see FIG. 6 for observed and calculated m/z values), suggesting hydrolysis of the His14-Gln15 peptide bond. Smaller signals for the following peptide products were also detected: Aβ1-15, Aβ1-20, Aβ16-40 and Aβ21-40. The corresponding scissile bonds in Aβ40 are Gln15-Lys16 and Phe20-Ala21. Similar product profiles were evident in reaction mixtures of the longer Aβ42 peptide treated with the IgV$_{L2}$-t 2E6 (FIG. 9D-9E), except that additional minor peptide products suggesting cleavage at the Lys27-Gly28 and Gly28-Ala29 bonds were evident.

Figure 10:
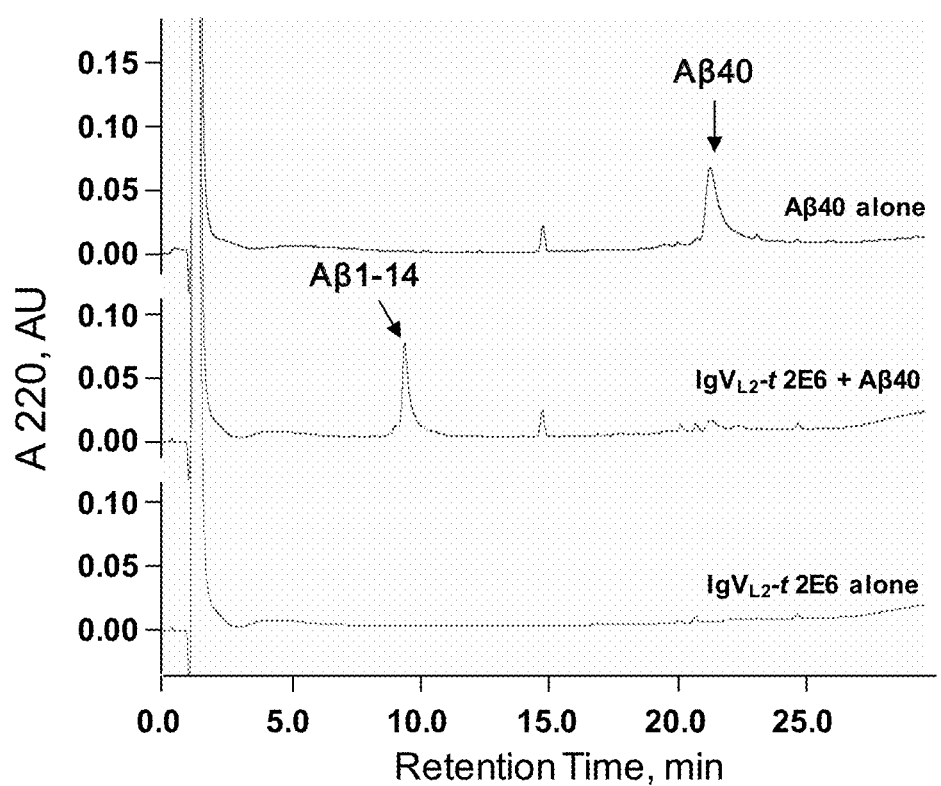
FIG. 10 depicts HPLC detection of Aβ40 fragments generated by IgV$_{L2}$-t 2E6. Aβ40 (100 µM) incubated with IgV$_{L2}$-t 2E6 (40 µg/ml) for 72 h (middle chromatogram). Top and bottom chromatograms show, respectively, the control IgV$_{L2}$-t 2E6 alone (40 µg/ml) and the control Aβ40 alone (100 µM) incubated in diluent. The peptide peaks were identified by ESI-mass spectroscopy as in Taguchi H, et al, J Biol Chem 2008, 283, 4714.

As MALDI-MS does not enable accurate quantification of the reaction products, RP-HPLC of Aβ40 treated with IgV$_{L2}$-t 2E6 also was conducted. This indicated depletion of the intact Aβ40 peak, accompanied by appearance of a major peptide product absent in control chromatograms of the IgVs alone or Aβ40 alone (FIG. 10). The product peak was identified as Aβ1-14 by ESI-MS, suggesting the His14-Gln15 bond as the major cleavage site.

Figure 11A:
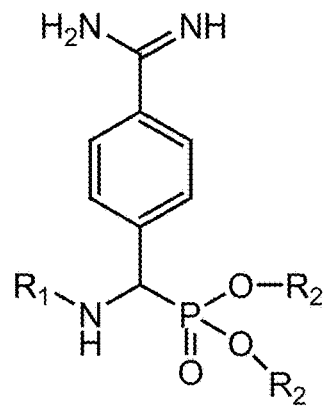
FIGS. 11A-11C illustrate inhibition of IgV hydrolytic activity by E-hapten-1.
Figure 11B:
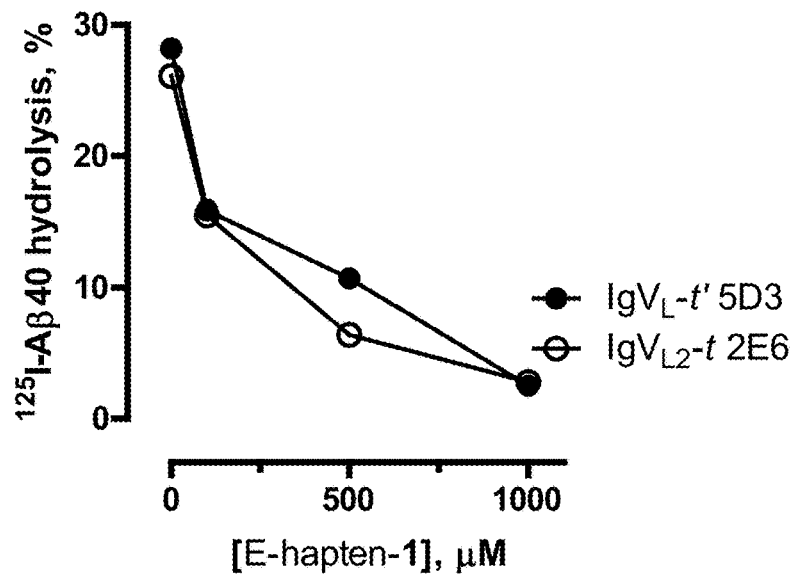
Figure 11C:
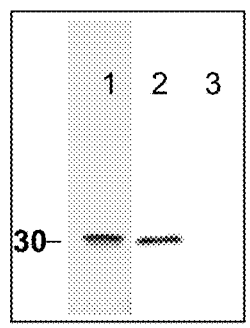

Previous studies have indicated that naturally occurring proteolytic Igs frequently utilize a serine protease catalytic mechanism entailing nucleophilic attack on the electrophilic carbonyl of peptide bonds [9]. This was the basis for covalent phage IgV selection with the electrophilic Aββ40 analog reported in FIGS. 3A-3C. To confirm the reaction mechanism, the reactivity of IgV$_{L2}$-t 2E6 and IgV$_L$-t' 5D3 with the electrophilic phosphonate diester E-hapten-1 (FIG. 11A), which was developed originally as an active site-directed covalent inhibitor of serine proteases [68], was studied. E-hapten-1 inhibited $^{125}$I-Aβ40 hydrolysis by both clones (FIG. 11B). The biotin-containing version of the phosphonate diester, E-hapten-2, formed 30 kD covalent adducts with IgV$_{L2}$-t 2E6 that were stable to boiling and SDS treatment (FIG. 11C). The control hapten-3, a poorly electrophilic analog of E-hapten-2, did not form detectable adducts with the IgV$_{L2}$-t. The results support a nucleophilic catalytic mechanism.

Figure 12A:
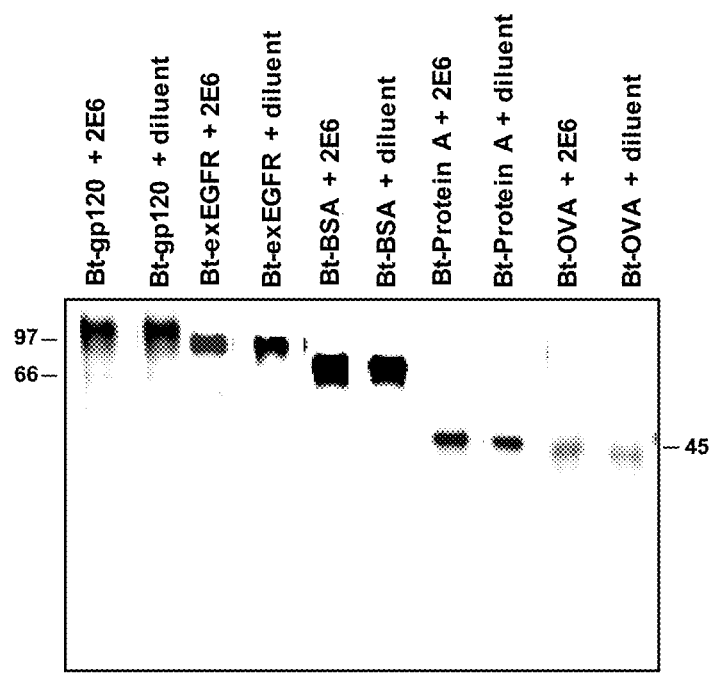
FIGS. 12A-12B illustrate that catalytic IgV$_{L2}$-t 2E6 hydrolyzes amyloid β peptide specifically.
Figure 12B:
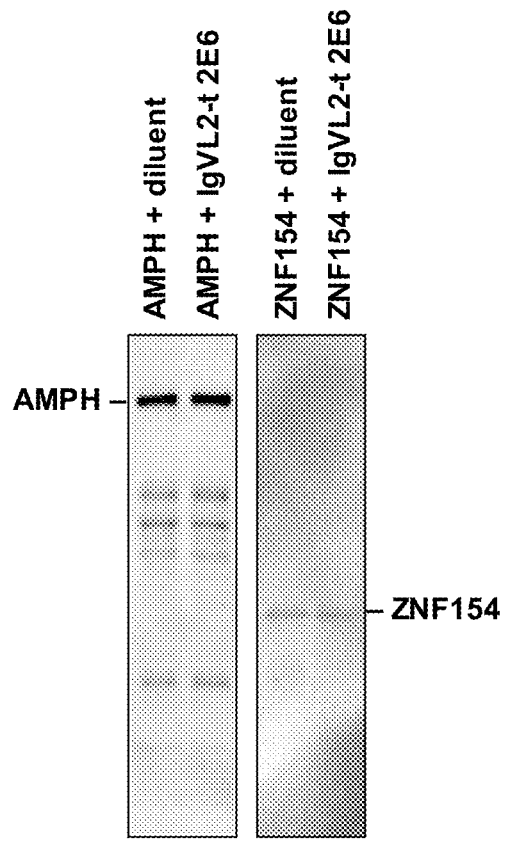

Particularly, amyloid β peptide is specifically hydrolyzed by catalytic IgV$_{L2}$-t 2E6 (FIG. 12A). No nonspecific hydrolysis was evident in streptavidin-peroxidase stained blots of reducing SDS-gels of IgV$_{L2}$-t (1 μM) reacted with biotinylated (Bt-) gp120, soluble epidermal growth factor receptor (sEGFR), bovine serum albumin (BSA), protein A and ovalbumin (OVA) (0.1 μM; 18 h). Also, blots of SDS-gels stained with anti-GST-peroxidase indicated no 2E6-catalyzed hydrolysis of amphiphysin (FIG. 12B) (AMPH; full-length human sequence with GST tag produced with Wheat Germ expression system; Abnova) and zinc finger protein 154 (ZNF154; 1-98 of human sequence with GST tag produced with Wheat Germ expression system; Abnova). AMPH and ZNF154 contain a His-Gln bond at positions 110-111 and 57-58, respectively. Intact AMPH and ZNF154 bands are indicated. Several impurities derived from the recombinant AMPH were also detected. No appreciable hydrolysis of the intact proteins was detected.

Figure 13:
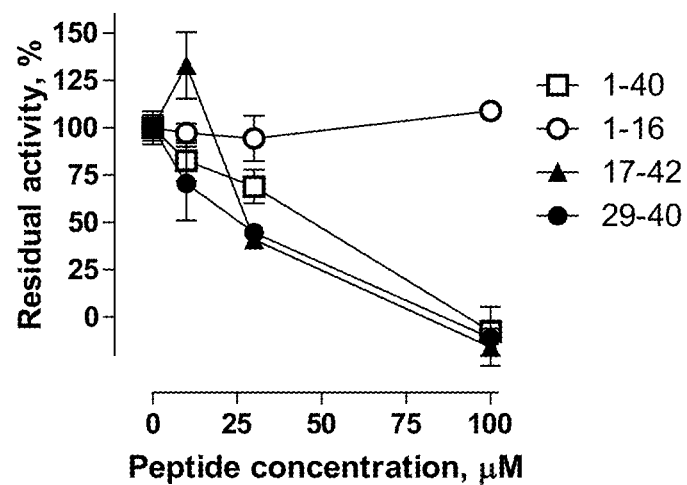
FIG. 13 illustrates the molecular basis for amyloid β peptide specificity of catalytic IgVL2-t 2E6. The results from screening synthetic Aβ peptide fragments for the ability to inhibit IgV-mediated $^{125}$I-Aβ40 hydrolysis competitively are shown. $^{125}$I-Aβ40, ~30,000 cpm (~0.1 nM); 2E6, 3 µg/mL; 3 hours at 37° C. in 10 mM PBS, pH 7.4, containing 0.1 mM CHAPS and 0.1% BSA. Activity in the absence of peptide, 2592±534 cpm/hour.

The noncovalent binding determinant for IgV$_{L2}$-t 2E6 was determined by screening synthetic Aβ peptide fragments for the ability to inhibit IgV-mediated $^{125}$I-Aβ40 hydrolysis competitively (FIG. 13). Activity in the absence of a competitor peptide was 2592±534 cpm/hour. Aβ fragments corresponding to residues 17-42 and 29-40 inhibited 2E6-catalyzed $^{125}$I-Aβ40 hydrolysis as potently as full-length Aβ1-40, indicating that the epitope composed of residues 29-40 is the primary determinant responsible for noncovalent binding to the IgV. The noncovalent binding determinant for IgV$_{L2}$-t 2E6 is remote from the major cleavage sites for Aβ40 and Aβ42 (FIG. 9E).

Example 2

Catalytic Igs to *Staphylococcus aureus* Antigens
Polyclonal IgG-Catalyzed Hydrolysis of Efb

*S. aureus* possesses an arsenal of proteins dedicated to subverting mammalian adaptive and innate immune responses [46,69,70]. The potent immunmodulatory effects of these proteins facilitate evasion of host immune responses by the bacteria. Efb, a secreted protein interferes with complement function (complement-mediated lysis and opsonophagocytosis) [71,72], platelet function [73,74] and delays wound healing as tested in animal models [75]. Efb has also been implicated in bacterial adhesion to host cell surfaces, and conventional Igs that block the binding of Efb to fibrinogen and prevented Efb-mediated inhibition of platelet aggregation have been described [76].

Figure 14:
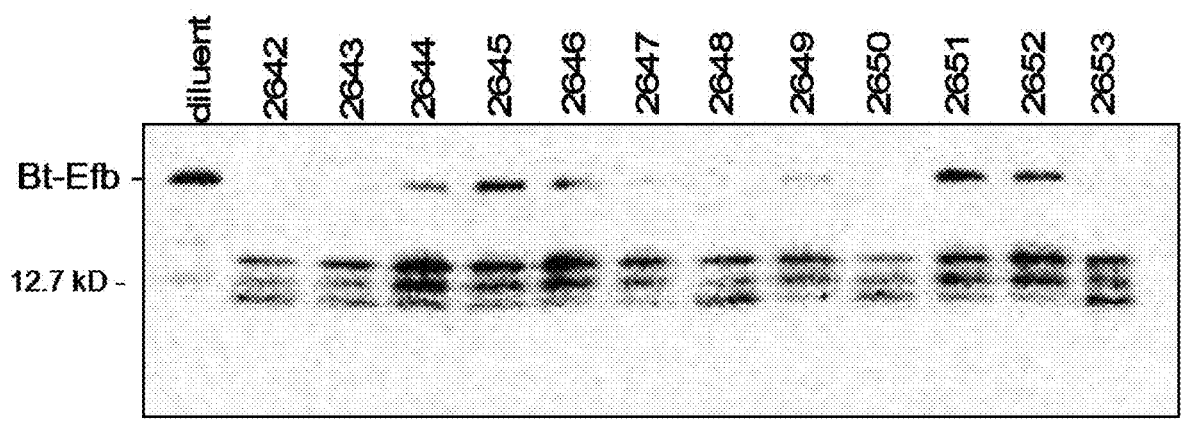
FIG. 14 illustrates Efb hydrolysis by IgG. Shown is a streptavidin-peroxidase-stained blot of a reducing SDS-electrophoresis gel showing cleavage of biotinylated Efb (0.1 µM) by affinity-purified IgG from 12 healthy adult subjects (0.35 µM) after a 20 h incubation (reaction volume 20 µl). Diluent lane represents biotinylated Efb incubated in the absence of IgG under identical conditions.
Figures 15, 16:
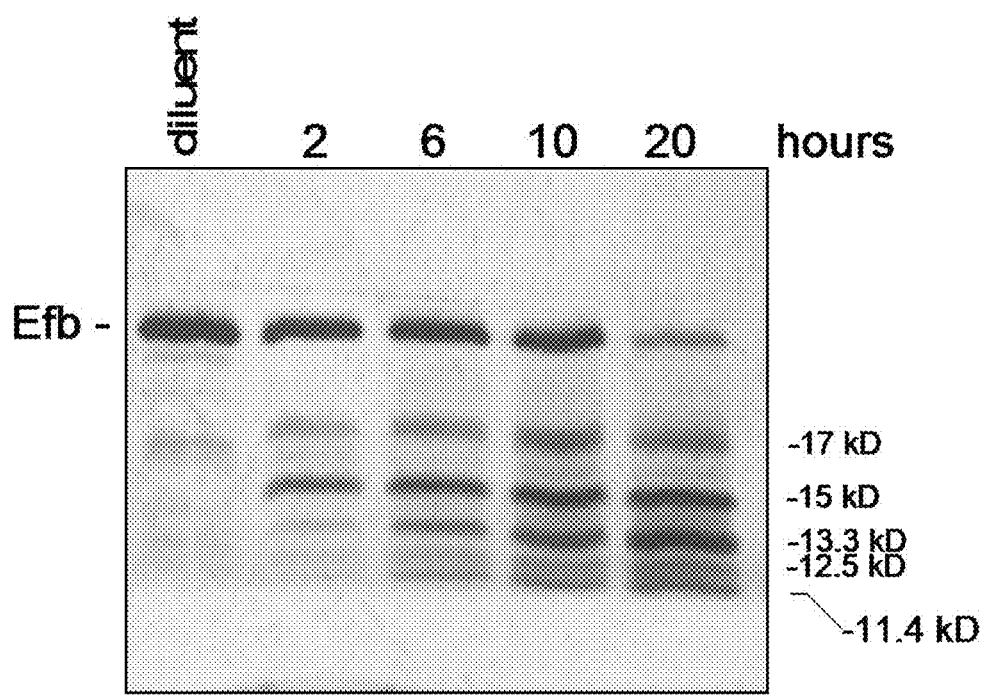
FIG. 15 illustrates the time-dependent cleavage of biotinylated Efb by pooled human IgG. Shown is a silver stained SDS-electrophoresis gel (15%; run under reducing conditions) demonstrating Efb (0.1 µM) cleavage by affinity purified IgG (45 µg/ml). Product masses are indicated on the right. Diluent lane, Efb incubated in the absence of IgG.
FIG. 16 illustrates the identification of peptide bonds cleaved by pooled polyclonal IgG. Efb (12 µg/ml) was incubated for 20 h with pooled polyclonal serum IgG (N=12 humans, 57 µg/ml). The reaction mixture was subjected to reducing SDS-PAGE (20% gels) and transferred onto a PVDF membrane. Coomassie stained product bands were sequenced by Edman's degradation. Shown is the Efb amino acid sequence with scissile bonds indicated by arrows. Bold region represents the N-terminal His tag sequence.

In the present invention, polyclonal Ig preparations were purified from serum of 12 adult humans without clinical symptom of *S. aureus* infection at the time of blood donation (6 males and 6 females). Sera were subjected to affinity chromatography on immobilized anti-human IgM antibodies (for preparation of IgM) or immobilized anti-human IgA antibodies (for the preparation of IgA) as described [9,11]. This procedure yielded electrophoretically homogeneous IgM and IgA as determined by SDS-electrophoresis of Coomassie-stained gels and via Western blotting using antibodies specific to μ or α chain as described [9,10]. IgG was purified using immobilized Protein G as described previously [5]. Efb hydrolysis by individual Ig preparations was studied using biotinylated Efb (Bt-Efb; prepared from recombinant Efb expressed in *E. coli*; [71,77]) as substrate. All of the IgG, IgA and IgM from the 12 subjects degraded Bt-Efb, evident from disappearance of the parent 19 kDa band and appearance of three biotin-containing bands with nominal mass values of 14, 10 and 7 kDa, respectively (note that Bt-Efb contains only 1-2 moles biotin/mole protein, and the absence of biotin in certain degradation fragments may preclude their detection). IgG possessed the most efficient catalytic activity (FIG. 14). Efb hydrolysis was observed at IgG concentrations as low as 0.1 μM. The activity levels varied widely in different human subjects (Efb hydrolysis ranging between 20-100% of the available Efb). Non-biotinylated Efb was also cleaved by IgG; The hydrolysis was time-dependent and readily noticeable as early as 2 hours after initiating the incubation (FIG. 15). To identify the Efb peptide bonds susceptible to cleavage by IgG, the reaction products separated by electrophoresis were subjected to N-terminal sequencing. All of the bonds hydrolyzed by IgG contained a basic residue (Lys/Arg) at the P1 position (FIG. 16). One of the IgG-susceptible bonds is located in the C3b-binding region of Efb ($Lys_{100}$-$Thr_{101}$).

Figure 17:
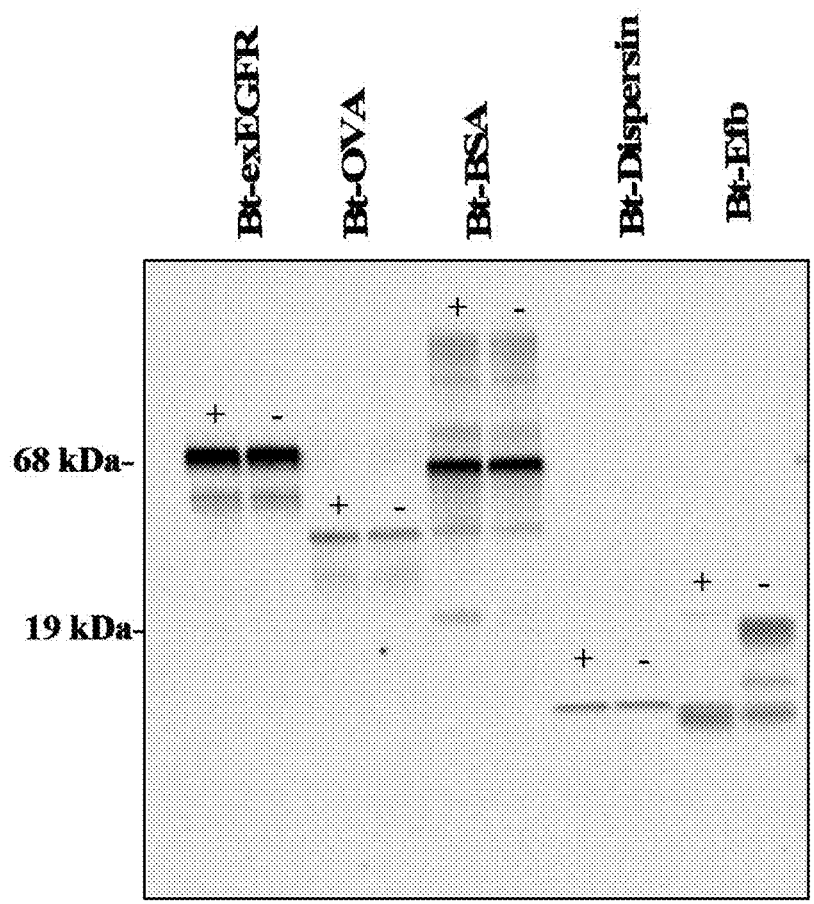
FIG. 17 illustrates that Bt-Efb is cleaved selectively by IgG. Shown is a streptavidin-peroxidase stained blot of a reducing SDS-electrophoresis gel of biotinylated extracellular domain of epidermal growth factor receptor (Bt-ex-EGFR; 0.25 µM), ovalbumin (Bt-OVA; 0.25 µM), bovine serum albumin (BSA), Dispersin (0.25 µM) and Efb (1.1 µM) incubated in the presence (+) or absence (−) of pooled IgG (0.5 µM) for 20 h.

Under identical conditions, several non-S. aureus control proteins were not cleaved by IgG (FIG. 17). Hydrolysis of the control proteins by the promiscuous serine protease trypsin was readily detectable. The absence of indiscriminate proteolytic activities in the IgG preparations suggests that trace protease contamination do not explain the observed Efb cleavage reaction. Moreover, the IgG, IgA and IgM preparations were subjected to FPLC gel filtration in denaturing solvent (6 M guanidine hydrochloride; to remove any non-covalently-associated proteases) followed by dialysis against PBS (to renature the antibodies). The IgM (900 kDa), IgG (150 kDa) and IgA fractions (160 kDa) recovered from the column displayed the proteolytic activity using several model tripeptide substrates [9,10]. Fab fragments prepared from IgG and IgM have also been shown to retain the proteolytic activity, indicating that the catalytic site is located in the V domains.

Figure 18:
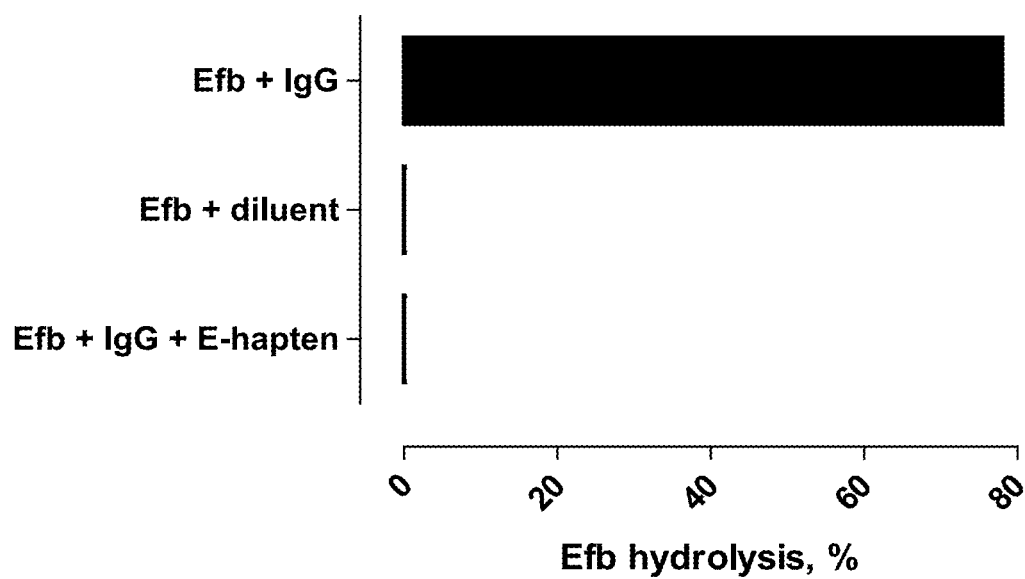
FIG. 18 illustrates serine-protease inhibitor blovks IgG-mediated catalytic activity. Efb (0.7 µM) was incubated with pooled polyclonal IgG (1 µM) in the presence and absence of the serine protease inhibitor E-hapten 2 (shown in FIG. 11A; 100 µM).

Four classes of proteases are known: serine proteases, thiol proteases, acid proteases and metalloproteases. E-hapten 2 (structure shown in FIG. 11A) contains an electrophilic phosphonate group that binds irreversibly to the catalytic site of serine proteases and thereby inhibits their catalytic activity. This compound was a potent inhibitor of IgG-catalyzed Efb hydrolysis (FIG. 18). Inhibitors of metalloproteases (EDTA and 1,10-phenanthroline), cysteine-proteases (iodoacetamide), and acid-proteases (pepstatin) were not effective or marginally effective. Like other naturally occurring catalytic Igs, these results suggest that catalytic Igs to Efb use a serine protease-like mechanism of catalysis.

Identification of Efb-Hydrolysing IgVs

Figure 19A:
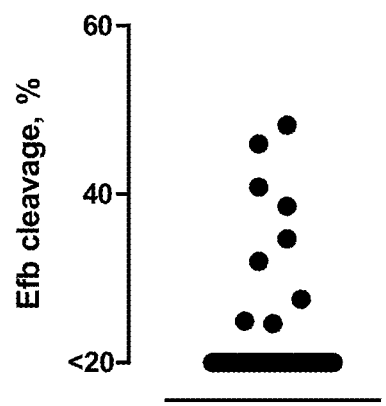
FIGS. 19A-19B illustrate the identification of Efb-hydrolyzing antibody fragments.
Figure 19B:
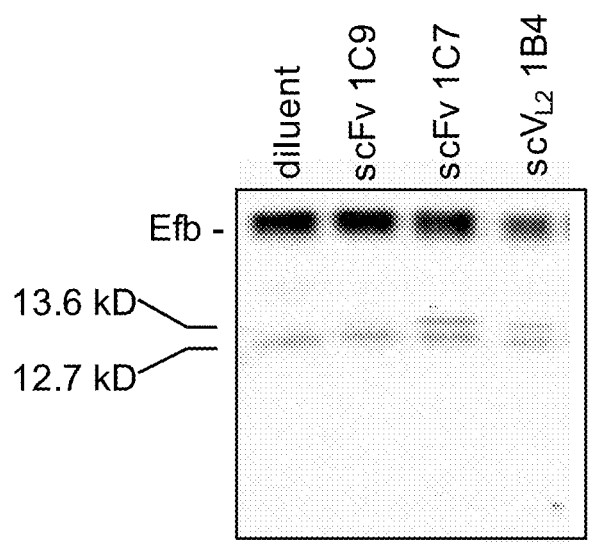
Figure 20A:
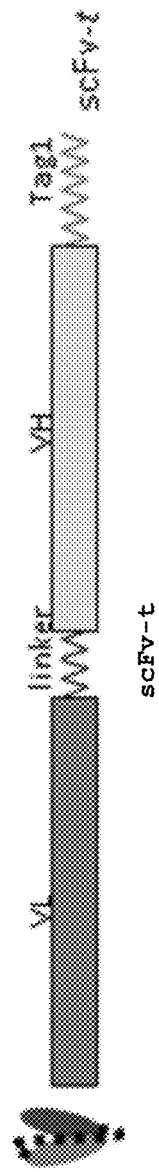
Figure 21A:
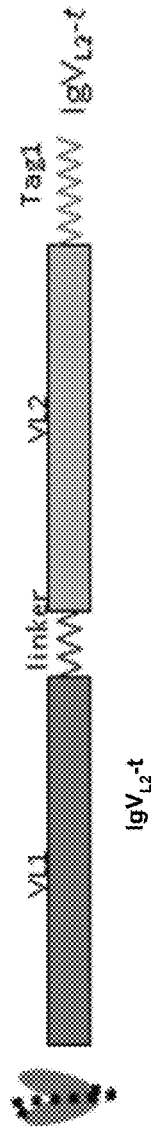

Efb hydrolysis was tested by purified IgV constructs from 42 randomly picked clones from our human IgV library ($\sim 10^7$ clones). The majority of clones in this library (83%) are scFv constructs mimicking the physiological structures of Ig combining sites. A minority (17%) of clones are IgVs with aberrant structures including $IgV_{L2}$-t and $IgV_L$-t' (see EXAMPLE 1). Efb-hydrolysis was studied by the SDS-electrophoresis method using the Bt-Efb substrate (0.1 μM) incubated with IgVs for 20 hours as described above. Blots of the gels were stained with streptavidin-peroxidase. Substrate consumption was measured by densitometry of the intact Bt-Efb band compared to the control incubation conducted in the absence of IgV under otherwise the identical conditions. IgVs displayed >20% cleavage were considered positive (FIG. 19). The catalytic IgV clones identified were 1B4, 1B10, 1G2, 1G5, 2B4, 2B6, C6, 2C7, and 2E6 (range, 25-49%; median, 35%; mean, 35%; SD, 9%). The finding of recombinant IgVs with Efb hydrolyzing activity further validates the existence of the catalytic Igs to this protein in the expressed human repertoire.

Two catalytic clones (1C7, 1B4) were subjected to di-deoxy nucleotide sequencing, revealing one to be an scFv construct (clone 1C7) and the other to be a $IgV_{L2}$-t construct (1B4) (FIGS. 20A-20B, 21A-21B). Comparison of the cDNA sequences of scFv 1C7 and $IgV_{L2}$-t 1B4 with their closest germline V gene counterparts revealed the presence of mutations in the V domains of both constructs.

Catalytic Neutralization of the S. aureus Virulence Factor Efb

Complement activation and deposition of C3b on the surface of S. aureus is important in the opsonophagocytic clearance of the bacteria. Efb interferes strongly with complement activation, impeding bacterial phagocytosis and aiding bacterial survival in the early stages of the infection before a protective capsule has been formed. In addition, Efb is an inhibitor of Ig-dependent complement-mediated lysis [71,77]. The binding of complement component C3b by Efb-IgG reaction mixtures was determined. Blots of the reaction mixtures were probed with digoxigenin-labeled C3b as described previously [77]. Efb incubated with purified catalytic IgG lost all C3b binding activity (FIG. 22A). Moreover, Efb treated with a catalytic IgG preparation lost its ability to inhibit complement-dependent RBC lysis (FIG. 22B). The data suggest that catalytic Igs neutralize Efb.

Catalytic Igs to Additional S. aureus Virulence Factors

S. aureus has evolved numerous polypeptide virulence factors that are important in establishment and progression of infection. The known virulence factors include proteins that facilitate bacterial adhere to extracellular matrix components and host cell surfaces; exert toxic effects on host cells and help the bacterium evade host immune defenses [46,69,78-82]. Of particular interest are the factors expressed by the USA300 isolate, which is responsible for most community-acquired infections in the U.S. [83].

The virulence factors can be classified as adhesions, toxic factors and immunomodulators. Adhesins are attractive targets of Igs for the purpose of impeding bacterial colonization [82]. Several bacterial adhesions are characterized by an LPXTG motif, such as Sdr family adhesins. The transpeptidases Sortase A and B covalently link the threonine of this sequence to cell wall-associated pentaglycine, anchoring the proteins to the cell wall. The important role of these adhesins is supported by evidence that S. aureus sortase mutants are impaired in the ability to cause acute lethal disease, abscess formation in internal organs, infectious arthritis and infectious endocarditis in mouse and rat models [84,86]. Additional important adhesins are Clumping factor A and B (ClfA, ClfB), which are structurally-related fibrinogen (Fg) binding proteins [87,88]. ClfB also binds cytokeratin 10 [89,90]. The fibronectin (Fn)-binding adhesins, FnbpA and FnbpB, also have a Fg-binding domain and compete with ClfA for Fg binding [91]. FnbpA overexpression in ClfA and ClfB deficient S. aureus permits bacterial-Fg interactions [91].

Panton Valentine Leukocidin (PVL), a bi-component exotoxin assembled from two polypeptides (LukS-PV and LukF-PV) is an important S. aureus toxin that forms pores in membranes and lyses various host cell types, including neutrophils and macrophages. PVL expressing isolates are thought to cause more severe infections compared to PVL-negative strains. A virulence factor role for PVL was described in a mouse pneumonia model [92]. S. aureus alpha-toxin (Hla) is a potent hemolytic, cytotoxic, and dermonecrotic toxin. It lyses erythrocytes, mononuclear cells, platelets, epithelial and endothelial cells [93]. Cell death occurs because of membrane damage [94,95]. Most S. aureus strains express alpha-toxin, but the level of expression can vary.

S. aureus possesses an arsenal of immunomodulatory proteins. One example is Efb described in the preceding section. Another is Map (also named Eap), a secreted protein that binds host surfaces and can also re-bind to the bacteria. It has profound effects on T cell function in vitro and in animal models [96,97]. It also reduces neutrophil migration [98] and induces proinflammatory cytokine production from PBMCs [99]. Protein A is secreted protein and is also found linked covalently to the cell wall. It binds the V domains of certain VH3 family Igs and is the prototypical B cell superantigen. Protein A acts directly on B cells, and by inducing apoptosis of VH3+ B cells, it causes dramatic changes in the expressed Ig repertoire [79,81]. Protein A also binds the Fc region of certain IgG subclasses.

The ability of Igs from adult humans with no evidence of clinical *S. aureus* infection to catalyze the hydrolysis of the following *S. aureus* virulence factors was examined: Protein A, Map 19, ClfA, LukF and SdrE. Distinct levels of hydrolysis of these proteins by the IgM, IgA and IgG preparations was observed. IgA preparations tended to show greatest activity for all substrates. Example data are shown in FIG. 23. No noticeable hydrolysis of ClfB or LukS was evident at the Ig concentrations tested (150 µg/ml). Previous studies have reported the superantigenic character of Protein A with respect to Ig binding activity [80,81]. For our studies, the Fc-binding activity of Protein A was removed by treatment with iodine monochloride as described previously [79,100]. The resultant I-Protein A preparation is known to bind $V_H3$ family immunoglobulins via interactions at the V domains.

Figure 24A:
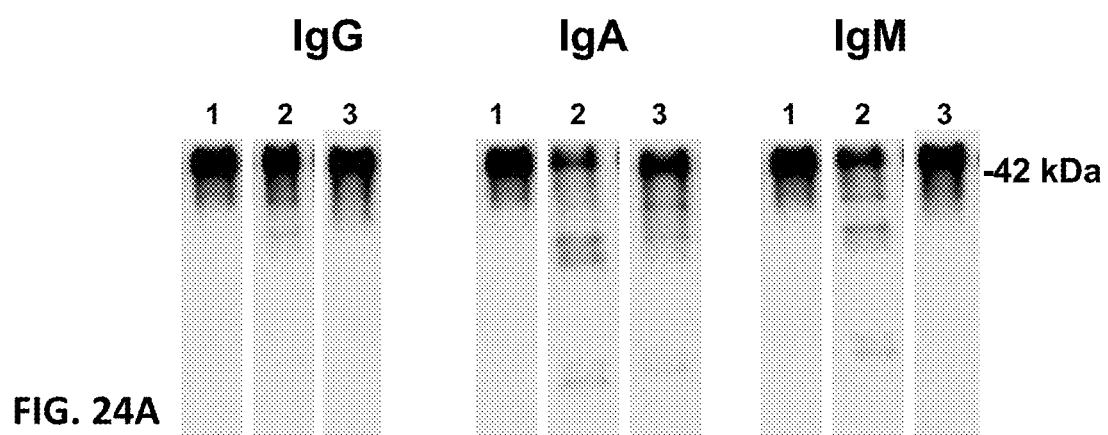
FIGS. 24A-24B illustrate the hydrolysis of (FIG. 24A) Bt-SdrE and (FIG. 24B) Bt-Map19. Bt-proteins (0.1 µM) were incubated 15 h at 37° C. in diluent (Lane 1) or Igs (1 µM) purified from pediatric subjects without (Lane 2), or with deep-bone S. aureus infections (Lane 3). Reaction mixtures were then subjected to SDS-PAGE electrophoresis and Bt-proteins were visualized by streptavidin-peroxidase staining.
Figure 24B:
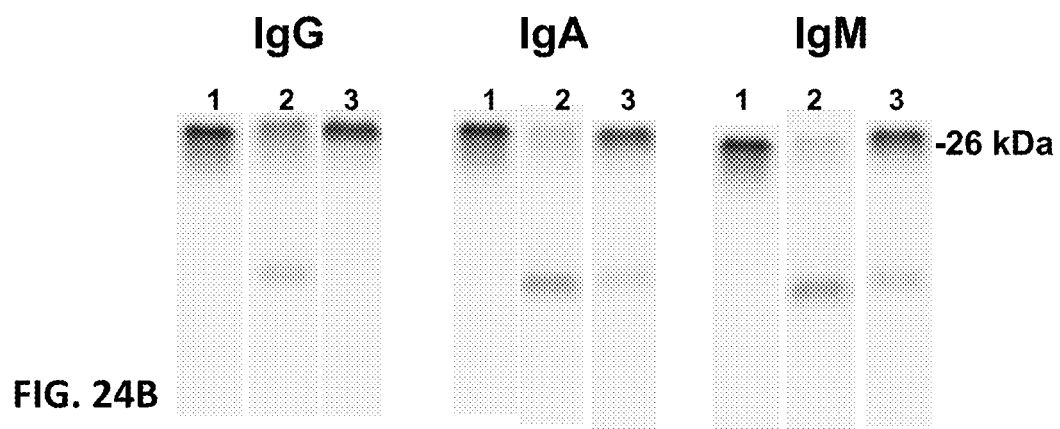

The hydrolysis of Map19 and SdrE by Igs from pooled sera from pediatric subjects without *S. aureus* disease and children diagnosed with deep-bone *S. aureus* infections (FIG. 24) was compared. The Igs from children with deep-bone infections were poorly hydrolytic compared to disease-free children. For example, the Map19 hydrolysis activity levels of Igs from disease-free vs deep-bone infection were: IgG, 1.0±0.2 vs<0.4; IgM, 6.9±0.1 vs 0.5±0.2; IgA, 6.7±0.3 vs<0.4 nM/h/µg Ig.

These observations suggest that catalytic Igs to *S. aureus* virulence factors are widely distributed in humans. The reduction in catalytic Igs observed in individuals with bacterial disease is interesting, suggesting that an impaired defense due to the catalytic Igs may be a factor in progression of infection and development of clinical disease.

These results also suggest that Efb, Map19 and SdrE may have B cell superantigenic characters, i.e., they are recognized by catalytic Igs without requirement for antigen-specific stimulation. The reduction of catalytic Igs in children with clinical *S. aureus* is consistent with findings that synthesis of Igs to superantigens is decreased following exposure to the superantigen. In the present inventions, additional support for the superantigenicity of certain *S. aureus* proteins was obtained by examination of pooled Igs from mice maintained in a pathogen-free facility. Efb was cleaved at readily detectable levels by all class of Igs from the mice (IgG 5.6±1.1, IgM 5.9±1.3, IgA 32.7±1.3 nM/h/µg Ig). Following experimental *S. aureus* infection, IgG preparations from the mice displayed undetectable Efb-cleaving activity (<3.7 nM/h/µg Ig) and IgA displayed reduced Efb-cleaving activity (6.9±1.5 nM/h/µg Ig). The IgM activity was maintained at nearly unchanged levels (5.1±0.1 nM/h/µg IgM).

Figure 25A:
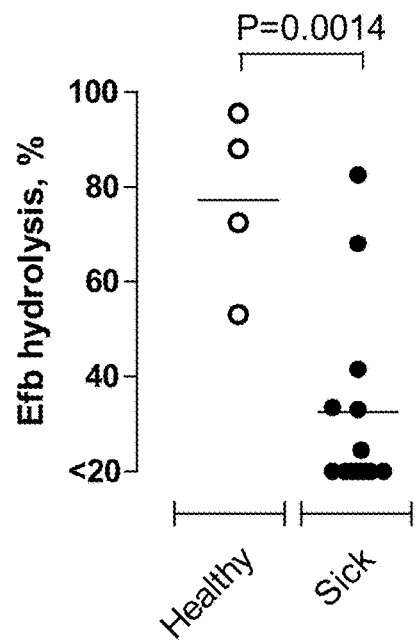
FIGS. 25A-25D illustrate the Efb hydrolyzing activity of IgG in humans and mice with and without S. aureus infection.

Efb Hydrolyzing Activity of IgG in Humans and Mice with and without *S. aureus* Infection Polyclonal antibody donors were identified among healthy children and children hospitalized for an *S. aureus* infection. Catalytic antibodies suitable for therapy of *S. aureus* infection were prepared from these donors and from aseptic mice (pool of 10). The percent of Efb hydrolysis by IgG was compared between healthy and *S. aureus* infected children (FIG. 25A). Efb hydrolyzing activity was measured by SDS electrophoresis assay using Bt-Efb as substrate as in FIG. 14. The percent of Efb hydrolyzing activity by IgG was at least 50% for all instances. Some hydrolytic activity from infected children was measured within the range of activity from healthy children donors.

Figure 25B:
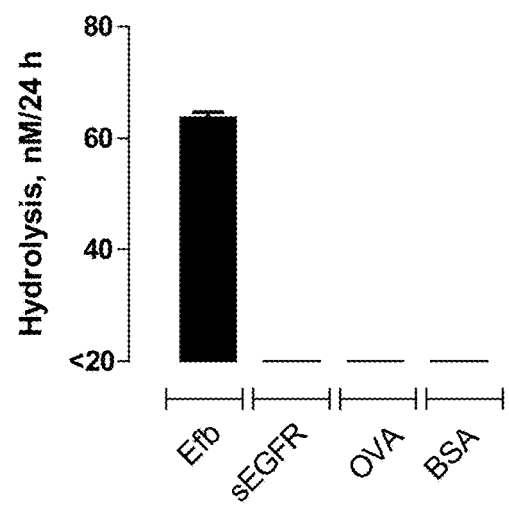
Figure 25C:
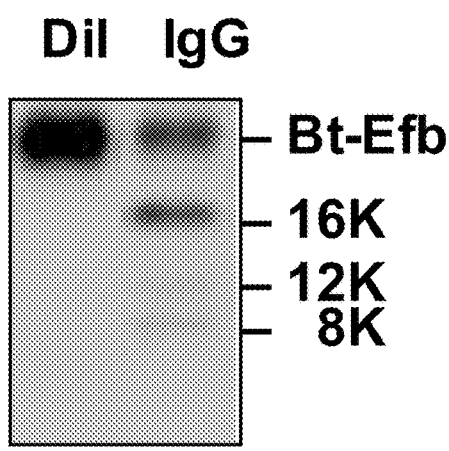
Figure 25D:
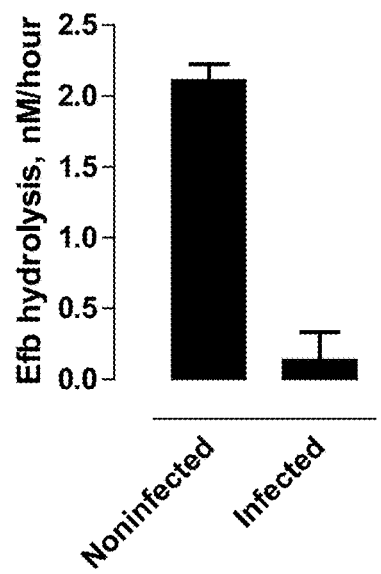

Selective Efb (Bt-Efb) hydrolysis by IgG from aseptic mice (pool of 10) compared to Bt-sEGFR, BT-OVA and BT-BSA over a period of 24 hours also was demonstrated (FIG. 25B). As these mice were maintained under aseptic conditions, the hydrolytic activity is an innate immunity function not requiring prior exposure to *S. aureus*. Streptavidin-stained blots of SDS electrophoresis gel lanes showing Bt-Efb incubated with diluent or IgG shows hydrolysis of Bt-Efb (FIG. 25C). Efb hydrolyzing activity of IgG obtained from *S. aureus* (strain USA300) infected mice 21 days post infection was about 10 times greater compared to noninfected controls (FIG. 25D)

Example 3

Polyclonal Catalytic IgMs to Hepatitis C Virus Coat Protein E2
Hepatitis C Virus (HCV)

The E2 coat protein expressed by HCV is thought to be essential for viral infection by virtue of its role in host cell binding [101]. Proposed cellular receptors for HCV E2 are CD81 and the LDL receptor. E2 contains hypervariable regions and comparatively conserved regions. Igs to the hypervariable regions are frequent in infected individuals [53]. Conventional non-catalytic Igs to E2 have been suggested to be important in control of virus infection [53]. Certain monoclonal Igs to E2 neutralize the virus and are under consideration for therapy of HCV infection [54].

A pooled Ig preparation consisting of IgM class antibody was obtained from serum of 10 human subjects with asymptomatic HCV infection. These subjects were positive for the NS3, NS4 HCV antigen determined by a commercially available kit (Abbott laboratories). Sera were subjected to affinity chromatography on immobilized anti-human IgM antibody as described previously [9]. The Ig preparation obtained was electrophoretically homogeneous as determined by SDS-electrophoresis of Coomassie-stained gels and immunoblotting using anti-µ antibodies. HCV E2 hydrolysis by the Ig preparation was studied using two recombinant E2 preparations as substrates: commercially available E2 containing the 26 kD glutathione-S-transferase tag (E2-GST; baculovirus expression system), and recombinant E2 containing the 8-residue Flag tag (E2-FL; expressed in HEK293 cells; see ref [102]). The latter substrate was purified partially by affinity chromatography using immobilized anti-FL antibody by methods known to one skilled in the art. Hydrolysis of these substrates was determined by SDS-electrophoresis followed by staining of the gels with commercially available anti-GST antibody, anti-FL antibody or anti-E2 antibody.

Figure 26A:
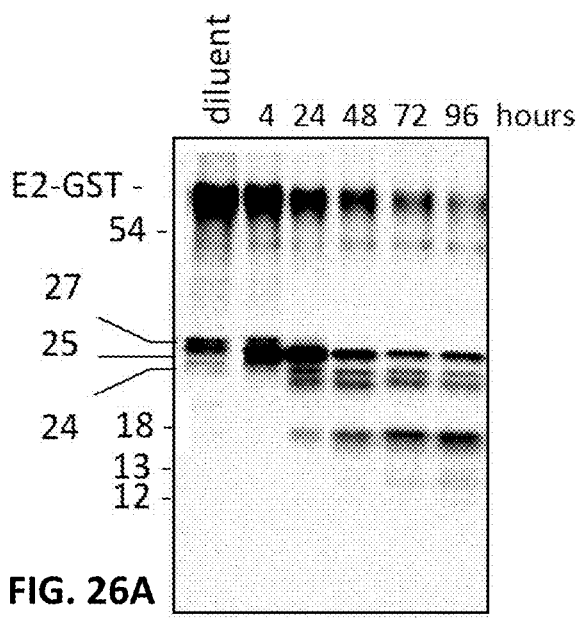
FIGS. 26A-26D illustrate the hydrolysis of E2 by IgM from HCV infected humans.
Figure 26B:
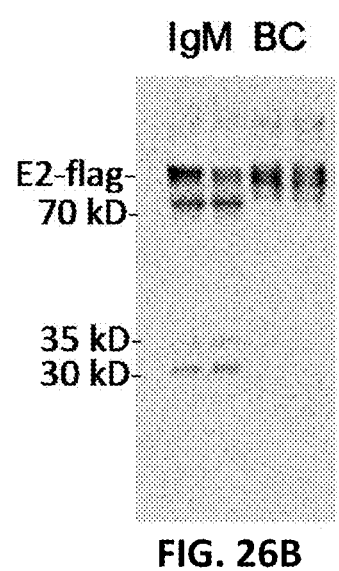

The pooled IgM from HCV+ subjects hydrolyzed E2-GST, evident from time-dependent disappearance of the intact substrate band and appearance of the multiple anti-GST stainable bands with mass values smaller than E2-GST (FIG. 26A). IgM cleaved E2-FL also, determined by anti-FL staining or anti-E2 staining of the gels (FIG. 26B).

Figure 26C:
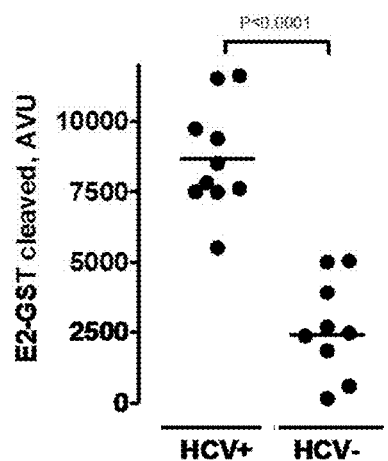
Figure 26D:
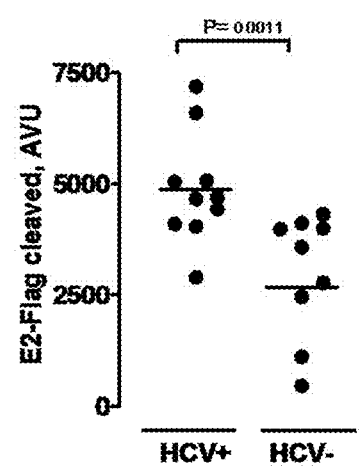

Next, the E2 hydrolyzing activities of IgM preparations obtained from individual serum samples from HCV-infected (n=10) and uninfected (n=9) subjects were determined (FIG. 26C). The hydrolytic activity was expressed as the decrease in the intact E2-GST or E2-FL band intensity determined by densitometry using the diluent control as reference (E2-GST or E2-FL incubated in the absence of IgM). The E2 hydrolyzing activity of IgM preparations from the HCV+ subjects was greater than the HCV negative subjects using E2-GST or E2-FL as the substrates (FIG. 26D). Widely varying levels of catalytic activity were evident in different donors within the two groups of subjects.

Figure 27:
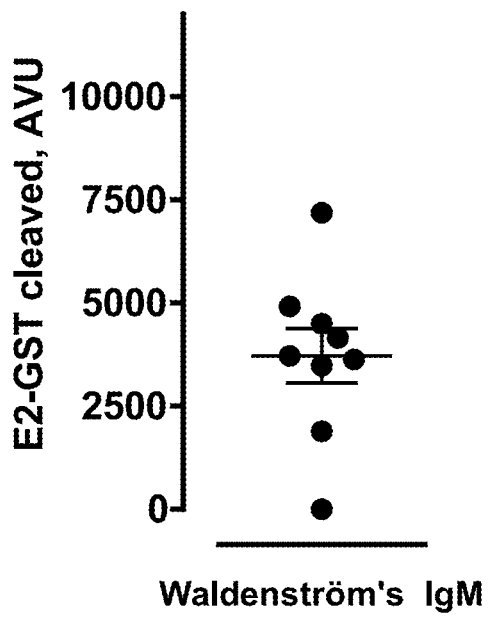
FIG. 27 illustrates the hydrolysis of E2-GST by monoclonal IgM preparations. E2-GST (75.5 µg/mL) incubated with Waldenstrom's IgM (75.5 µg/mL) for 48 h was subjected to SDS-electrophoresis, and E2-GST hydrolysis was quantified as in FIGS. 26A-26D. Each point represents one study subject.
Figure 28:
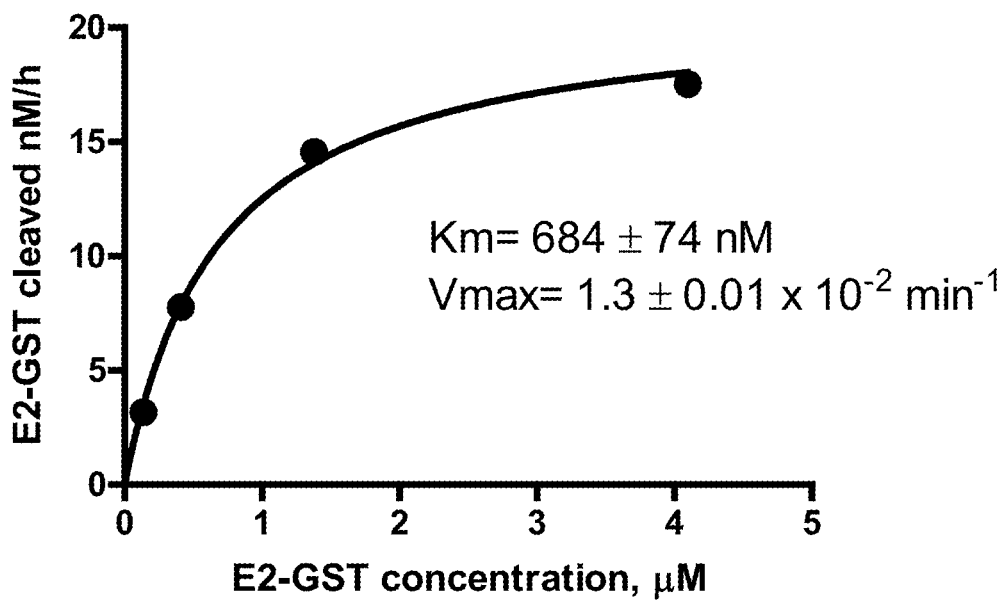
FIG. 28 illustrates the apparent kinetic parameters for E2-GST hydrolysis by IgM from HCV infected humans. A pooled IgM preparation from HCV infected humans (n=10; 25 µg/mL) was incubated with increasing concentrations of E2-GST (0.14-4.1 µM), and E2-GST hydrolysis was determined as described in FIG. 23. Km and Vmax values were obtained from the least-square-fit of the velocity (V) vs E2-GST concentration data to the Michaelis-Menten equation, V=Vmax·[E2-GST]/(Km+[E2-GST]) ($r^2$ 0.992); Vmax, [E2-GST], and Km denote, respectively, the maximum velocity, initial concentration of E2-GST, and Michaelis constant.

To validate the catalytic activity, the hydrolysis of E2-GST by 9 monoclonal IgM preparations obtained from humans with Waldenström's macroglobulinemia was tested as described [103]. Several IgMs displayed detectable E2-GST hydrolyzing activity (FIG. 27). Apparent kinetic constants for the pooled IgM from HCV+ subjects were determined at varying concentrations of E2-GST (FIG. 28). From the fit of the rate data to the Michaelis-Menten equation, values of Km and maximal velocity (Vmax) were, respectively, 684 nM and $1.3 \times 10^{-2}$ moles E2-GST/mole IgM/min.

Homogeneous recombinant IgVs to E2 can be readily obtained by covalent selection of the phage displayed IgV libraries using an electrophilic E2 analog as demonstrated for other antigens in EXAMPLES 1 and 4. For this purpose an electrophilic analog of biotinylated E2-GST (E-E2-GST) was prepared. The E-E2-GST was obtained by successive acylation of exposed amino groups with N-hydroxysuccinimide esters of 6-biotinamidohexanoic acid and diphenyl N-suberoylamino(4-amidinophenyl)methanephosphonate, followed by gel filtration purification at each step by methods described in refs [56,104]. MALDI-TOF MS of the biotinylated E2-GST, E-E2-GST product and the starting E2-GST protein indicated a mass increase of 700.4 for the biotin containing protein and 6900.1 for the phosphonate containing protein, corresponding to 2 biotin and 13 phosphonate groups per E2-GST molecule (FIGS. 29A-29D).

Example 4

Catalytic and Neutralizing Igs to HIV Gp120
Neutralizing Igs from Non-Infected Humans Over 33 million humans are infected with HIV. No effective vaccine for HIV is available. Progression to AIDS occurs at variable rates in infected subjects. Without treatment, ~50% of infected subjects die in 10 years [105]. There is consensus that the variable rates of disease progression derive at least in part from discrete immunological factors. Innate and adaptive immune responses help protect against the virus (e.g., [106-108]). Knowledge of resistance factors to HIV can help guide improved treatment and development of a preventive vaccine.

Effective control of HIV by the immune system is thwarted by: (a) rapid sequence diversification of the immunogenic epitopes in its coat protein gp120; and (b) the lack of robust adaptive responses to conserved epitopes of viral protein important in virus-host cell interactions. The immune system generally fails to produce Igs to conserved gp120 epitopes with sufficient neutralization potency and breadth to control HIV fully. Ig epitope specificity is an important property governing neutralization. Although rare, neutralizing monoclonal antibodies (MAbs) to gp120 and gp41 have been identified. The best known are: MAb b12 directed to a gp120 determinant overlapping the CD4bs [109]; MAb 2G12 to a mannose-dependent gp120 epitope [110,111]; and MAb 2F5 to a gp41 epitope involved in forming the fusogenic gp41 intermediate [112]. These MAbs neutralize many clade B strains and they protect macaques against challenge with clade B SHIV strains (SIV engineered to express HIV env) [113-115]. However, they are often ineffective against HIV belonging to other clades, e.g., clade C strains responsible for >50% of all infections [113].

Igs with epitope specificity similar to MAbs b12, 2G12 or 2F5 are usually not detected in chronically infected HIV subjects. Most Igs in infected individuals are directed to epitopes that mutate rapidly or are inaccessible sterically, allowing infection to progress. Often, the Igs recognize the immunodominant, hypermutable epitopes located within V3 residues 306-325 [116,117]. These Igs usually do not neutralize CCR5-dependent strains or strains with divergent V3 sequences.

gp120 contains a B cell superantigen site recognized by preimmune Igs without requirement for adaptive B cell maturation [43]. B cell superantigen recognition is mediated mostly by contacts at Ig V domain FR residues [118,119]. Most conventional Ig-antigen contacts, in contrast, occur at the CDRs. Peptide mapping studies suggest that the gp120 superantigen site is discontinuous determinant, composed of residues 241-250, 341-350 and 421-440 [44].

Figure 30A:
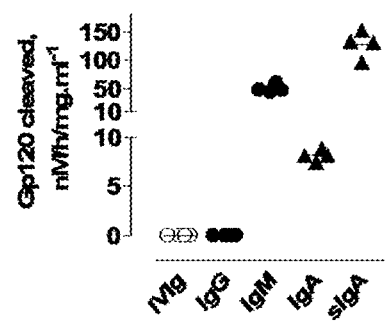
FIGS. 30A-30C illustrates hydrolysis of gp120 by IgAs and other antibody classes.
Figure 30B:
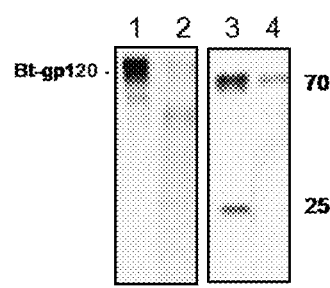
Figure 30C:
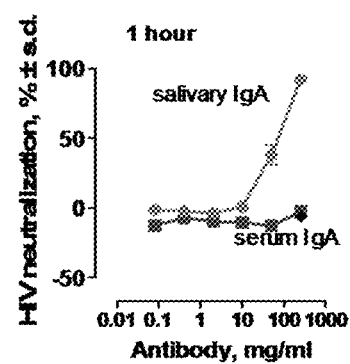

It was observed that IgMs [120] and IgAs [121] from non-infected humans catalyze the hydrolysis of gp120. From initial rate data, the average turnover number ($k_{cat}$) for a polyclonal IgM preparation was 2.8/min. Salivary IgAs, and to a lesser extent, serum IgAs from uninfected humans hydrolyzed gp120 (FIGS. 30A-30B). IgGs did not. Neutralization potency was modest, determined by p24 enzymeimmunoassay using peripheral blood mononuclear host cells. HIV strain ZA009 was neutralized by treatment with salivary IgA for 1 h (FIG. 30C). Neutralization of the virus by treatment with serum IgA was evident only after prolonged incubation (24 h; not shown), and there was little or no neutralization at the 1 h time point [121]. IgG was ineffective at both time points studies. Thus, the neutralizing activity follows the pattern of the catalytic activity: salivary IgA>serum IgA>>serum IgG.

Specificity was evident from lack of hydrolysis of albumin, soluble epidermal growth factor receptor, FVIII C2 domain and Tat. The catalytic reactions were inhibited completely by an electrophilic analog of gp120 residues 421-433 (E-421-433) [120,121]. IgMs and IgAs formed covalent adducts with E-421-433 stable to boiling and SDS (FIG. 30B). Similarly, viral neutralization was inhibited by E-421-433 [121]. By N-terminal aa sequencing, the major cleavage site was the 432-433 bond in the SAg site [120, 121]. Salivary sIgA also hydrolyzed the V83-E84 and Y321-T322 bonds. These observations indicate a nucleophilic catalytic mechanism in which noncovalent 421-433 recognition permits selective gp120 hydrolysis. Hydrolysis of multiple bonds in polypeptide Ags by Igs, some distant from the binding epitope, has been previously reported [122,123]. The observations are consistent with a split-site model involving distinct subsites responsible for noncovalent binding and catalysis [124]. The catalytic subsite fails to make stable contacts with the Ag in the noncovalent immune complex. As the transition state develops, different peptide bonds become positioned in register with the catalytic site. When the Ab recognizes a conformational epitope, the alternate cleavage sites must be spatial neighbors, but they can be distant in the linear sequence, producing a complex fragmentation pattern.

Neutralizing Igs from Long-Term Survivors of HIV Infection

Adaptive synthesis of specific Igs to microbial antigens usually entails sequence diversification at the CDRs of the B cell receptor (BCR), guided by selection pressures enabling proliferation of B cells with the highest affinity BCRs. Adaptive improvement of Igs to superantigenic epitopes is thought to be proscribed by B cell down-regulatory signals generated upon superantigen interactions at BCR FRs [125].

Figure 31:
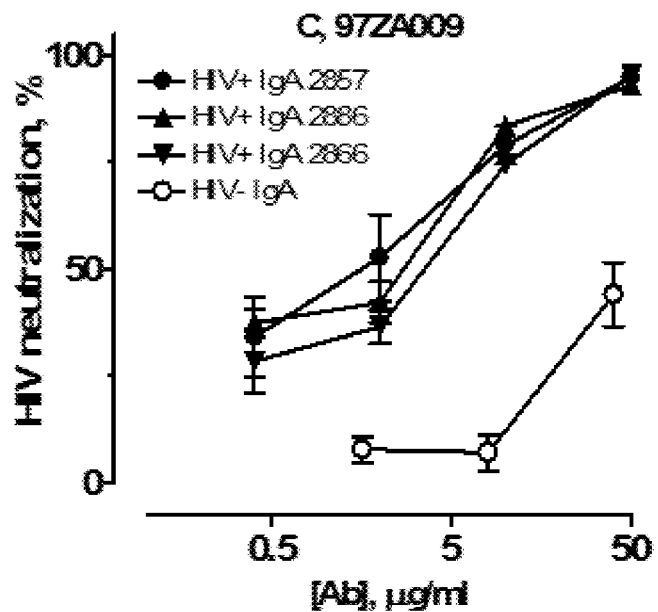
FIG. 31 illustrates the heterologous HIV strain neutralizing activity of serum IgA from presumptive clade B infected $S_{18}$ subjects. Top, Neutralization of clade C strain ZA009 (R5 coreceptor) by IgA from 3 $S_{18}$ subjects. IgA incubated 1 h with HIV before assaying infectivity using human PBMCs. Means of 4 replicates. Bottom, Consensus V3 region 306-325 and 421-433 region sequences compared to corresponding strain ZA009 sequences. Dot, identity; dash, gap.
Figure 32:
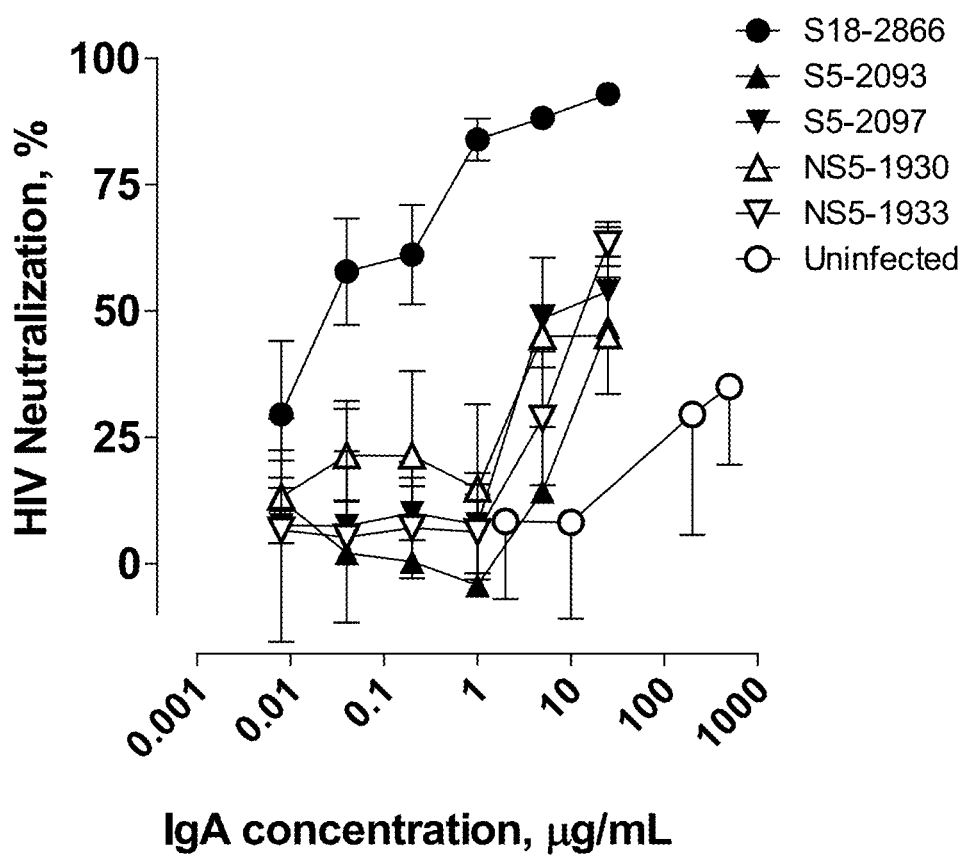
FIG. 32 illustrates the superior neutralizing potency of serum IgA from a $S_{18}$ subject. Neutralization of clade C strain ZA009 (R5 coreceptor) by IgA isolated from sera of an uninfected subjects, an $S_{18}$ subject (i.d. 2866), two $S_5$ subjects (i.d. 2093 and 2097) and two $NS_5$ subjects (i.d. 1930 and 1933). HIV (100 $TCID_{50}$) was incubated with IgA for 1 h, then allowed to infect phytohemagglutinin-stimulated human PBMCs. Values are expressed as percent reduction of p24 concentrations in test cultures compared to cultures that received diluent instead of IgA (means±s.d. of 4 replicates).

IgA preparations from the blood of three subjects who have survived for 18-20 years following infection by presumptive clade B HIV strains despite little or no antiretroviral therapy (designated survivor "$S_{18}$" subjects; CD4 cell counts 178-426/l) were studied. Serum IgA preparations from the $S_{18}$ subjects displayed readily detectable gp120 hydrolyzing activity. Identical fragmentation profiles were observed by treating biotinylated gp120 with IgA from HIV infected and non-infected humans. Diverse clade B and heterologous clade C strains were neutralized with exceptional potency by the $S_{18}$ IgAs (FIG. 31 and Table 4; 1 h incubation with virus; n=1 R5-dependent strains). The immunodominant V3 306-325 epitope is highly variable in these strains and the 421-433 epitope is mostly conserved (see example sequences, FIG. 31). In comparison, the reference MAb commonly cited as a broad neutralizing Ig, clone b12, did not neutralize many strains, and when neutralization was evident, the potency was substantially lower (Table 4). The neutralizing potency of $S_{18}$ IgAs was about 3 orders of magnitude superior to IgAs from uninfected subjects and IgAs obtained 1-5 years after seroconversion from subjects who succumbed to AIDS (designated non-survivors "$NS_5$" subjects; CD4$^+$ T cell counts <200/μl; n=10) or survived without development of AIDS ($S_5$ subjects, CD4$^+$ T cell counts >200/μl; n=10) (FIG. 32). gp120 binding by IgAs from $S_{18}$, $NS_5$ and $S_5$ subjects was comparable, indicating similar conventional antibody activity. The restricted presence of potently neutralizing IgAs in very late infection suggests an unconventional adaptive response. In addition to binding to the immunodominant V3 epitope, increased binding of a non-hydrolyzable electrophilic analog of gp120 residues 421-433 by $S_{18}$ IgAs was evident. These observations suggest that survivors with prolonged HIV infection mount a late adaptive IgA response to gp120 with properties that can slow progression to AIDS.

TABLE 4

Heterologous clade C HIV and diverse clade B strain neutralization by IgAs from 3 $S_{18}$ subjects. Clade C strains: 97ZA009, 98TZ013, 98TZ017, Du123, Du156, Du172, Du422. Clade B strains: ADA, PAVO and QH0692. All CCR5-dependent. PBMC hosts, p24 assays. Dose-dependent HIV neutralization was evident in all assays.

|  | Number of strains neutralized/Number of strains tested ($IC_{50}$ range; mean ± S.D, μg/ml) | |
| --- | --- | --- |
|  | clade B | clade C |
| IgA 2857 | 3/3 (0.08-0.20; 0.12 ± 0.07) | 6/6 (0.01-2.70; 0.9 ± 1.3) |
| IgA 2866 | 3/3 (0.002-1.000; 0.37 ± 0.55) | 7/7 (0.008-1.960; 0.5 ± 1.0) |
| IgA 2886 | 3/3 (0.20-0.80; 0.53 ± 0.33) | 7/7 (0.10-10.70; 2.4 ± 3.8) |
| IgG B12 | 3/4 (0.90-10.00; 3.96 ± 5.22) | 3/8 (4.10-10.50; 6.1 ± 3.5) |

HIV Neutralization by Specific IgAs to 416-433 Epitope

The structure of E-416-433 used for covalent affinity chromatography is shown in FIG. 33A. E denotes the phosphonate group located at Lys residue side chains. E-416-433 was conjugated to BSA or γ-aminobutyl-agarose using the crosslinker N-(γ-maleimidobutyryloxy)succinimide ester. The IgA was allowed to bind BSA-E-416-433 (black) or control albumin (gray), the immune complexes were captured on anti-albumin antibody conjugated to agarose column, and neutralization of subtype C ZA009 strain by the unbound IgA fraction was measured using PBMC hosts. IgA ($LTS_{19-21}$ donor 2866) immunoadsorbed with BSA-E-416-433 demonstrated reduced neutralizing activity (FIG. 33B). Confirmation that the epitope-reactive IgAs were removed was by ELISA using immobilized BSA-E-416-433 ($A_{490}$ values for IgA binding activity without immunoadsorption were 0.88±0.01, and after immunoadsorption with BSA-E-416-433 or albumin alone, respectively, 0.17±0.01 and 0.92±0.01. Pooled IgA ($LTS_{19-21}$ donors 2857, 2866 and 2886) was fractionated on E-416-433 conjugated to agarose, unbound IgA was removed, and the non-covalently bound fraction was recovered by elution with a pH 2.7 buffer. Covalently bound IgA was recovered by treatment of the gel with pyridine 2-aldoxime methiodide and elution with the pH 2.7 buffer. HIV neutralization was measured as in new FIG. 33A. The IgA fractions demonstrated improved neutralizing activity (FIG. 33C). The epitope-specific IgAs prepared by affinity chromatography also displayed enriched BSA-E-416-433 binding activity. The association of 416-433 epitope mutations R419K, V430AR423K, and R432Q in various HIV strains with reduced IgA neutralizing potency was examined (FIG. 33D). IC50 values of the three $LTS_{19-21}$ IgA preparations for strains without and with mutations at individual amino acid positions were compared using the 2-tailed Student's t-test. Mutations were identified by comparing the following 17 HIV strains with consensus subtype C epitope sequence as subtype C strains were neutralized most potently by the IgAs; 98Du123, 99Du156, 98Du172, 98Du422, 98TZ017, 97ZA009, 92BR021, SF162, 96PAVO, 94QHO692, 92RW008, 92RW024, 93UG082, 94UG114, 92UG035, 90CM235, 92TH005.

Ig L Chain Subunits Directed to Gp120 Residues 421-433

Previously, increased polyclonal Igs that bind the 421-436 region were observed in lupus sera [126]. It was reported that increased catalytic Igs in autoimmune diseases. Several reports have noted that HIV infection is infrequent in lupus patients [127-131]. The mechanism of increased Igs to the 421-433 region in lupus is not clear. One possibility is Ig synthesis driven by a homologous antigen. By searching the sequence databases, nucleotide sequence homology between the 421-433 region and a human endogenous retroviral sequence (HERV) was found [132]. HERV expression is increased in lupus [133].

To isolate nucleophilic antibody L chain subunits that recognize gp120 residues 421-433, a phage-displayed light chain library from lupus patients was prepared. The library was fractionated by the following two methods: (a) a two step procedure entailing covalent selection using an electrophilic hapten as described in [134] followed by non-covalent selection using the peptide corresponding to gp120 residues 421-436; and (b) a one step, affinity-driven covalent selection using the electrophilic analog of gp120 421-433 containing the phosphonate group at the C-terminus (E-421-433; FIG. 34A). Procedures for preparation of the phage light chain library and E-421-433 were described previously [134, 135]. Selection procedures were essentially as in [134] and [132]. For example, E-421-433 complexed phages were captured with streptavidin-agarose, the noncovalently bound phages were removed by acid washing (pH 2.7), and covalently bound phages were eluted by 2-mercaptoethanol reduction of the S—S group in the E-421-433 linker. Covalently selected light chains were expressed in soluble form and purified by metal affinity chromatography.

Thirty one L chains selected using the 421-436 peptide and 22 L chains selected using E-421-433 were studied for gp120 hydrolyzing activity. The proteolysis assay was conducted using biotinylated gp120 (Bt-gp120; prepared from recombinant gp120 of MN strain; baculovirus expression system) as substrate followed by SDS-electrophoresis and densitometry of streptavidin-peroxidase stained blots. The group of L chains selected using E-421-433 displayed significantly greater proteolytic activity than the 421-436 selected L chains (FIG. 34B; mean±SE values, respectively, 1098±157 vs 369±56 AVU; P<0.0001, unpaired two-tailed t-test). This result indicates that, although both groups contain 421-433-directed nucleophilic antibody fragments, the E-421-433 selection can afford more efficient enrichment of the L chains compared to the two-step selection.

Two L chains each from the 421-436 selected group (clones SK18 and SK45) and the E-421-433 selected group (clones SK2C2 and SK2F5) were assessed for their ability to neutralize a clade C HIV primary isolate (97ZA009) using peripheral blood mononuclear cells (PBMCs) as hosts. All four light chains neutralized this HIV isolate ($IC_{50}/IC_{80}$ values: SK18, 0.6/2.1; SK45, 0.6/3.9; SK2C2, <0.01/0.13; SK2F5, <0.01/0.07 µg/mL). The cDNAs encoding the 421-436-selected L chains SK18 and SK45 and E-421-433 selected L chain SKL6 were sequenced. Their deduced $V_L$ domain amino acid sequences are shown in FIGS. 35A-35C.

IgV Fragments Isolated by Covalent Phage Selection with Gp120 and E-Gp120

Figure 36A:
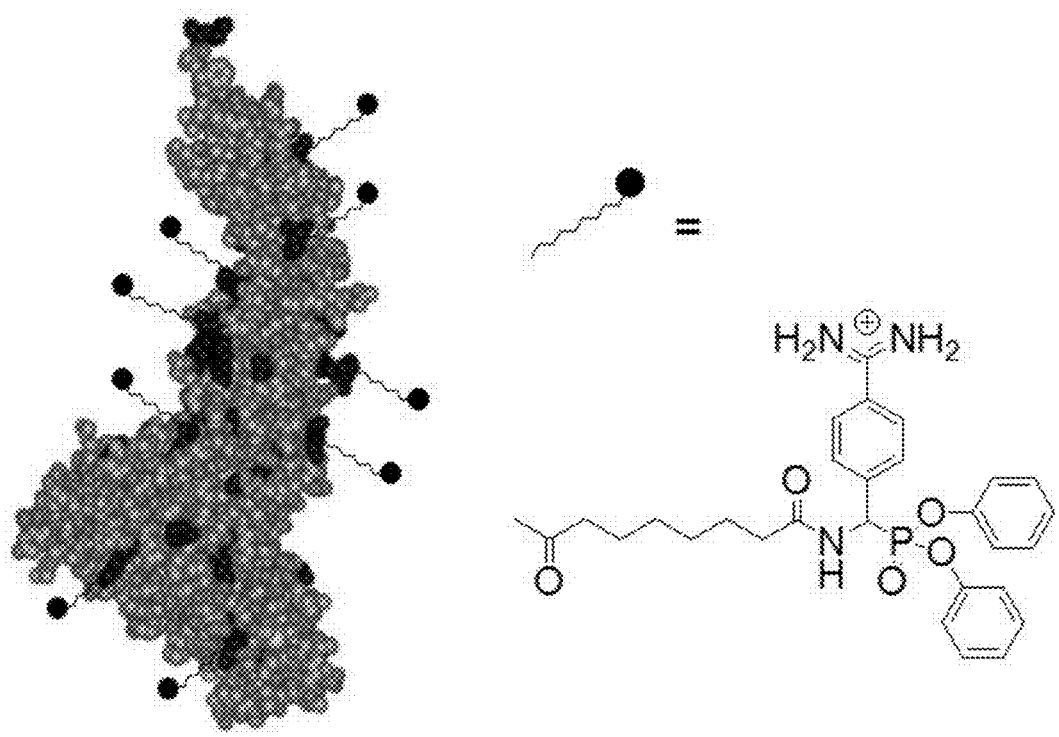
FIGS. 36A-36B illustrate isolation of nucleophilic antibody IgVs by covalent phage selection with E-gp120.

To isolate nucleophilic IgV fragments, the phage-displayed IgV library derived from lupus patients was fractionated for binding to gp120 or E-gp120 (FIG. 36A). Procedures for preparation of the phage IgV library and E-gp120 were described previously [134,136]. As described in EXAMPLE 1, a majority of the clones in this library are scFv constructs mimicking the physiological structures of Ig combining sites. The remaining clones are IgVs with unnatural structures, including $IgV_{L2}$-t and $IgV_L$-t' structures. IgV-displaying phages were packaged from the library and subjected to noncovalent selection by affinity chromatography on recombinant gp120 (immobilized on Biorad Affigel-10). Phages from the acid eluate were then subjected to covalent selection with biotinylated E-gp120. E-gp120 complexed phages were captured with immobilized anti-biotin IgG, and following extensive washing with a neutral buffer, bound phages were allowed to elute using the pH 2.7 buffer. The gp120 selected and E-gp120 selected IgVs were expressed in soluble form and purified by metal affinity chromatography.

Figure 36B:
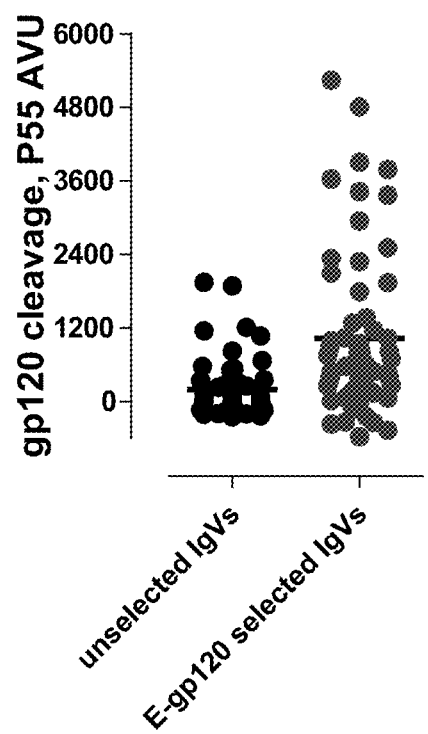

Sixty two IgVs obtained by E-gp120 selection were assayed for gp120 hydrolysis activity along with a random collection of 61 IgVs from the source library obtained without selection. The proteolysis assay was conducted using biotinylated gp120 as in the preceding section. The E-gp120 selected group displayed significantly greater proteolytic activity than the unselected group (FIG. 36B; mean±SE intensity of 55 kD product band generated by the E-gp120 selected group vs unselected group, 1027±167 vs 196±58 AVU; P<0.0001, unpaired two-tailed t-test). Examples of gp120 hydrolyzing IgVs obtained by E-gp120 selection (clones GL2 and GL59) are shown in FIG. 37A.

About 50% of the IgV clones selected using gp120 and 100% of the clones selected using E-gp120 neutralized the clade C strain ZA009 using PBMC hosts (Table 5). The neutralizing potency of the E-gp120 selected clones was markedly superior to the gp120 selected clones, suggesting the functional advantage gained due to greater nucleophilicity (Table 5). The neutralizing potency of example IgV clones GL2, GL59 and JL427 are shown in FIG. 37B. scFv 610 in this figure is a control non-neutralizing clone, and IgG b12 is a leading monoclonal IgG commonly cited in the literature as a broadly neutralizing IgG. Neutralization by the IgV clones was inhibited by treatment with E-421-433 but not the irrelevant E-VIP (FIG. 37C).

TABLE 5

HIV neutralization (clade C, R5, ZA009) by lupus scFv fragments selected using gp120 or E-gp120. The characteristics of the lupus library are as in ref [32]. The scFv were purified by Ni-NTA chromatography and tested for neutralization using ZA009 (clade C, R5) [35].

| Selecting Antigen | # of clones, tested | # of clones, neutralized | Potency ($EC_{50}$, µg/ml) 0.25-2.5 | 0.025-0.25 | 0.0025-0.025 |
|---|---|---|---|---|---|
| gp120 | 52 | 25 | 17 | 8 | 0 |
| E-gp120 | 14 | 14 | 0 | 6 | 8 |

By nucleotide sequencing, the E-gp120 selected IgVs GL2 and GL59 were identified as scFv constructs that mimic the structure of physiological Ig combining sites. The gp120 selected IgV clones JL606, JL678 and JL427 were also scFvs. As in the E-Aβ selection studies (Example 1), certain selected IgV clones contained aberrant structures. These are the heterodimeric $IgV_{L2}$ clone GL1, the single domain $IgV_H$-t clone JL683 without a VL domain partner but with the expected tag at the C terminus, and the single domain $IgV_L$-t' clone JL651 containing a VH domain with a large internal deletion. Tag t refers to the 27 residue c-myc/his6 sequence at the C terminus, and the designation t' is used to denote the unexpected VH peptide with tag t at the C terminus in $IgV_L$-t' JL651. Schematic representations of the structures and amino acid sequences of these clones are in FIGS. 38A-38D. The HIV neutralizing potency of these clones is shown in Table 6.

TABLE 6

HIV neutralization potency of E-gp120-selected and gp120-selected IgVs. HIV, 97ZA009; host, PBMC. $IC_{50}$ values are in ng/mL units, and mean ± SEM are shown for clones tested in multiple independent assays (numbers in parenthesis represents the number of assays).

| | E-gp120 selected | | |
|---|---|---|---|
| | scFv GL2 | scFv GL59 | $IgV_{L2}$-t GL1 |
| $IC_{50}$, ng/mL | 8.8 ± 5.3 (3) | 2.5 ± 0.9 (6) | 8.1 ± 5.8 (2) |

| | gp120 selected | | | | |
|---|---|---|---|---|---|
| $IgV_{H-t}$ JL683 | $IgV_{L-t'}$ JL651 | scFv JL606 | scFv JL678 | scFv JL427 |
| 3.7 | 29.3 | 82.5 | 141.0 | 300 ± 350 (24) | scFv clones GL2 and JL427 neutralized diverse R5-dependent HIV strains (clades A, B, C; Table 7). Another intriguing finding is that scFv clone JL427 neutralized primary HIV strains in the PBMC assay strains but not the corresponding pseudovirions assayed in reporter cell lines. This implies that the 421-433 region may be expressed on native virions and pseudovirions in Ig-recognizable and non-recognizable conformations, respectively. Another Ig that neutralizes primary HIV isolates but not pseudovirions is reported [138]. Importantly, a recent study indicates that neutralization of primary HIV strains by Igs from certain infected subjects correlates with lack of progression whereas neutralization of pseudovirions does not [139]. For these reasons, it is appropriate to rely on infection assays using primary HIV isolates. In these assays, the 421-433 recognizing Igs surpass the potency and breadth of neutralization of other known Igs.

TABLE 7

Cross-clade HIV neutralization by lupus scFvs GL2 and JL427.
PBMC assays. HIV strains (clade/coreceptor strain names):
A/R5 92RW008; A/X4 92USNG17; B/R5 SF162, 92BR014, BAL, PVO,
TRO, ADA; B/X4 92HT599, Tybe; B/R5X4 BZ167, 92BR014; C/R5
98BR004, 97ZA009, 98TZ013, 98TZ017, Du123, Du422, Du172;
D/R5 92UG266; D/X4 92UG001, 92UG266, 92UG046. Dose dependent
HIV neutralization was evident in all cases.

| HIV clade | Number of strains neutralized/Number of strains tested (IC50 range, mean ± S.D.; μg/ml) | |
|---|---|---|
| | scFv GL2 | scFv JL427 |
| A | 2/2 (0.8-4.2; 2.5 ± 2.4) | 1/1 (0.2; N/A) |
| B | 5/6 (0.007-3.7; 1.5 ± 1.9) | 6/8 (0.03-5.1; 1.3 ± 2.0) |
| C | 5/5 (0.015-2.7; 0.9 ± 1.3) | 6/6 (0.007-4.8; 0.9 ± 1.9) |
| D | 0/3 | 0/4 |

IgV FR/CDR Swapping

Antigen-specific Igs are usually synthesized adaptively by mutations occurring in the CDRs. In comparison, the superantigenic site of gp120 is thought to be recognized by Igs via contacts at conserved residues located mainly in VH3 domain FR1 and FR3 with additional contributions provided by CDR 1 and CDR2 [118,119]. Conventional Igs that bind the gp120 superantigenic site predominantly utilize VH3 family genes [43], suggesting that conserved VH3 family gene elements preferentially recognize the superantigenic site by noncovalent means. Replacement of the individual FRs and CDRs in a gp120 binding VH3 family Fab by the corresponding FRs and CDRs of a non-VH3 family, non-gp120 binding Fab resulted in loss of the gp120 binding activity of the former Fab [118].

The present invention discloses FR and CDR swapping as a novel means to improve recognition of the gp120 superantigenic site by Igs. The neutralizing scFv GL2 contains a VH4 family VH domain and the neutralizing scFv JL427 contains a VH3 family VH domain. FR1, FR3, CDR1 or CDR2 of the scFv GL2 VH domain were replaced individually by the corresponding regions of the VH3 family scFv JL427. This was done by a PCR-based substitution method using mutagenic primers coding for the aforementioned scFv JL427 regions and scFv GL2 in pHEN2 plasmid as template. PCR products were treated with T4 polynucleotide kinase, DpnI to remove the methylated template DNA, and the purified mutant DNA was circularized by ligation. The DNA was sequenced to confirm the presence of the desired mutations, and mutant scFv mutants were expressed and purified by metal affinity chromatography as described [134]. FIG. 39 shows a schematic representation of the mutants and their sequences. The mutants are designated GL2-FR1m, GL2-FR3m, GL2-CDR1m and GL2-CDR2m, wherein GL2 denotes the scFv GL2 containing FR1, FR3, CDR1 and CDR3 from scFv JL427.

ELISAs using plates coated with E-gp120 or KLH conjugated to E-416-433 were employed to determine recognition of the gp120 superantigenic site. Preparation of E-gp120 and study of its binding by the scFv constructs was as in [136]. Preparation of E-416-433 was as in [140]. This peptide analog displays improved reactivity to Igs that recognize the gp120 superantigenic site compared to E-421-433, a finding consistent with the report that inclusion of the N terminal 416-420 residues induces a conformational change in the 421-433 region [141]. E-416-433 contains phosphonates at Lys422 and Lys432. Its identity was verified by electrospray ionization-mass spectrometry. Conjugation of the peptide analog to KLH was as in [142]. The nonhydrolyzable E-antigen probes were employed (instead of unmodified gp120 and unmodified 416-433 peptide) to preclude possible hydrolysis by scFv GL2, which has the ability to catalyze gp120 degradation.

Figure 40A:
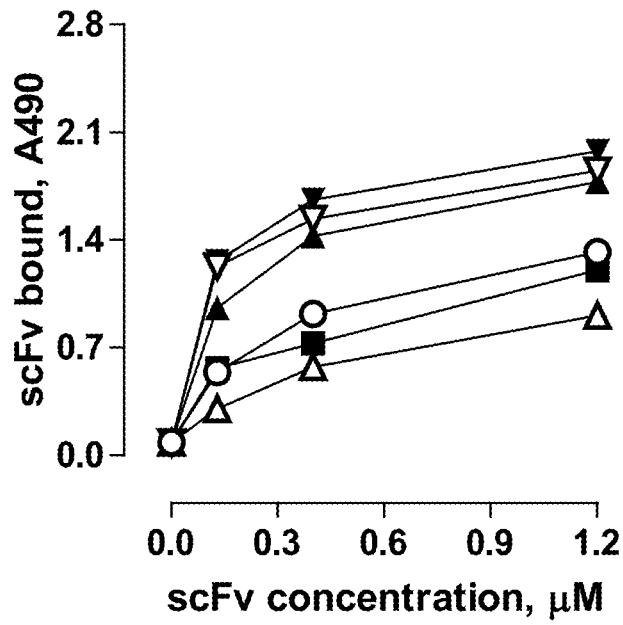
FIG. 40 illustrates E-416-433 and E-gp120 binding by scFv GL2 mutants. Shown are ELISA data with plates coated with E-416-433 (KLH conjugate; 70 ng peptide equiv/well) or E-gp120 (100 ng/well). Bound scFv was detected with anti-c-myc antibodies and peroxidase-conjugated anti-mouse IgG (Fc specific).
Figure 40B:
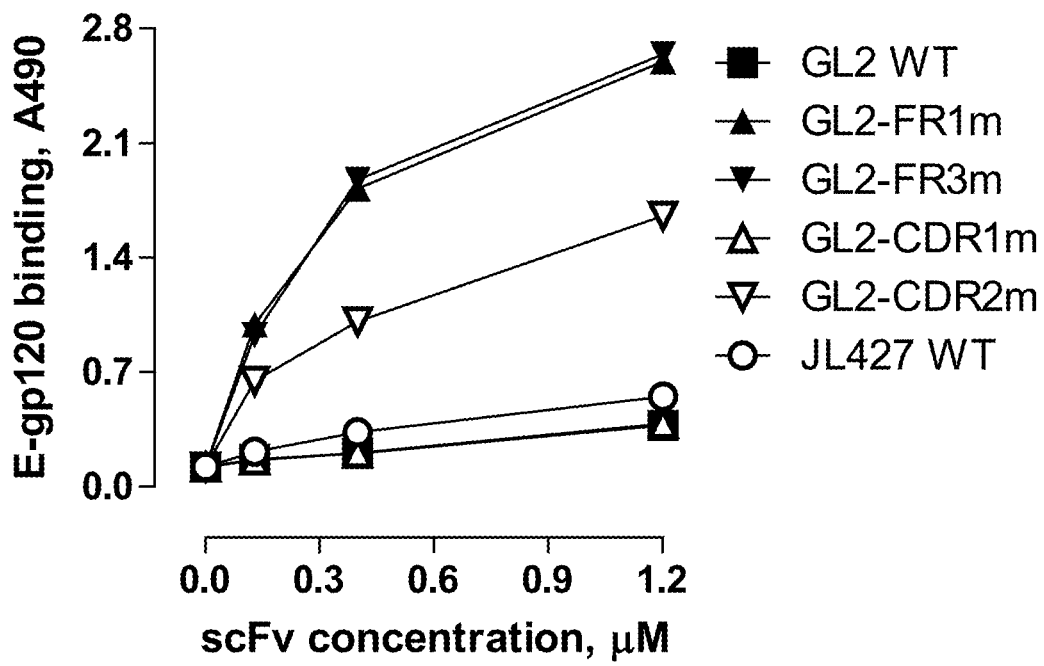

The mutant scFv constructs GL2-FR1m, GL2-FR3m displayed markedly increased binding to E-gp120 and E-416-433 compared to wildtype (unmutated) scFv GL2 (FIG. 40). These mutants also displayed increased binding to the two antigenic probes compared to the scFv JL427. scFv JL427 contains the full-length complement of gp120 superantigen binding expressed by a full-length VH3 domain, whereas the mutants contain only small fragments derived from the VH3 domain of JL427. It is contemplated that the scFv GL2 VL domain provides an important contribution in recognition of the superantigenic epitope of gp120. The obvious alternative route to improving gp120 superantigen site binding, therefore, is to screen and select for optimally paired VL and VH domains from diverse combinatorial libraries of the two domains.

Example 5

Figure 41A:
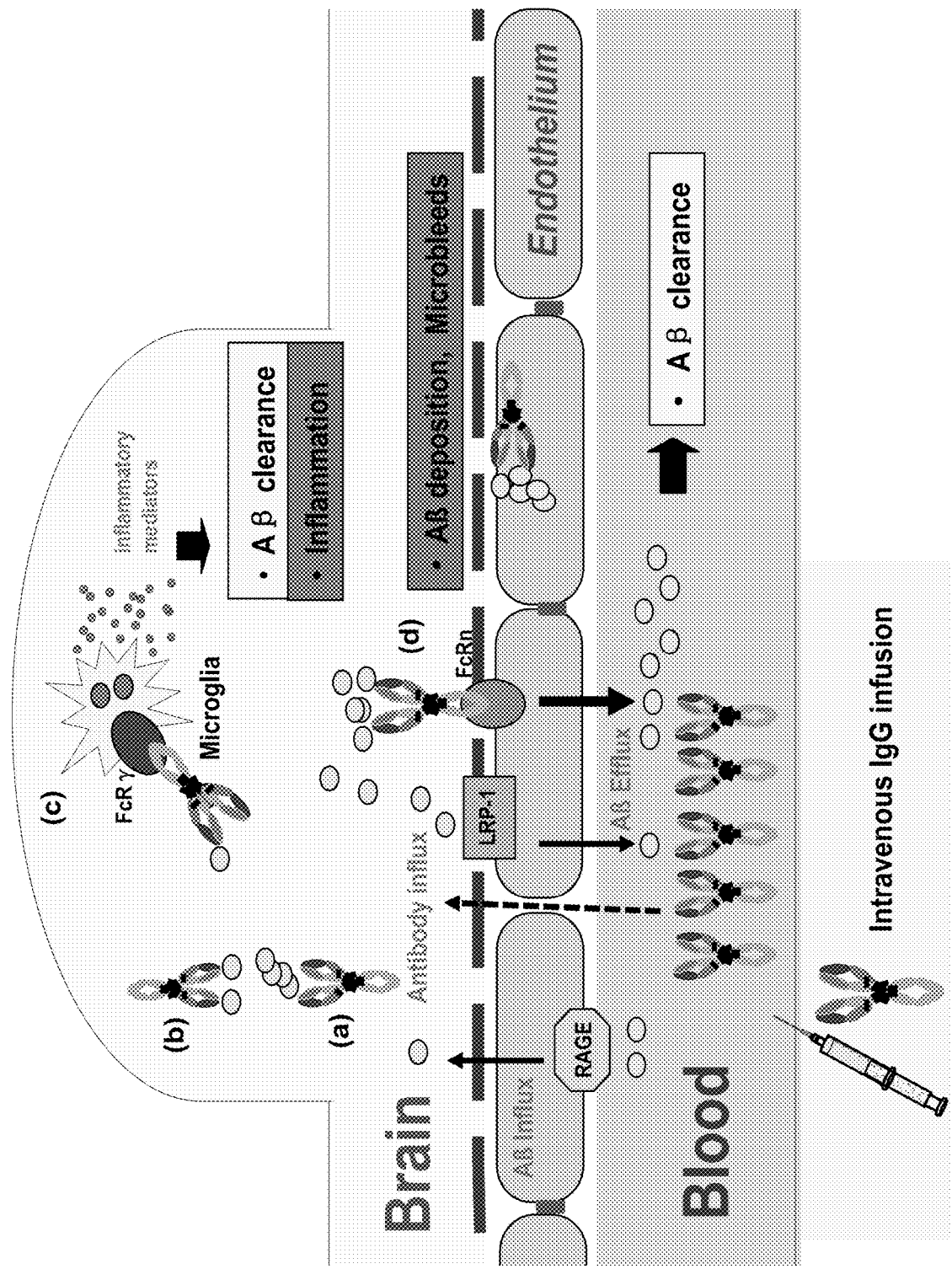
FIG. 41A-41C illustrate the feasibility of passive immunotherapy of Alzheimer disease with Aβ binding and Aβ hydrolyzing Igs.

Passive Immunotherapy of Alzheimer Disease with Aβ Binding and Aβ Hydrolyzing Igs Aβ Binding IgG Reversibly binding IgG injected into peripheral blood can enter the brain in small amounts and help clear Aβ by mechanisms described herein (FIG. 41A). Following binding of IgG to Aβ monomers (a) or aggregates (b), the immune complexes are ingested by an Fcγ receptor-dependent uptake process into microglia (c). The IgG bound by Fcn receptors at the blood-brain barrier may help clear Aβ from the brain and efflux to the periphery via transcytosis (d). Microglial ingestion of the immune complexes is accompanied by release of inflammatory mediators, which could exacerbate the already inflamed state of the AD brain. In mouse AD models, clearance of amyloid plaques from the brain parenchyma induced by Aβ-binding IgGs can be accompanied by Aβ deposition in the blood vessels and microhemorrhages.

Aβ Hydrolyzing IgM

Figure 41B:
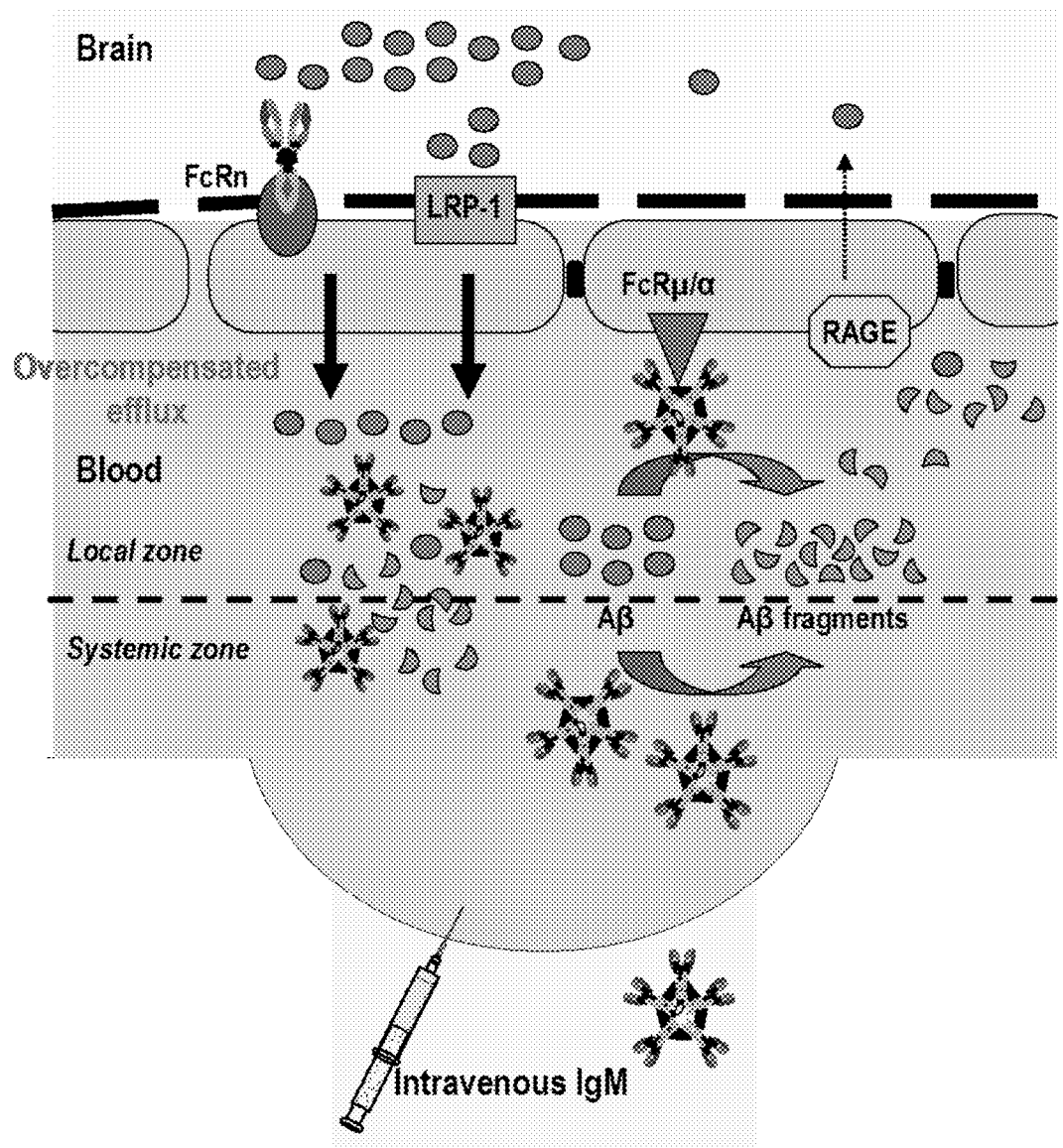

Hydrolysis of Aβ by peripheral IgM increases the Aβ brain-periphery concentration difference and thereby enhances Aβ efflux from the brain (FIG. 41B). Catalytic IgM bound to FcRμ/α on the luminal (blood) side of the blood-brain-barrier may enhance the local concentration difference at the blood-brain-barrier, thus inducing an overcompensatory depletion effect and facilitating sustained removal of brain Aβ into the periphery.

Aβ Hydrolyzing IgGL

Figure 41C:
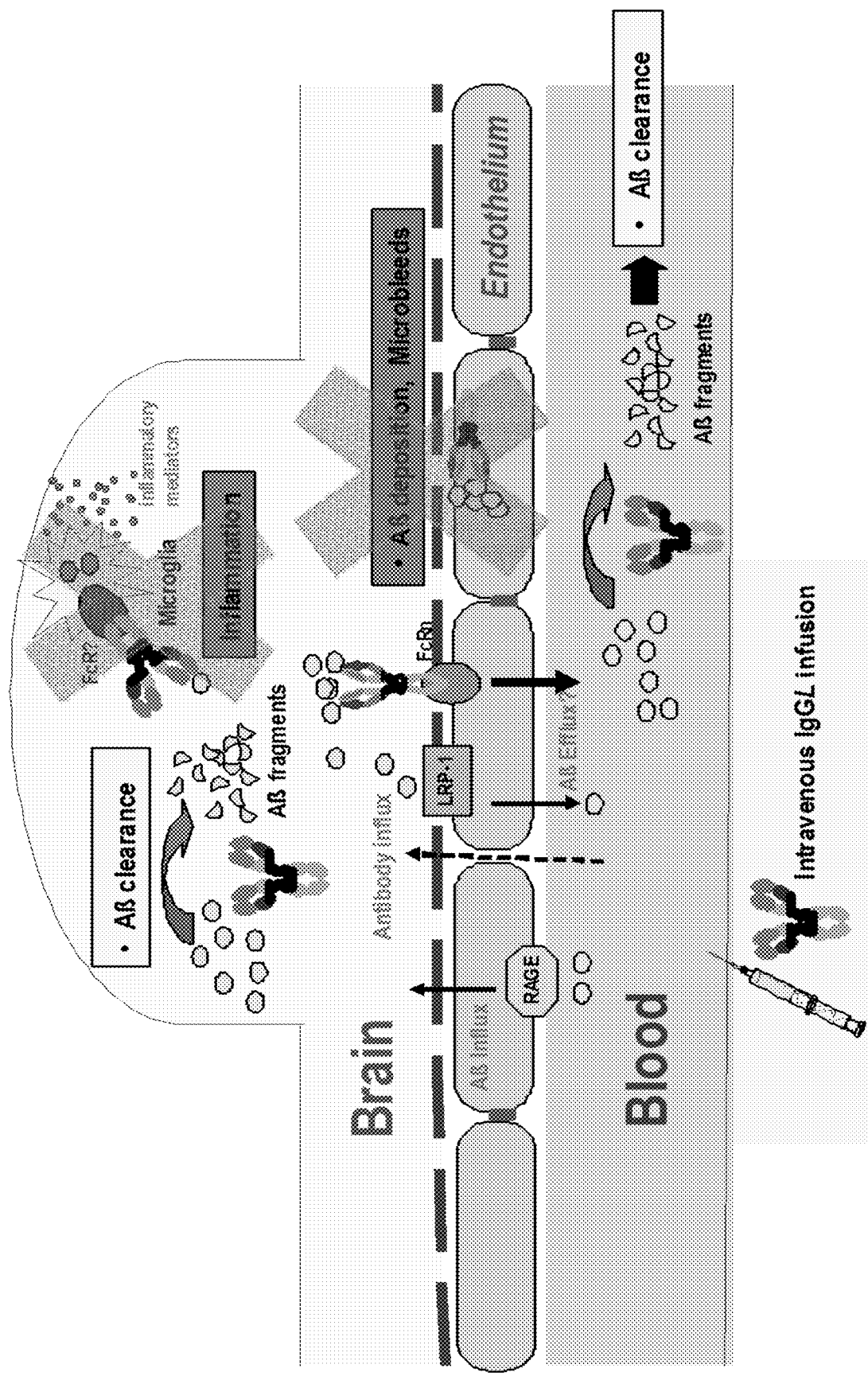

Sufficient amounts of the IgGL catalysts administered into peripheral blood can enter the brain and hydrolyze the brain Aβ deposits and soluble oligomers, reducing the brain Aβ burden (FIG. 41C). Like IgG, IgGL contains the Fc domain and may mediate an FcRn-mediated Aβ transcytosis. LRP1/RAGE transporters are known to help maintain the equilibrium between brain and peripheral Aβ.

Brain Aβ Depletion by $IgV_{L2}$-t 2E6 as Potential Treatment

Catalytic $IgV_{L2}$-t 2E6 (1 μg) was injected into the cortex of the right hemispheres of 5×FAD APP/PS1 mice (n=7). Seven days later, brain sections were stained with anti-Aβ antibody 6E10 and 4G8 and Aβ plaques were quantified relative to the total area examined (FIG. 42A). However, noncatalytic $IgV_{L2}$-t MMF6 fails to reduce Aβ plaques in mice (n=4) (FIG. 42B). Photomicrographs of right cortex sections following injection with PBS (FIG. 42C top) or catalytic IgV$_{L2}$-t 2E6 (FIG. 42C bottom) and non-injected left cortex PBS section (FIG. 42C top) and control (FIG. 42C bottom) show plaques stained with the anti-Aβ antibody. PBS injection (n=4) was without significant effect compared to the non-injected left cortex. The needle tracks are visible in the injected right cortex. IgV$_{L2}$-t 2E6 clearly promotes plaque clearance as indicated by lack of plaques near the injection site.

The following references are cited herein.
1. Sun et al. J Immunol 1994, 153:5121-5126.
2. Paul S. Appl Biochem Biotechnol 1994, 47:241-253.
3. Li et al. MoI Immunol 1996, 33:593-600.
4. Li L et al. J Immunol 1995, 154:3328-3332.
5. Kalaga et al. J Immunol 1995, 155:2695-2702.
6. Shuster et al. Science 1992, 256:665-667.
7. Matsuura et al. Biochem Biophys Res Commiin 1998, 243:719-721.
8. Paul et al. J Biol Chem 1995, 270: 15257-15261.
9. Planque et al. J Biol Chem 2004, 279:14024-14032.
10. Mitsuda et al. MoI Biotechnol 2007, 36: 1 13-122.
11. Pantoliano et al. Biochemistry 1991, 30:10117-10125.
12. Masat et al. Proc Natl Acad Sd USA 1994, 91:893-896.
13. Sun et al. J Biol Chem 1994, 269:734-738.
14. Marks et al. J MoI Biol 1991, 222:581-597.
15. Kubetzko et al. J Biol Chem 2006, 281:35186-35201.
16. Krinner et al. Protein Eng Des SeI 2006, 19:461-470.
17. Yang et al. Protein Eng 2003, 16:761-770.
18. McLean et al. MoI Immunol 2000, 37:837-845.
19. DeMattos et al. Proc Natl Acad Sci USA 2001, 98:8850-8855.
20. Dodel et al. J Neurol Neurosurg Psychiatry 2004, 75: 1472-1474.
21. Alzheimer A: AHg. Z. Psychiat. 1907, 64: 146-148.
22. Glenner et al. Biochem Biophys Res Commun 1984, 122: 1131-1135.
23. Kang J et al. Nature 1987, 325:733-736.
24. Haass et al. Nature 1992, 359:322-325.
25. Seubert et al. Nature 1992, 359:325-327.
26. Games et al. Nature 1995, 373:523-527.
27. Morgan et al. Nature 2000, 408:982-985.
28. Citron et al. Nature 1992, 360:672-674.
29. Ohno et al. Neuron 2004, 41:27-33.
30. Solomon et al. Proc Natl Acad Sci USA 1997, 94:4109-41 12.
31. Chromy et al. Biochemistry 2003, 42: 12749-12760.
32. Kido et al. J Biol Chem 1993, 268:13406-13413.
33. Capon D J and Ward R H. Annu Rev Immunol 1991, 9:649-678.
34. Gelderblom et al. Lancet 1985, 2:1016-1017.
35. Brenneman et al. Nature 1988, 335:639-642.
36. Muller et al. Eur J Pharmacol 1992, 226:209-214.
37. Hober et al. FEMS Immunol Med Microbiol 1995, 10:83-91.
38. Laurent-Crawford et al. Res Virol 1995, 146:5-17.
39. Stoiber et al. Aids 1995, 9: 19-26.
40. Thali et al. J Virol 1991, 65:6188-6193.
41. Thali et al. J Virol 1992, 66:5635-5641.
42. Berberian et al. Science 1993, 261:1588-1591.
43. Karray S and Zouali M. Proc Natl Acad Sci USA 1997, 94:1356-1360.
44. Goodglick L et al. J Immunol 1995, 155:5151-5159.
45. Kissane J M: Staphylococcal Infections. In Pathology of Infectious Diseases. Edited by Connor D H, Chandler F W, Schwartz H J, Manz H J, Lack E E: Appleton and Lange; 1997:805-816, vol 1.
46. Lowy F D. N. Engl. J. Med. 1998, 339:520-532.
47. Mamo et al. FEMS Immunol Med Microbiol 1994, 10:47-53.
48. Lee J C. Curr Infect D 2001, 3:517-524.
49. Schaffer et al. Infect Iminun 2006, 74:2145-2153.
50. Centers for Disease Control and Prevention. Disease burden from viral hepatitis A, B and C in the United States. URL: www.cdc.gov/nicdod/diseases/hepatitis/heptab3.htm 1997.
51. Dusheiko G. NIH Consensus Development Conference on Management of Hepatitis C 1997, Program and Abstracts IV: 105-112.
52. Barth et al. Hepatology 2006, 44:527-535.
53. Zeisel et al. World J Gastroenterol 2007, 13:4824-4830.
54. Galun et al. J Hepatol 2007, 46:37-44.
55. Gao et al. J MoI Biol 1995, 253:658-664.
56. Planque et al. J Biol Chen 2003, 278:20436-20443.
57. Nishiyama et al. J Biol Chem 2004, 279:7877-7883.
58. Gololobov et al. MoI Immunol 1999, 36:1215-1222.
59. Dodel et al. J Neurol Neurosurg Psychiatry 2004, 75: 472-1474.
60. White A R and Hawke S H. J Neurochem 2003, 87:801-808.
61. Dodel et al. Ann Neurol 2002, 52:253-256.
62. Bard et al. Nat Med '2000, 6:916-919.
63. Taguchi V. J Biol Chem 2008, 283:4714-4722.
64. Paul S et al. J Biol Chem 2001, 276:28314-28320.
65. Liu et al. Biochemistry 2004, 43:9999-10007.
66. Maeda H et al. Biophys Chem 1978, 9:57-64.
67. Ely et al. J MoI Biol 1989, 210:601-615.
68. Oleksyszyn et al. Methods Enzymol 1994, 244:423-441.
69. Rooijakkers et al. Trends Microbiol 2005, 13:596-601.
70. Foster T J. Nat Rev Microbiol 2005, 3:948-958.
71. Lee et al. J Infect Dis 2004, 190:571-579.
72. Rooijakkers S H and van Strijp J A: MoI Immunol 2007, 44:23-32.
73. Shannon et al. Thromb Haemost 2004, 91:779-789.
74. Palma et al. J Biol Chem 2001, 276:31691-31697.
75. Shannon et al. Thromb Haemost 2005, 93:927-931.
76. Shannon et al. Scand J Immunol 2006, 63:184-190.
77. Lee et al. J Biol Chem 2004, 279:50710-50716.
78. Patti et al. Annu Rev Microbiol 1994, 48:585-617.
79. Silverman et al. J Immunol 1993, 151:5840-5855.
80. Goodyear et al. Proc Natl Acad Sci USA 2004, 101:11392-11397.
81. Goodyear et al. J Exp Med 2003, 197: 1 125-1 139.
82. Rivas et al. Citrr Opin Drug Discov Devel 2004, 7:223-227.
83. Klevens et al. Jama 2007, 298:1763-1771.
84. Weiss et al. J Antimicrob Chemother 2004, 53:480-486.
85. Mazmanian et al. Proc Natl Acad Sci USA 2000, 97:5510-5515.
86. Jonsson et al. Microbes Infect 2003, 5:775-7S0.
87. Walsh et al. Microbiology 2008, 154:550-558.
88. McDevitt et al. Eur J Biochem 1997, 247:416-424.
89. Walsh et al. J Biol Chem 2004, 279:50691-50699.
90. O'Brien et al. Cell Microbiol 2002, 4:759-770.
91. Wann et al. J Biol Chem 2000, 275: 13863-13871.
92. Labandeira—et al. Science 2007, 315:1130-1 133.
93. Ward et al. J Comp Pathol 1979, 89: 169-177.
94. Essmann et al. Cell Death Differ 2003, 10:1260-1272.
95. Jonas et al. Infect Immim 1994, 62:1304-1312.
96. Lee et al. J Clin Invest 2002, 110: 1461-1471.

97. Xie et al. J Exp Med 2006, 203:985-994.
98. Chavakis et al. Nat Med 2002, 8:687-693.
99. Scriba et al. Infect immun 2008, 76:2164-2168.
100. Paul et al. J Biol Chem 2004, 279:39611-39619.
101. Barth et al. Hepatology 2006, 44:527-535.
102. Cocquerel et al. J Virol 2003, 77:10677-10683.
103. Paul et al. J Biol Chem 2004, 279:39611-39619.
104. Paul et al. J Biol Chem 2003, 278:20429-20435.
105. 1. Collaborative Group on AIDS Incubation and HIV Survival including the CASCADE EU Concerted Action. Concerted Action on Seroconversion to AIDS and Death in Europe. Lancet 2000, 355: 1131-1137.
106. Cecilia et al. J Infect Dis 1999, 179: 1365-1374.
107. Townsley-Fuchs et al. J Clin Invest 1996, 98: 1794-1801.
108. Gaudieri et al. MoI Immunol 2005, 42:557-560.
109. Burton et al. Science 1994, 266:1024-1027.
110. Sanders et al. J Virol 2002, 76:7293-7305.
111. Scanlan et al. J Virol 2002, 76:7306-7321.
112. Ofek et al. J Virol 2004, 78: 10724-10737.
113. Binley et al. J Virol 2004, 78: 13232-13252.
114. Mascola et al. J Virol 1997, 71:7198-7206.
115. Veazey et al. Nat Med 2003, 9:343-346.
116. Goray et al. J Immunol 1993, 150:635-643.
117. Profy et al. J Immunol 1990, 144:4641-4647.
118. Neshat et al. lnt Immunol 2QQQ, 12:305-312.
119. Karray et al. J Immunol 1998, 161:6681-6688.
120. Paul et al. J Biol Chem 2004, 279:3961 1-39619.
121. Planque et al. AIDS Res Hum Retroviruses 2007, 23:1541-1554.
122. Hifumi E et al. J Immunol Methods 2002, 269:283-298.
123. Sun et al. J MoI Biol 1997, 271:374-385.
124. Paul S. MoI Biotechnol 1996, 5:197-207.
125. Juompan et al. Faseb J 1998, 12:1473-1480.
126. Bermas et al. AIDS Res Hum Retroviruses 1994, 10:1071-1077.
127. Chang et al. Am J Kidney Dis 1999, 33:441-449.
128. Daikh et al. Semin Arthritis Rheum 2001, 30:418-425.
129. Palacios R et al. Lupus 2002, 1 1: 60-63.
130. Sekigawa et al. Lupus 2000, 9: 155-156.
131 Wallace D J. Arthritis Rheum 1991, 34:372-373.
132. Nishiyama et al. MoI Immunol 2007, 44:2707-2718.
133. Urnovitz H B and Murphy W H et al. Clin Microbiol Rev 1996, 9:72-99.
134. Paul et al. J Biol Chem 2001, 276:28314-28320.
135. Taguchi et al. Bioorg Med Chem Lett 2002, 12:3167-3170.
136. Paul S. J Biol Chem 2003, 278:20429-20435.
137. Karle et al. Aids 2004, 18:329-331.
138. Brown v. J Virol 2007, 81:2087-2091.
139. Brown et al. AIDS Vaccine 2007. Seattle, Wash.; Aug. 20-23, 2007 Abstract OA05-08.
140. Nishiyama et al. J Biol Chem 2004, 279:7877-7883.
141. Reed J and Kinzel V et al. Proc Natl Acad Sci USA 1993, 90:6761-6765.
142. Karle et al. Vaccine 2003, 21 1213-1218.

What is claimed is:

1. A method for identifying an immunoglobulin (Ig) variable (V) domain of a light chain subunit (VL) or heavy chain subunit (VH) of an immunoglobulin having a specific, defined antigenic-directed activity comprising:

performing a screening of a library containing a plurality of IgV domains for the desired antigenic-directed activity, wherein said plurality of IgV domains comprise IgV domains which are a single IgV domain, wherein the antigen of said IgV is an amyloid protein or a superantigen other than gp120; said IgV comprises a nucleophilic site; said IgV catalyzes the hydrolysis of said amyloid protein or superantigen; and said IgV is obtained from an organism without prior immunization with said antigen.

2. A method for identifying an immunoglobulin (Ig) variable (V) domain of a light chain subunit (VL) or heavy chain subunit (VH) of an immunoglobulin having a specific, defined antigenic-directed activity comprising:

fractionating a library containing a plurality of IgV domains using antigen electrophilic analogs, wherein said plurality of IgV domains comprise IgV domains which are a single IgV domain, wherein the antigen of said IgV is an amyloid protein or a superantigen other than gp120; said IgV comprises a nucleophilic site; said IgV catalyzes the hydrolysis of said amyloid protein or superantigen; and said IgV is obtained from an organism without prior immunization with said antigen.

3. The method of claim 2, wherein said library of IgV domains is a phage-displayed IgV library.

4. The method of claim 1, wherein said library containing a plurality of IgV domains is obtained from lymphoid cells from an organism with lupus, Alzheimer's disease, a *Staphylococcus aureus* infection, an HIV infection or an HCV infection.

5. The method of claim 2, wherein said library of IgV domains is obtained from lymphoid cells from an organism with lupus, Alzheimer's disease, a *Staphylococcus aureus* infection, an HIV infection or an HCV infection.

6. The method of claim 1, wherein the catalytic activity hydrolyzes one or more peptide bonds in amyloid β peptide, a *Staphylococcus aureus* protein, or HCV E2.

7. The method of claim 2, wherein the catalytic activity hydrolyzes one or more peptide bonds in amyloid β peptide, a *Staphylococcus aureus* protein, or HCV E2.

8. A method for identifying an immunoglobulin (Ig) variable (V) domain of a light chain subunit (VL) or heavy chain subunit (VH) of an immunoglobulin having a specific, defined antigenic-directed activity comprising:

performing a screening of a library containing a plurality of IgV domains for the desired antigenic-directed activity, wherein said plurality of IgV domains comprise IgV domains which comprise a VL domain linked to a VL domain, wherein the antigen of said IgV is an amyloid protein or a superantigen other than gp120; said IgV comprises a nucleophilic site; said IgV catalyzes the hydrolysis of said amyloid protein or superantigen; and said IgV is obtained from an organism without prior immunization with said antigen.

9. A method for identifying an immunoglobulin (Ig) variable (V) domain of a light chain subunit (VL) or heavy chain subunit (VH) of an immunoglobulin having a specific, defined antigenic-directed activity comprising:

fractionating a library containing a plurality of IgV domains using antigen electrophilic analogs, wherein said plurality of IgV domains comprise IgV domains which comprise a VL domain linked to a VL domain, wherein the antigen of said IgV is an amyloid protein or a superantigen other than gp120; said IgV comprises a nucleophilic site; said IgV catalyzes the hydrolysis of said amyloid protein or superantigen; and said IgV is obtained from an organism without prior immunization with said antigen.

10. The method of claim 1, wherein said single IgV domain is a VL domain.

11. The method of claim 2, wherein said single IgV domain is a VL domain.

12. The method of claim 8, wherein said library of IgV domains is obtained from lymphoid cells from an organism with lupus, Alzheimer's disease, a *Staphylococcus aureus* infection, an HIV infection or an HCV infection.

13. The method of claim 9, wherein said library of IgV domains is obtained from lymphoid cells from an organism with lupus, Alzheimer's disease, a *Staphylococcus aureus* infection, an HIV infection or an HCV infection.

14. The method of claim 8, wherein the catalytic activity hydrolyzes one or more peptide bonds in amyloid β peptide, a *Staphylococcus aureus* protein, or HCV E2.

15. The method of claim 9, wherein the catalytic activity hydrolyzes one or more peptide bonds in amyloid β peptide, a *Staphylococcus aureus* protein, or HCV E2.

16. The method of claim 8, wherein said library of IgV domains is a phage-displayed IgV library.

17. The method of claim 9, wherein said library of IgV domains is a phage-displayed IgV library.

* * * * *